United States Patent
Donahoe et al.

(10) Patent No.: US 11,998,590 B2
(45) Date of Patent: *Jun. 4, 2024

(54) USE OF MULLERIAN INHIBITING SUBSTANCE (MIS) PROTEINS FOR CONTRACEPTION AND OVARIAN RESERVE PRESERVATION

(71) Applicant: THE GENERAL HOSPITAL CORPORATION, Boston, MA (US)

(72) Inventors: Patricia K. Donahoe, Boston, MA (US); David Pepin, Somerville, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 186 days.

This patent is subject to a terminal disclaimer.

(21) Appl. No.: 16/988,248

(22) Filed: Aug. 7, 2020

(65) Prior Publication Data

US 2020/0376082 A1 Dec. 3, 2020

Related U.S. Application Data

(63) Continuation of application No. 15/103,568, filed as application No. PCT/US2014/069829 on Dec. 11, 2014, now Pat. No. 11,135,269.

(60) Provisional application No. 61/914,671, filed on Dec. 11, 2013.

(51) Int. Cl.

| A61K 38/22 | (2006.01) |
|---|---|
| A61K 9/00 | (2006.01) |
| A61K 38/17 | (2006.01) |
| A61P 15/08 | (2006.01) |
| A61P 15/18 | (2006.01) |
| C12N 7/00 | (2006.01) |

(52) U.S. Cl.
CPC ............ *A61K 38/22* (2013.01); *A61K 9/0019* (2013.01); *A61K 38/17* (2013.01); *A61P 15/08* (2018.01); *A61P 15/18* (2018.01); *C12N 7/00* (2013.01); *C12N 2750/14142* (2013.01); *C12N 2750/14171* (2013.01)

(58) Field of Classification Search
None
See application file for complete search history.

(56) References Cited

U.S. PATENT DOCUMENTS

| 4,753,794 | A | 6/1988 | Donahoe |
|---|---|---|---|
| 5,010,055 | A | 4/1991 | Donahoe |
| 5,661,126 | A | 8/1997 | Donahoe et al. |
| 5,759,802 | A | 6/1998 | Maki et al. |
| 6,428,978 | B1 | 8/2002 | Olsen et al. |
| 6,673,352 | B1 | 1/2004 | Donahoe et al. |
| 11,135,269 | B2 | 10/2021 | Donahoe et al. |
| 2003/0124620 | A1 | 4/2003 | Seifer et al. |
| 2004/0062750 | A1 | 1/2004 | Donahoe et al. |
| 2005/0186664 | A1 | 8/2005 | Rosen et al. |
| 2006/0216294 | A1 | 8/2006 | McLennan et al. |
| 2009/0304675 | A1 | 12/2009 | McLennan et al. |
| 2010/0233689 | A1 | 9/2010 | Teixeira et al. |
| 2013/0189327 | A1 | 7/2013 | Ortega et al. |
| 2016/0039898 | A1 | 2/2016 | Donahoe |
| 2016/0228514 | A1 | 8/2016 | Donahoe |
| 2016/0310574 | A1 | 10/2016 | Donahoe et al. |

FOREIGN PATENT DOCUMENTS

| EP | 1074265 A1 | 2/2001 |
|---|---|---|
| WO | 1988000054 A1 | 1/1988 |
| WO | 1989006695 A1 | 7/1989 |
| WO | H-02117384 | 5/1990 |
| WO | 1992013951 A1 | 8/1992 |
| WO | 2001008695 A2 | 2/2001 |
| WO | 2001019387 A1 | 3/2001 |
| WO | 2003016514 A1 | 2/2003 |
| WO | 2005030963 A1 | 4/2005 |
| WO | 2009012357 A2 | 1/2009 |
| WO | 2014164981 A1 | 10/2014 |
| WO | 2015041718 A1 | 3/2015 |
| WO | 2015089321 A2 | 6/2015 |
| WO | 2018112168 A1 | 6/2018 |
| WO | 2022204119 A1 | 9/2022 |

OTHER PUBLICATIONS

Zincarelli et al., Mol Ther. 2008;16(6):1073-80 (Year: 2008).*
Cumming et al., The Journal of Cell Biology, vol. 177, No. 1, Apr. 9, 2007 7-11 (Year: 2007).*
Bhattacharya et al., "Impact of genetic variation on three dimensional structure and function of proteins", PLoS One (2017).
Behringer et al., "Abnormal sexual development in transgenic mice chronically expressing Mullerian inhibiting susbstance", Nature 345(6271): 167-170 (1990).
Benatar et al., "Lost in translation: treatment trials in the SOD1 mouse and in human ALS", Neurobiol Dis 26(1): 1-13 (2007).
Carter et al., "Fusion partners can increase the expression of recombinant interleukins via transient transfection in 2936E cells", Protein Sci 19(2): 357-362 (2010).

(Continued)

*Primary Examiner* — Christina M Borgeest
(74) *Attorney, Agent, or Firm* — Nixon Peabody LLLP; David S. Resnick; Susanna C. Benn

(57) ABSTRACT

One aspect of the invention provides a method of contraception by administering to a female subject a composition comprising Mullerian inhibiting substance (MIS). The MIS can be produced endogenously in the subject by a vector, where the vector comprises a polynucletide encoding a recombinant MIS protein. In some embodiments, the contraception is permanent and only requires administration of the composition once. Another aspect of the invention relates to a method of preserving an ovarian reserve, the method comprising administering to a female subject a composition comprising MIS or an inducible vector that comprises a polynucleotide encoding a recombinant MIS protein.

31 Claims, 4 Drawing Sheets

Specification includes a Sequence Listing.

(56) References Cited

OTHER PUBLICATIONS

Clowse et al., "Ovarian Preservation by GnRH Agonists during Chemotherapy: A Meta-Analysis", Journal of Women's Health 18(3): 311-319 (2009).
Dibernardo et al., "Translating preclinical insights into effective human trials in ALS", Biochim Biophys Acta 1762(11-12):1139-1149 (2006).
Durlinger et al., "Anti-Mullerian Hormone Inhibits Initiation of Primordial Follicle Growth in the Mouse Ovary", Endocrinology 143(3): 1076-1084 (2002).
Durlinger et al., "Control of Primordial Follicle Recruitment by Anti-Mullerian Hormone in the Mouse Ovary", Endocrinology 140(12): 5789-5796 (1999).
Kurian et al., "Cleavage of Müllerian inhibiting substance activates antiproliferative effects in vivo", Clin Cancer Res 1(3): 343-349 (1995).
MacLaughlin et al., "Müllerian inhibiting substance/anti-Müllerian hormone: a potential therapeutic agent for human ovarian and other cancers", Future Oncol, 6(3): 391-405 (2010).
Maeda et al., "Efficient production of active TNF-alpha by albumin signal peptide", Biochem Mol Biol Int 42(4): 825-832 (1997).
Papakostas et al., "Development of an efficiently cleaved, bioactive, highly pure FLAG-tagged recombinant human mullerian Inhibiting Substance", Protein Expr Purif. 70(1): 32-38 (2010).
Pepin et al., "An albumin leader sequence coupled with a cleavage site modification enhances the yield of recombinant C-terminal Mullerian Inhibiting Substance", Technology 1(1): 63-71 (2013).
Pieretti-Vanmarcke et al., "Mullerian Inhibiting Substance enhances subclinical doses of chemotherapeutic agents to inhibit human and mouse ovarian cancer", PNAS 103(46): 17426-17431 (2006).
Search result generated on May 17, 2017 shows SEQ ID No. 3 integrated into UniProtKB/Swiss-Prot in 1986; 4 pages total.
Akira. "Ovarian Reserve." Sanfujin-ka Tiryo (Obstetrics and gynecology treatment), vol. 102, p. 547-551 (2011) [English Translation Included].
Skaar et al., "Proteolytically activated, recombinant anti-mullerian hormone inhibits androgen secretion, proliferation, and differentiation of spermatogonia in adult zebrafish testis organ cultures", Endocrinology 152(9): 3527-3540 (2011).
Teixeira et al., "Müllerian-Inhibiting Substance Regulates Androgen Synthesis at the Transcriptional Level", Endocrinology 140(10): 4732-4738 (1999).
UniProtKB MIZ-Human [online] [Retrieved on Jun. 10, 2016]. Web. <URL:http:uniprot.org/uniprot/P03971.txt?version=138. (Nov. 30, 2010) Entire Document.
Zou et al., "Overexpression of human transforming growth factor-beta1 using recominant CHO cell expression system", Protein Expression and Purificaiton 37(2): 265-272 (2004).
Shulman. "Mullerian Anomalies." Clinical Obstetrics and Gynecology 51(1): 214-222 (2008).
Jafarlou et al. "An Overview of the History, Applications, Advantages, Disadvantages and Prospects of Gene Therapy." Journal of Biological Regulators & Homeostatic Agents 30(2): 315-321 (2016).
Nachtigal et al. "Bioactivation of Mullerian inhibiting substance during gonadal development by a kex2/subtilisin-like endoprotease." Proc. Natl. Acad. Sci. USA 93(15): 7711-7716 (1996).
Nakayama. "Furin: a mammalian subtilisin/Kex2p-like endoprotease involved in processing of a wide variety of precursor proteins." Biochem. J. 327(3): 625-635 (1997).
Phillips. "The challenge of gene therapy and DNA delivery." Journal of Pharmacy and Pharmacology. 53(9): 1169-1174 (2001).
Winkler. "Oglionucleotide conjugates for therapeutic applications." Ther. Deliv. 4(7): 791-809 (2013).
Bordo et al., "Suggestions for "safe" residue substitutions in site-directed mutagenesis." Journal of molecular biology 217.4 (1991): 721-729.

Kano et al., "AMH/MIS as a contraceptive that protects the ovarian reserve during chemotherapy", Proc Natl Acad Sci USA 114(9) E1688-E1697 (2017).
Kano et al., "AMH/MIS as a contraceptive that protects the ovarian reserve during chemotherapy", Proc Natl Acad Sci USA 114(9) (2017) Supplemental Figures (2 pages).
Donahoe, "Müllerian Inhibiting Substance in Reproduction and Cancer." Molecular Reproduction and Development 32(2):168-172 (1992). doi:10.1002/mrd.1080320213.
Hirobe et al. "Müllerian Inhibiting Substance Gene Expression in the Cycling Rat Ovary Correlates with Recruited or Graafian Follicle Selection." Biology of Reproduction 50(6):1238-1243 (1994), doi:10.1095/biolreprod50.6.1238.
Nagykery et al. "Evaluation of a Second-Generation AAV9-MIS Vectored Contraceptive in Cats." Abstract at p. 15 of the Proceedings of the International Symposium on Canine and Feline Reproduction—European Veterinary Society for Small Animal Reproduction (ISCFR-EVSSAR) Symposium (Jun. 30-Jul. 2, 2022).
Pepin "Gene Therapy using AAV9-delivery of an MIS Transgene Inhibits Estrus in Female Cats." Presentation presented at the Sixth International Symposium on Non-Surgical Methods of Pet Population Control. Alliance for Contraception in Cats & Dogs, 24 pages (Jul. 22-24, 2018).
Pepin et al. "Gene Therapy with Müllerian Inhibiting Substance as a Female Dog and Cat Contraceptive with Lifetime Suppression of Fertility." Abstract at p. 23 of Proceedings of the 8th International Symposium on Canine and Feline Reproduction (Jun. 22-25, 2016).
Pepin et al. "Gene Therapy with AAV9 delivery of an MIS Transgene Inhibits Estrus in Female Cats." Abstract from the Sixth International Symposium on Non-Surgical Methods of Pet Population Control. Alliance for Contraception in Cats & Dogs, 2 pages (Jul. 22-24, 2018).
Takahashi et al. "Müllerian inhibiting substance as oocyte meiosis inhibitor." Molecular and Cellular Endocrinology 47(3):225-34 (1986). doi:10.1016/0303-7207(86)90116-4.
Tsafriri et al. "Immunopurified Anti-Müllerian Hormone Does Not Inhibit Spontaneous Resumption of Meiosis In Vitro of Rat Oocytes." Biology of Reproduction 38(2):481-5 (1988). doi:10.1095/biolreprod38.2.481.
Ueno et al. "Human Recombinant Müllerian Inhibiting Substance Inhibition of Rat Oocyte Meiosis Is Reversed by Epidermal Growth Factor In Vitro." Endocrinology 123(3): 1652-1659 (1988). doi:10.1210/endo-123-3-1652.
Vansandt et al. "Gene Therapy-Induced Overexpression of Müllerian Inhibiting Substance (MIS) Produces Long-Term Contraception in Female Domestic Cats." Abstract at p. 19 of the Proceedings of the International Symposium on Canine and Feline Reproduction—European Veterinary Society for Small Animal Reproduction (ISCFR-EVSSAR) Symposium (Jun. 30-Jul. 2, 2022).
Zhang et al. "Effect of Anti-Mullerian Hormone in Culture Medium on Quality of Mouse Oocytes Matured In Vitro." PloS One 9(6):e99393 (2014). doi:10.1371/journal.pone.0099393.
Godin. Viral vector delivery of an AMH transgene as a promising contraceptive in female domestic cats. SSR Oral Presentation Jul. 14, 2023.
Godin. Single delivery of an AMH transgene using an AAV9 vector is safe and results in long-term contraception in the female domestic cat. SSR Poster Jul. 14, 2023.
Godin and Vansandt. Gene Delivery Approach With AMH for Single-Dose Lifetime Contraception in Female Cats. Botstiber Webinar, Sep. 21, 2023.
D. Pepin. Use of a gene delivery approach for single dose lifetime sterility in female cats: an alternative to spay. ASGCT Presentation, May 20, 2023.
M. Ridings, Gene Therapy Produces Long-term Contraception in Female Domestic Cats, (2023).
Vansandt et al., Nature Communications (Including supplemental data), Jun. 6, 2023.
WSAVA Presentation Slides, 48th World Small Animal Veterinary Association of Congress and 28th FECAVA Eurocongress. Sep. 2023.

* cited by examiner

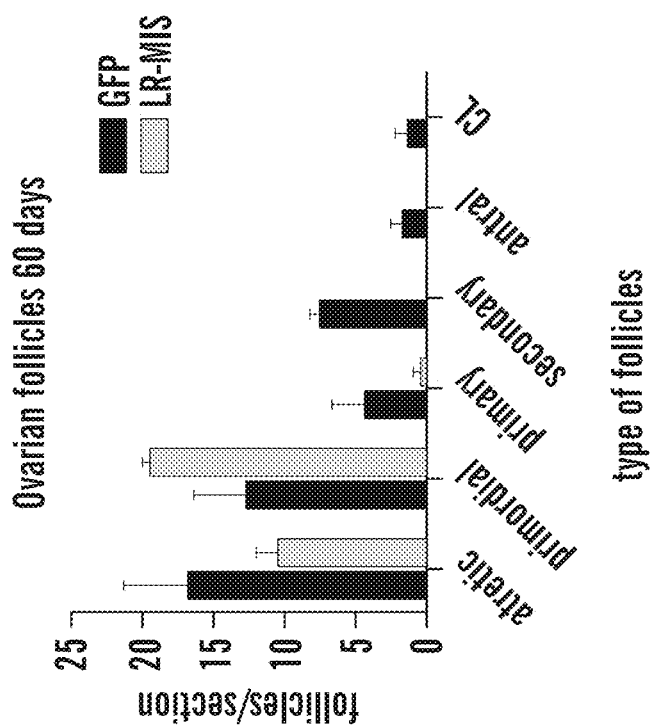
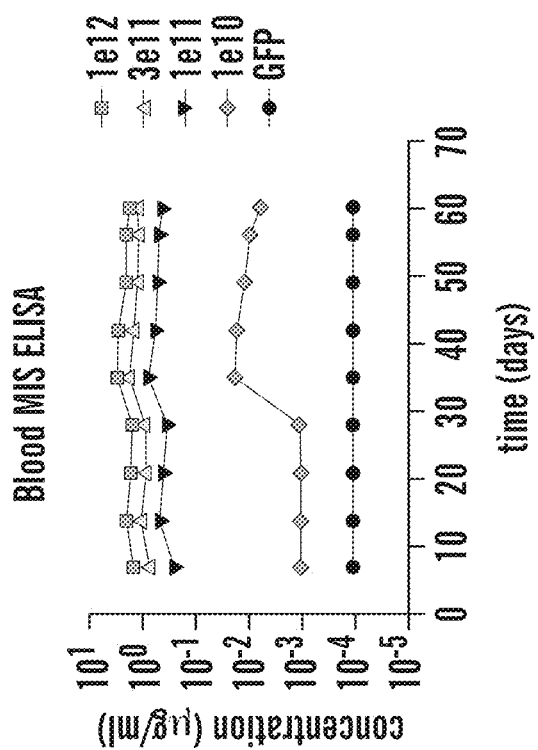
FIG. 1A
FIG. 1B

USE OF MULLERIAN INHIBITING SUBSTANCE (MIS) PROTEINS FOR CONTRACEPTION AND OVARIAN RESERVE PRESERVATION

CROSS-REFERENCE TO RELATED APPLICATION

This application is a continuation under 35 U.S.C. § 120 of U.S. application Ser. No. 15/103,568 filed Jun. 10, 2016, which is a 371 National Phase Entry of International Patent Application No. PCT/US2014/069829 filed on Dec. 11, 2014 which claims benefit under 35 U.S.C. § 119(e) of U.S. Provisional Application No. 61/914,671 filed Dec. 11, 2013, the contents of which are incorporated herein by reference in their entirety.

FIELD OF THE INVENTION

The present invention relates to methods of contraception and/or ovarian reserve preservation using Mullerian inhibiting substance (MIS) proteins and variants thereof. In some embodiments, a MIS protein or MIS protein variant is administered to a subject. In some aspects, MIS protein or a MIS protein variant is produced endogenously in a female subject by a vector comprising a polynucleotide encoding a recombinant MIS protein or MIS protein variant.

SEQUENCE LISTING

The instant application contains a Sequence Listing which has been submitted electronically in ASCII format and is hereby incorporated by reference in its entirety. Said ASCII copy, created on Jun. 10, 2016, is named 030258-083221-PCT_SL.txt and is 26,944 bytes in size.

BACKGROUND OF THE INVENTION

Mullerian Inhibiting Substance (MIS) also known as anti-Mullerian hormone (AMH), is a 140-kDa disulfide-linked homodimer glycoprotein member of the large transforming growth factor-β (TGFβ) multigene family of glycoproteins. The proteins in this gene family are all produced as dimeric precursors and undergo posttranslational processing for activation, requiring cleavage and dissociation to release bioactive C-terminal fragments. Similarly, the 140 kilodalton (kDa) disulfide-linked homodimer of MIS is proteolytically cleaved to generate its active C-terminal fragments.

MIS, is a reproductive hormone produced in fetal testes, which inhibits the development of female secondary sexual structures in males. Before sexual differentiation, the fetus is bipotential, and the developmental choice of male Wolffian ducts (i.e. prostate, vas deferens) over female Mullerian ducts (i.e. Fallopian tubes, uterus, vagina) in the male is controlled in part by MIS.

The human MIS gene is located on chromosome 19, and its expression is sexually dimorphic. In males, MIS expression begins at 9 weeks gestation in the fetal testes and continues at high levels until puberty, when expression levels fall dramatically. In females, MIS is produced only postnatally in granulosa cells from prepuberty through menopause at levels similar to adult males, after which expression ceases. In male fetuses MIS causes regression of the Mullerian ducts, the precursors to the Fallopian tubes, uterus, cervix, and upper third of the vagina.

Endogenously, MIS is produced by the granulosa cells and is an important gatekeeper of primordial follicle recruitment into the growing pool. In males, overexpression of MIS inhibits leydig cells steroidogenesis, causing a marked drop in testosterone levels (Teixeira et al, 1999).

SUMMARY OF THE INVENTION

The present invention is relates to using MIS proteins and MIS protein variants with increased bioactivity and potency as compared to the wild type MIS protein for use in contraceptive methods and in methods to protect female's ovarian reserve. The present invention is based upon the discovery that the human MIS protein arrests folliculogenesis at the initial stage of primordial follicles. In particular, the inventors have demonstrated that in a mouse model of fertility, that administration of human MIS protein, e.g., via gene therapy, can prevent follicle maturation and oocyte release, thus inhibiting ovulation, and importantly have demonstrated in a mouse model in vivo, mice administered human MIS protein are unable to reproduce or have significantly reduced reproduction rates. Accordingly, one aspect of the present invention provides a method of contraception in a female subject, the method comprises administering to the female subject a composition comprising MIS. Accordingly, the methods can be used to prevent a subject from becoming pregnant and preventing reproduction.

Herein, the inventors have also demonstrated that administration of MIS protein, e.g., via gene therapy, can prevent the age-related decrease in the number of primordial ovarian follicles in a mouse model in vivo. Accordingly, another aspect of the present invention provides a method of preserving ovarian reserve, or preventing female age-related decreases in ovarian follicles, the method comprises administering to the female subject a composition comprising MIS. Accordingly, the present invention can be used in subjects who are in need of preserving their ovarian reserve, for example, subjects whom have a desire to delay reproduction until a later time point in their life, and/or subjects whom which to prolong their reproductive years, as well as subjects who have, or are at risk of premature ovarian aging (POA) (also known as occult primary ovarian insufficiency). In some embodiments, the methods comprising administering a MIS protein or nucleic acid encoding a MIS protein are administered to a subject with diminished ovarian reserve (DOR) to prevent further decreases in ovarian reserves.

Accordingly, one aspect of the present invention relates to a method of contraception comprising administering to a female subject a composition comprising a Mullerian Inhibiting Substance (MIS) protein.

Another aspect of the present invention relates to a method of preventing a decline in the functional ovarian reserve (FOR) in a female subject, comprising administering to the female subject a composition comprising a Mullerian Inhibiting Substance (MIS) protein. In some embodiments, preventing a decline in the functional ovarian reserve (FOR) in a female subject relates to a method of preserving ovarian reserve in the subject. In some embodiments, such a method inhibits the natural age-related decline in FOR by at least a 10%, or at least 20%, or at least 30%, or at least 40%, or at least 50% or more than 50% as compared to an age-matched subject not administered the MIS protein or MIS protein variants as disclosed herein.

In some embodiments, the MIS protein comprises amino acid residues 26-560 of SEQ ID NO: 3 or a polypeptide which has at least 95% sequence identity to the amino acid sequence of amino acid residues 26-560 of SEQ ID NO: 3.

In some embodiments, the MIS protein, comprises amino acid residues 25-559 of SEQ ID NO: 4 or a polypeptide which has at least 95% sequence identity to the amino acid sequence of amino acid residues 25-559 of SEQ ID NO: 4. In some embodiments, the MIS protein comprises amino acid residues 25-567 of SEQ ID NO: 5 or a polypeptide which has at least 95% sequence identity to the amino acid sequence of amino acid residues 25-567 of SEQ ID NO: 5.

In some embodiments, the MIS protein is produced by a vector, wherein the vector comprises a polynucleotide encoding the MIS protein operatively linked to a promoter, for example, a viral vector, selected from the group consisting of; an adenoviral (Adv) vector, an AAV vector, a poxvirus vector and a lentiviral vector. In some embodiments, the MIS protein is encoded by a polynucleotide sequence corresponding to SEQ ID NO: 1 or a polynucleotide which has at least 95% sequence identity to the nucleic acid sequence of SEQ ID NO: 1. In some embodiments, the MIS protein is encoded by a polynucleotide sequence corresponding to SEQ ID NO: 2 or a polynucleotide which has at least 95% sequence identity to the nucleic acid sequence of SEQ ID NO: 2.

In some embodiments, composition further comprises a pharmaceutically acceptable carrier.

In some embodiments of all aspects of the invention, the female subject is an animal, such as a cat or a dog. In some embodiments, the female subject is a human female.

Administration can be by any method and route commonly known to one of ordinary skill in the art, and can include, for example, a one-time injection (e.g., in the case of gene therapy, for example where it is desirable to have permanent contraception) or via pulse administration followed by an interval of no administration, e.g., where it is desirable to have temporary arrest of folliculogenesis, such as in a temporary method of contraception or where pregnancy is desired at a later period in the subjects lifetime. In some embodiments, pulsed administration comprises administration of the MIS protein or MIS protein variant followed by an interval at least 3 days, or at least 7 days between about 7 days and 3 weeks of no treatment between pulsed administration of the composition as disclosed herein. In some embodiments, administration is subcutaneous administration, or administration via a transdermal patch, ring, biogel or injection.

In some embodiments, a MIS protein or MIS protein variant as disclosed herein is administered at sufficiently high concentrations for complete arrest in folliculogenesis in the subject. In some embodiments, MIS administered to the subject in a sufficient amount to increase the concentration of the MIS protein in the blood of the subject by 10% to 50% higher as compared to the absence of administration of MIS, or to increase the concentration of the MIS protein in the blood of the subject by 50% to 100% higher as compared to the absence of administration of MIS, or to increase the concentration of the MIS protein in the blood of the subject by 2 to 5-fold higher or more than 5-fold as compared to the absence of administration of MIS. In some embodiments, MIS administered to the subject in a sufficient amount to increase the concentration of the MIS protein in the blood of the subject to between 1 µg/ml-5 µg/ml.

BRIEF DESCRIPTION OF THE DRAWINGS

FIGS. 1A-1C show AAV9-MIS treatment in mice. FIG. 1A shows blood MIS protein levels by ELISA following single infection of various titers of AAV9-LR-MIS or GFP. FIG. 1B) Follicle counts in mice treated with $3 \times 10^{11}$ virus for 60 days. FIG. 1C) Sections of MIS and GFP ovaries at the largest diameter at 60 days (same magnification, insert 10×). Note the abundance of primordial follicles in the smaller LR-MIS ovary.

DETAILED DESCRIPTION OF THE INVENTION

Figure 1C:
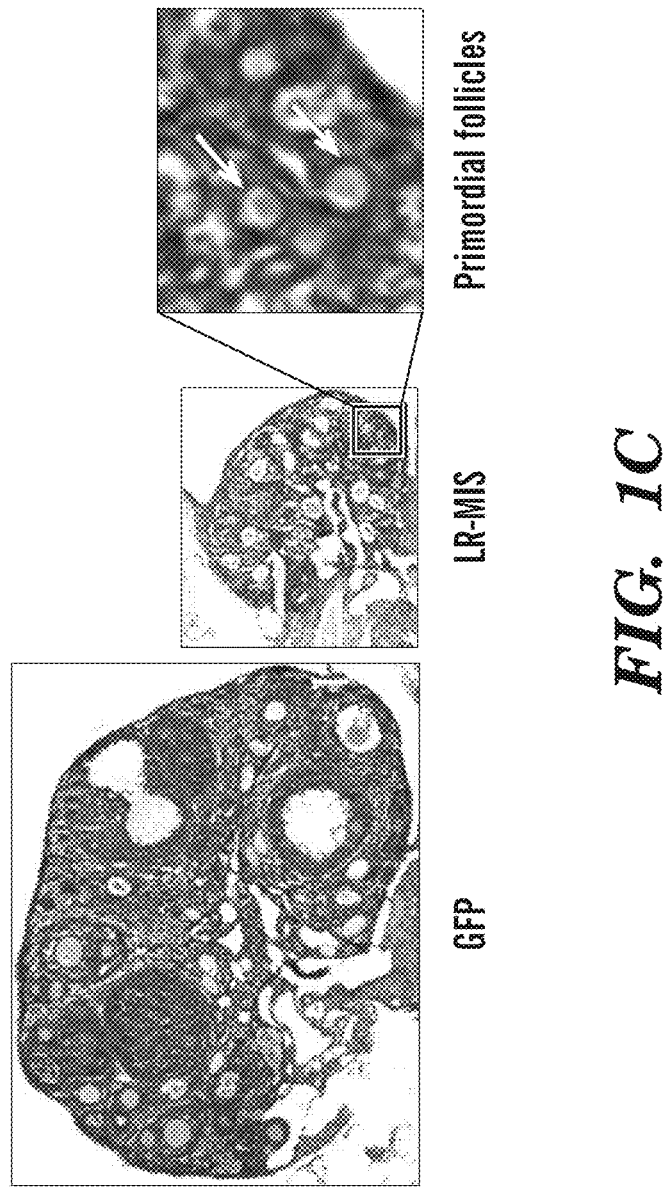

The present invention relates to using MIS proteins and MIS protein variants with increased bioactivity and potency as compared to the wild type MIS protein for use in contraceptive methods and in methods to protect female's ovarian reserve.

In one aspect, the present invention relates to method of administering a Mullerian inhibiting substance (MIS) protein, or a nucleic acid encoding the same, to a female subject as a female contraception. The present invention is based upon the discovery that human MIS protein arrests folliculogenesis at the initial stage of primordial follicles. Folliculogenesis is the maturation of the ovarian follicle, which involves the recruitment of primordial follicles that develop into large preovulatory follicles before entering the menstrual cycle. When folliculogenesis is arrested, the maturation of the ovarian follicle is stopped, which can significantly reduce the probability of pregnancy.

In particular, the inventors have demonstrated that administration of human MIS protein, e.g., via gene therapy to mice can inhibit follicle maturation and oocyte release, thus inhibiting ovulation. Importantly, the inventors have demonstrated that mice administered human MIS protein in vivo are unable to reproduce or have significantly reduced reproduction rates as compared to control treated mice. Accordingly, one aspect of the present invention provides a method of contraception in a female subject, the method comprises administering to the female subject a composition comprising MIS. Accordingly, the methods can be used to prevent a subject from becoming pregnant and preventing reproduction. Administration of MIS as a contraceptive, or to prevent pregnancy is surprising considering MIS is typically suppressed by hormonal contraceptives (Kushnir et al., "Ovarian Reserve screening before contraception?" Reproductive Biomedicine Online, 2014; 29; 527-529; Dolleman et al., "Reproductive and lifestyle determinants of anti-mullerian hormone in a large population-based study" J. Clin Endocrinol. Metabol., 2013, 98; 2106-2115).

Herein, the inventors have also demonstrated that administration of high levels of MIS protein, e.g., via gene therapy, can prevent the age-related decrease in the number of primordial ovarian follicles in a mouse model in vivo. Importantly, while MIS has been previously reported to play a role in primordial follicle recruitment and inhibit primordial follicle growth in a mouse ovary (Durlinger et al., Endocrinology, 1999; 140; 5789-5796; Durlinger et al., Endocrinology, 2002; 143(3); 1076-1084), was it surprising that high levels of MIS could inhibit the maturation of ovarian follicles, because it was previously shown that abnormal sexual development occurred in transgenic mice chronically expressing MIS (Behringer et al., Let. Nature, 1990; 345; 167-170). Moreover, while MIS has been reported to inhibit primordial follicle recruitment, the observed magnitude of the MIS inhibitory effect has always been somewhat small. In contrast, the inventors herein have surprisingly discovered that with sufficiently high levels of MIS there is a complete arrest in folliculogenesis, demonstrating that MIS alone is sufficient to regulate primordial follicle recruitment.

MIS levels in the blood is often used in assessing functional ovarian reserve (FOR) in human females as MIS levels are reflective of the follicular pool (because all growing follicles secrete MIS) and endogenous MIS is a negative feedback regulator to avoid over-recruitment of primordial follicles once sufficient numbers of follicles are already growing. Therefore, decreased MIS levels are indicative of a female subject with a small growing follicle pool, which demonstrates a small ovarian reserve (few primordial follicles left) and an "aged" ovary and abnormally high levels of MIS can be used as an early diagnosis for female subjects at risk of premature ovarian aging (POA) (Pigny et al., Serum anti-mullerian hormone as a surrogate for antral follicle count for definition of the polycystic ovary syndrome, J. Clin Endocrinol. Metabol., 2006, 91; 941-945), and high levels of MIS is associated during middle age is associated with abnormally low functional ovarian reserve (FOR) (Gleicher et al., FMR1 genotype with autoimmunity-associated polycystic ovary-like phenotype and deceased pregnancy chance, PLos one, 2010, 5, e15303). Accordingly, given that high levels of MIS in the blood can identify a subject with premature ovarian aging (POA) and low functional ovarian reserve (FOR), it is surprising that the inventors discovered that maintaining high levels of MIS with administration of exogenous MIS (e.g., protein or gene therapy) was able to blocking recruitment of primordial follicles and keep the ovary in a quiescent state, similar to that of a pre-pubertal woman.

Accordingly, another aspect of the present invention provides a method of preserving ovarian reserve, or preventing female age-related decrease in ovarian follicles, or preventing age-related decline in functional ovarian reserve (FOR), the method comprises administering to the female subject a composition comprising MIS. Accordingly, the present invention can be used in subjects who are in need of preserving their ovarian reserve, for example, subjects whom have a desire to delay reproduction until a later time point in their life, and/or subjects whom which to prolong their reproductive years, as well as subjects who have, or are at risk of premature ovarian aging (POA) (also known as occult primary ovarian insufficiency). In some embodiments, the methods comprising administering a MIS protein or nucleic acid encoding a MIS protein are administered to a subject with diminished ovarian reserve (DOR) to prevent further decreases in ovarian reserves.

Subjects Amenable to Administration of MIS Proteins and MIS Variant Proteins

In all aspects of the present invention, a subject amenable to treatment with the methods and compositions as disclosed herein is a female human.

MIS as a Contraceptive Agent

As discussed herein, one aspect of the present invention relates to administering MIS proteins and MIS variant proteins to a female subject as a method of contraception. Accordingly, the methods as disclosed herein can be used to prevent a female subject from becoming pregnant and thereby preventing reproduction. Methods for using MIS as a contraceptive agent or to prevent a subject becoming pregnant as disclosed herein comprise administering a MIS protein, or MIS variant protein as disclosed herein (e.g., LR-MIS), or a nucleic acid encoding the same to the subject. Importantly, while the inventors have previously reported use of MIS as a contraceptive agent, see U.S. Pat. No. 4,753,794, which is incorporated herein in its entity, use of MIS protein variants, such as LR-MIS or LRF-MIS or RF-MIS, or gene therapy for a one-time administration of MIS proteins for contraception has not been shown or reported.

Subjects amenable to treatment include any subject who has the desire not to become pregnant. Subjects can be administered MIS proteins or MIS protein variants (such as LR-MIS), or nucleic acids encoding MIS proteins on a temporary basis or a more long-term or permanent basis depending on the female subjects desire to temporary prevent getting pregnant, or permanently prevent becoming pregnant upon unprotected sexual activity or intercourse. Suitable subjects include any female, e.g., human female, within the age range of about 15-55 years, or about 15-25 years, or about 25-35 years, or about 35-55 years or older than 55-years. In some embodiments, the subject is a non-human subject, for example, where controlling the population of the non-human species is important. In some embodiments, the subject is an animal. In some embodiments, the animal is a cat or dog or any feral animal. In some embodiments, the female subject is a human.

MIS to Prevent a Reduction in Ovarian Reserve

It is known in the art that a primordial follicle consists of an oocyte enclosed by a single layer of cells, and oocyte is a female germ cell involved in reproduction. Throughout reproductive life, the total number of primordial follicles, also called the ovarian reserve, steadily declines over time as a consequence of recruitment and cell death (McGee and Huseh, Endocrine Reviews 2000, 21 200-214). And depletion of the ovarian reserve results in female infertility. Without wishing to be bound by theory, when folliculogenesis is arrested or blocked, primordial follicles are prevented from being recruited, effectively removing one main factor that contributes to the depletion of the ovarian reserve. Accordingly, a related aspect of the invention relates to a method of preserving an ovarian reserve in a female subject, comprising administering to the female subject a composition comprising MIS or an inducible vector that comprises a polynucleotide encoding a recombinant MIS protein.

Accordingly, as discussed herein, another aspect of the present invention relates to administering MIS proteins and MIS variant proteins to a female subject in a method to preserve ovarian reserve, or to prevent an age-related decrease in ovarian follicles. Methods for using MIS as a contraceptive agent or to prevent a subject becoming pregnant as disclosed herein comprise administering a MIS protein, or MIS variant protein as disclosed herein (e.g., LR-MIS), or a nucleic acid encoding the same to the subject.

Subjects amenable to treatment include any female subject who has the desire to delay pregnancy, or to become pregnant at a later point in their lifetime, or to delay their childbearing years to a later time point in their life. Suitable subjects include any female, e.g., human female, within the age range of about 25-30 years, or about 30-35 years, or about 35-40 years, or about 40-45 years or older than 45-years.

As such, another aspect of the present invention relates to administering MIS proteins and MIS variant proteins to a female subject in a method to preserve ovarian reserve, e.g., for subjects who are in need of preserving their ovarian reserve, such as subjects whom have a desire to delay reproduction until a later time point in their life, and/or subjects whom wish to prolong their reproductive years, as well as subjects who have, or are at risk of premature ovarian aging (POA) (also known as occult primary ovarian insufficiency). In some embodiments, the methods comprising administering a MIS protein or nucleic acid encoding a MIS protein are administered to a subject with diminished ovarian reserve (DOR) to prevent further decreases in ovarian reserves.

Subjects amenable to treatment are those experiencing age-related infertility, or have, or are at risk of premature ovarian aging (POA) (also known as occult primary ovarian insufficiency), or have premature ovarian failure (also known as primary ovarian insufficiency). In some embodiments, subjects amenable to treatment include any female human subject who has a symptom of post-contraception amenorrhoea, menstrual abnormalities or infertility upon cessation of non-MIS contraception.

In some embodiments, subjects amenable to treatment include any female human subject whom after a functional ovarian reserve (FOR) assessment is identified as having premature ovarian aging (POA) or diminished ovarian reserve (DOR). Screens to identify such subjects are well known in the art, and include measuring any one or more of; follicle stimulating hormone (FSH) levels, basal luteinising hormone (LH) and estradiol (E2), gonadotrophin-releasing hormone (GnRH), FSH:LH levels, inhibin A and B, progesterone (P4) and P4:E2 ratios, MIS levels, testosterone, vascular endothelial growth factor (VEGF), insulin-like growth factor-1 (IGF-1) and IGF-1:IGF-1 binding protein ratios (IGF-1:IGFBP-1 ratios), Clomiphene citrate challenge test (CCCT), gonadotrophin analogue stimulating test, exogenous FSH ovarian reserve test, ovarian biopsy, antral follicle count, ovarian volume, ovarian stromal blood flow, and are discussed in Johnson et al., (Ovarian reserve tests for producing fertility outcomes for assisted reproductive technology; the International Systematic Collaboration of Ovarian Reserve Evaluation Protocol for systematic review of ovarian reserve test accuracy, BJOG, 2006; 113; 1472-1480), which is incorporated herein in its entirety by reference.

Other subjects amenable to treatment in methods to preserve ovarian reserve include subjects any subject who has, or is likely to experience factors which predispose the female to premature ovarian aging (POA), including but not limited to iatragenic factors such as, ovarian surgery, chemotherapy, radiation therapy, bone marrow transplantation, anti-viral therapies and other medical risk factors. In some embodiments, the subject is undergoing chemotherapy, chemo-radiotherapy, radiotherapy or other cancer treatment. By preventing primordial follicles from being recruited, the risk of the primordial follicles being affected by chemotherapy drugs is reduced. Importantly, co-treatment of the compositions comprising a MIS protein or MIS protein variant thereof during chemotherapy can be used in a method to decrease or avoid drug-induced premature ovarian failure. Cytotoxic drugs, particularly chemotherapy which preferentially damages dividing cells is often very toxic to growing follicles. The loss of growing follicles causes a de-regulation of the negative feedback (i.e., temporarily lowers MIS levels), which leads to an over-recruitment of primordial follicles. Those follicles then also get damaged by the chemotherapeutic agents and the repeated chemotherapy cycle procedures until the ovary is depleted of all primordial follicles. Since women are born with a set amount of primordial follicles, premature ovarian failure due to chemotherapy or another condition is irreversible. Thus, the present invention encompasses admiration of MIS proteins and MIS protein variants to cancer patients during or after chemotherapeutic treatment to prevent deregulation and/or to re-establish the negative feedback provided by MIS.

In some embodiments, a female subject amenable to treatment according to the methods, compositions and kits as disclosed herein is a female subject pre-disposed to premature ovarian aging (POA).

In some embodiments, a subject amenable to the methods to preserve ovarian reserve as disclosed herein include subjects any subject who has, or is likely to have endometriosis, polycistric ovarian syndrome (PCOS), FMR1 mutations (e.g., measuring CGG repeats in FMR1 gene as disclosed in US Patent application, 2011/0020795 and 20140206756, which are incorporated herein in their entirety by reference), subjects with less than 26 GCC FMR1 repeats (het-norm/low-sub genome or hom/low/low-sub genome), BRAC1 mutations, turner syndrome, autoimmunity, thyroid autoimmunity (e.g., hyperthyroidism or hypothyroidism), adrenal autoimmunity, any other autoimmunity, autoimmunity polyglandular syndromes, family history of autoimmune disease (e.g., one $1^{st}$ degree or two $2^{nd}$ decree relatives), history of repeated pregnancy loss or history of early maternal/sibling menopause.

Administration of a composition comprising MIS or a MIS variant protein, or a nucleic acid encoding the same may be used in a method to slow, arrest and/or reverse premature ovarian aging (POA) and/or treat infertility.

Mullerian Inhibiting Substance (MIS) Proteins and MIS Protein Variants:

Without wishing to be bound by theory, the Mullerian Inhibiting Substance (MIS) is a member of the TGFβ multigene family of glycoproteins. The proteins in this gene family are all produced as dimeric precursors and undergo posttranslational processing for activation, requiring cleavage and dissociation to release bioactive C-terminal fragments. MIS is a 140-kDa dimer which consists of identical 70 kDa disulfide-linked monomers, each composed of a 57 kDa N-terminal domain and a 12.5 kDa carboxyl-terminal (C-terminal). Thus, MIS comprises 2 identical monomers (and thus is termed a "homodimer"), each monomer comprising two domains, the N-terminal and C-terminal domain, which are held in non-covalent association. The purified C-terminal domain is the biologically active moiety and cleavage is required for activity. The N-terminal domain may assist with protein folding in vivo and facilitate delivery of the C-terminal peptide to its receptor, e.g., MISRI and MISRII. A non-cleavable mutant of MIS is biologically inactive.

The carboxy-terminal active domain shares amino acid homology with other TGFβ family members, such as TGF-B 1, 2, and 3, inhibin, activin, and bone morphogenetic proteins, as well as a member of Growth and Differentiation Factors (GDFs). The structure of the MIS carboxy-terminal domain is supported by seven cysteines involved both in intra- and intermolecular disulfides bridges that lead to its structural stability, as revealed by homology to the three dimensional structure of TGFβ using molecular modeling (Lorenzo, Donahoe, et al., unpublished data).

Like other TGFβ family members, MIS can be cleaved by plasmin which generates its amino- and carboxy-terminal domains. This proteolytic process is required for its physiological activity and occurs at a site in a position similar to the dibasic cleavage site found in the sequence of TGFβ. The resultant products are tightly associated in a non-covalent complex that dissociates at low pH; therefore, technically complex and time-demanding protocols with plasmin treatment and molecular size exclusion chromatography are required to enhance or complete the separation of the carboxy terminus from the amino terminus.

Processing of the mature MIS protein involves the proteolytic cleavage and removal of the leader sequence (e.g., amino acids 1-25 of SEQ ID NO: 3), the cleavage of the MIS protein at the primary site to generate the N-terminal and C-terminal domains, and the formation of these domains into a monomer, which is disulfide linked by inter- and intrachain disulfide bonds to an identical monomer to form the bioactive homodimer MIS protein.

MIS contains two major cleavage sites that are sensitive to plasmin and result in difficult and complex purification of recombinant human MIS protein. There is a primary monobasic cleavage site is Q/R which is located at amino acid position 426-427 of human wild-type MIS protein (where the leader sequence has been cleaved) (the RAQ/R cleavage site corresponds to amino acid 448-451 of SEQ ID NO:3, which is the wild type hMIS protein including the leader sequence of 1-25 of SEQ ID NO: 3). Cleavage at this site, which releases the active carboxy-terminal domain of MIS, resembles a consensus furin cleavage site. A secondary cleavage site (referred to as "R/S"), is identified by amino-terminal sequencing of MIS fragments is located at residues 229-230 in the amino-terminal domain of wild-type MIS (corresponding to amino acids 254-255 of SEQ ID NO: 3). This site contains an R/S, but otherwise does not follow the consensus Arg-X-(Arg/Lys)-Arg for furin cleavage. Separation of purified carboxy-terminal from amino-terminal MIS after digestion with exogenous plasmin previously used molecular size-exclusion chromatography under acidic conditions. This technique requires extreme care to control MIS digestion, since long incubations of MIS in plasmin produced the carboxy-terminal MIS domain plus other fragments of 22 and 34 kDa, due to cleavage both at the primary and secondary sites, are extremely difficult to separate from one another by size exclusion. Since all fragments generated after plasmin digestion are glycosylated, except the carboxy-terminal domain, wheat-germ lectin affinity can be used as an alternative to size chromatography separation to purify the carboxy-terminal domain of MIS. After plasmin cleavage, the resulting fragments can be loaded onto a wheat germ lectin column at pH 3.5 in order to dissociate the amino- and carboxy-terminal domains, as disclosed in Lorenzo et al., J. Chromatography, (2001), 776; 89-98, which is incorporated herein its entirety by reference.

In order to make purification easier and to prevent the production of MIS fragments during purification, (e.g., where both the carboxy-terminal MIS domain plus a 22 and 34 kDa fragment are produced due to cleavage both at the primary and secondary sites), the inventors previously developed a modified recombinant MIS protein (herein referred to as "LR-MIS" and corresponds to SEQ ID NO:4) where the primary RAQ/R cleavage site at amino acid position 426-427 of human wild-type MIS (corresponding to amino acid 448-451 of SEQ ID NO:3 herein) was changed to RAR/R. This is disclosed in PCT application PCT/US14/024010, which is incorporated herein in its entirety by reference, where the inventors previously demonstrated that changing the Q at position 450 of SEQ ID NO:3 herein to a R allowed production of a highly purified cleaved preparation of human MIS protein that has full bioactivity.

Accordingly, in all aspects of the invention, a MIS protein for use in the method, compositions and kits as disclosed herein can be wild-type MIS comprising at least amino acids 26-560 of SEQ ID NO: 3, or alternatively, can be a modified MIS protein, or MIS variant where the primary cleavage site of residues 448-451 of SEQ ID NO:3 have been changed from RAQ/R to RAR/R (e.g., a MIS variant protein comprising at least amino acids 25-559 of SEQ ID NO: 4).

As discussed above, the mature wild-type MIS protein is initially produced as a prohormone comprising a N-terminal leader sequence, which corresponds to amino acid residues 1-25 of wild-type MIS protein of SEQ ID NO: 3. This leader sequence is cleaved off to render the mature MIS protein. In all aspects of the invention, a MIS protein or a nucleic acid sequence encoding the same for use in the method, compositions and kits as disclosed herein can have a non-endogenous MIS leader sequence, where the MIS leader sequence of amino acids 1-25 of SEQ ID NO: 3 has been replaced with different leader sequence, such as, for example, a human serum albumin leader sequences. In all aspects of the invention, a MIS protein or a nucleic acid sequence encoding the same for use in the method, compositions and kits as disclosed herein is a modified recombinant MIS protein (herein referred to as "LR-MIS") and corresponds to SEQ ID NO:4 where the primary RAQ/R cleavage site at amino acid position 426-427 of human wild-type MIS (corresponding to amino acid 448-451 of SEQ ID NO:3 herein) was changed to RAR/R, and where the endogenous MIS leader sequence has been replaced with an albumin leader sequence.

In some embodiments, a MIS protein or a nucleic acid sequence encoding the same for use in the method, compositions and kits as disclosed herein is a modified recombinant MIS protein comprising at least amino acids 25-559 of SEQ ID NO: 4 (where the primary RAQ/R cleavage site has been changed to RAR/R) and any suitable N-terminal leader sequence, such as those disclosed in PCT application PCT/US14/024010, which is incorporated herein in its entirety by reference.

Different non-endogenous leader sequences often improve the expression and/or secretion of a polypeptide of interest in a host cell, and are useful for the production of recombinant proteins. Generally, as an efficient method for production of a desired protein by a genetic engineering procedure involves it secretion from a cell, where the procedure involves the expression of a fused protein, e.g., comprising the desired protein (e.g., MIS) and a prepropeptide (signal peptide+propeptide) in a host cell and then its intracellular cleavage (e.g., processing) by enzymes of the host, followed by its extracellular secretion. According to this process, the fused protein must be cleaved twice by enzymes of the host to be a mature protein, resulting in lower yield of the mature protein and contamination of the mature protein with residual fused protein.

Accordingly, secreted proteins are expressed initially inside the cell in a precursor form containing a leader sequence ensuring entry into the secretory pathway. Such leader sequences, also referred to as signal peptides, direct the expressed product across the membrane of the endoplasmic reticulum (ER). Signal peptides are generally cleaved off by signal peptidases during translocation to the ER. Once entered in the secretory pathway, the protein is transported to the Golgi apparatus. From the Golgi the protein can follow different routes that lead to compartments such as the cell vacuole or the cell membrane, or it can be routed out of the cell to be secreted to the external medium (Pfeffer and Rothman (1987) Ann. Rev. Biochem. 56:829-852).

For Industrial production of a secreted protein, the protein to be produced needs to be secreted efficiently from the host cell or the host organism. The signal peptide may be, e.g., the native signal peptide of the protein to be produced, a heterologous signal peptide, or a hybrid of native and heterologous signal peptide. However, several problems are encountered with the use of currently known signal peptides. One problem often encountered when producing a human protein from a non-human host cell or organism is that the native signal peptide does not ensure efficient translocation and/or cleavage of the signal peptide. This leads to low rates of protein secretion and/or to secretion of mature proteins that display N-terminal extensions due to an incorrect cleavage of the signal peptide. Thus the choice of the signal peptide is of great importance for industrial production of a protein.

In addition of leader sequences directing the secretion of the protein, a precursor form can comprise supplemental leader sequences that are cleaved during maturation. These supplemental leader peptides, named propeptides, usually follow the signal peptide. Virtually all peptide hormones, numerous bioactive protein (for example, growth factors, receptors and cell-adhesion molecules, and including MIS), and many bacterial toxins and viral envelope glycoproteins comprise a propeptide that is post-translationally excised to generate the mature and biologically active protein (Seidah and Chretien (1999) Brain Res. 848:45-62).

Peptides are further cleaved by enzymes named proprotein convertases. Mammalian proprotein convertases include, e.g., the subtilisin convertases PCSK1, PCSK2 and furin. Furin is ubiquitously expressed and located in the trans-Golgi network. Furin proteolytically activates large numbers of proproteins substrates in secretory pathway compartments. (Thomas (2002) Nat Rev Mol Cell Biol. 3:753-766). More specifically, furin localizes to the Trans Golgi Network, a late Golgi structure that is responsible for sorting secretory pathway proteins to their final destinations, including the cell surface, endosomes, lysosomes and secretory granules. The site that furin cleaves has been extensively studied. The cleavage site is positioned after the carboxyl-terminal arginine of the consensus sequence R-X-L/R-R, wherein X may represent any amino acid (Nakayama (1997) Biochem. J 327:625-635). The cleavage efficiency is increased when X is a lysine, a valine, an isoleucine or an alanine (Watanabe et al (1992) J Biol. Chem. 267:8270-8274).

In some embodiments, the recombinant human MIS protein comprises a modified leader sequence in place of the wild-type leader sequence of the MIS protein corresponding to amino acid residues 1-25 of SEQ ID NO:3. In some embodiments, the native leader sequence of amino acid residues 1-25 of SEQ ID NO: 3 is replaced with a non-MIS leader sequence, for example, but not limited to an albumin leader sequence, or functional fragment thereof. In some embodiments, the non-MIS leader sequence is a human serum albumin sequence (HSA), for example, a leader sequence corresponding to SEQ ID NO: 6 (i.e. amino acids 1-24 of SEQ ID NO: 4), which is encoded by nucleic acids of SEQ ID NO: 7 (i.e., nucleic acids 1-78 of SEQ ID NO: 1).

In some embodiments, a HSA sequence is a functional fragment of SEQ ID NO: 6, for example, or at least 23, or at least 22, or at least 21, or at least 20, or at least 19, or at least 18, or at least 17, or at least 16, or at least 15, or at least 14, or at least 13, or at least 12, or at least 11, or at least 10, or less than 10 consecutive or non-consecutive amino acids of SEQ ID NO:6. Modified versions of HSA leader sequence are also encompassed for use in the present invention and are disclosed in U.S. Pat. No. 5,759,802 which is incorporated herein in its entirety by reference. In some embodiments, a functional fragment of HSA leader sequence is MKWVTFISLLFLFSSAYS (SEQ ID NO: 8) or variations therefor, which are disclosed in EP patent EP2277889 which is incorporated herein in its entirety. Variants of the pre-pro region of the HSA signal sequence (e.g., MKWVTFISLLFLFSSAYSRGVFRR, SEQ ID NO: 6) include fragments, such as the pre region of the HSA signal sequence (e.g., MKWVTFISLLFLFSSAYS, SEQ ID NO:9) or variants thereof, such as, for example, MKWVSFISLLFLFSSAYS, (SEQ ID NO:10).

In some embodiments, the leader sequence is a leader sequence is at least about 60%, or at least about 70%, or at least about 80%, or at least about 90%, or at least about 95%, or at least about 96%, or at least about 97%, or at least about 98%, or at least about 99% identical to amino acid residues of SEQ ID NO: 6.

Figure 2:
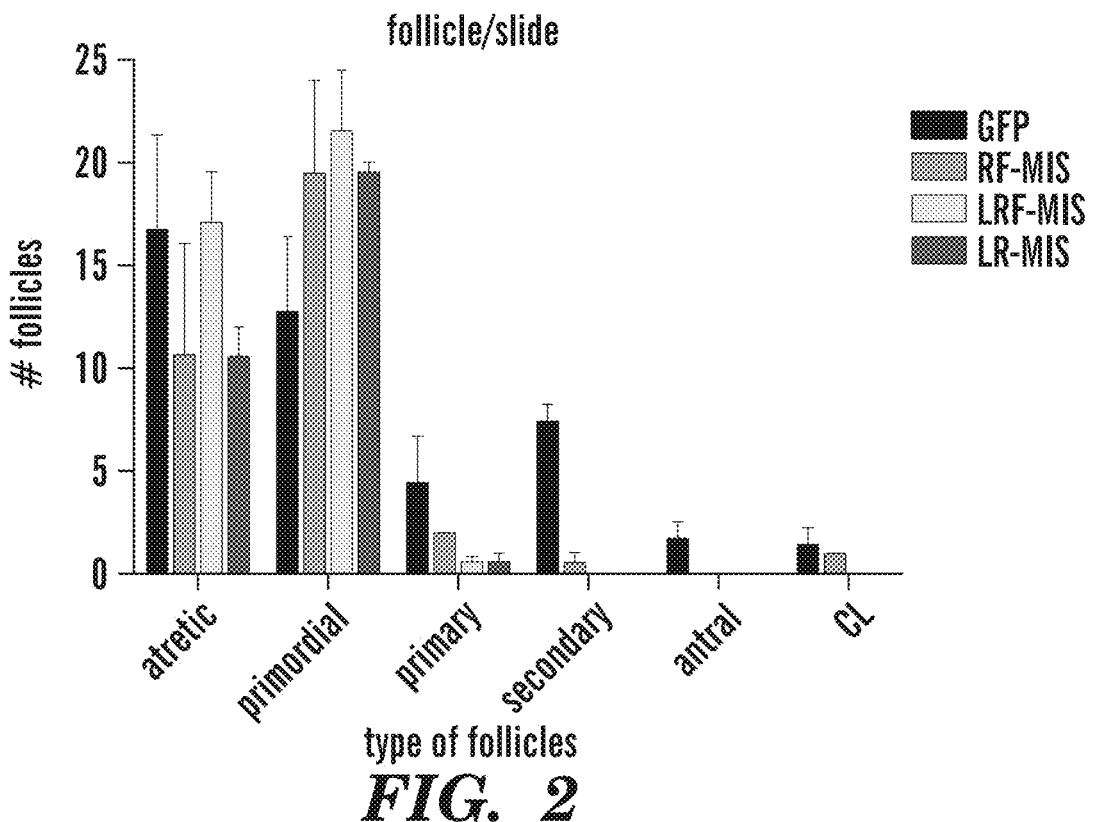
FIG. 2 shows number of follicular counts/slide following treatment with various AAV9-MIS constructs. Follicle counts in mice treated with $3 \times 10^{11}$ pfu of virus with one of the following different AAV9-MIS virus expressing human MIS variant proteins; AAV9-LR-MIS, AAV9-LRF-MIS, and AAV9-RF-MIS, for 60 days as compared to AAV9-GFP treated control mice. Mice treated with AAV9-LR-MIS, AAV9-LRF-MIS, or AAV9-RF-MIS had more follicles per slide than control AAV9-GFP treated mice, demonstrating the preservation of in the MIS-treated mice.
Figure 3:
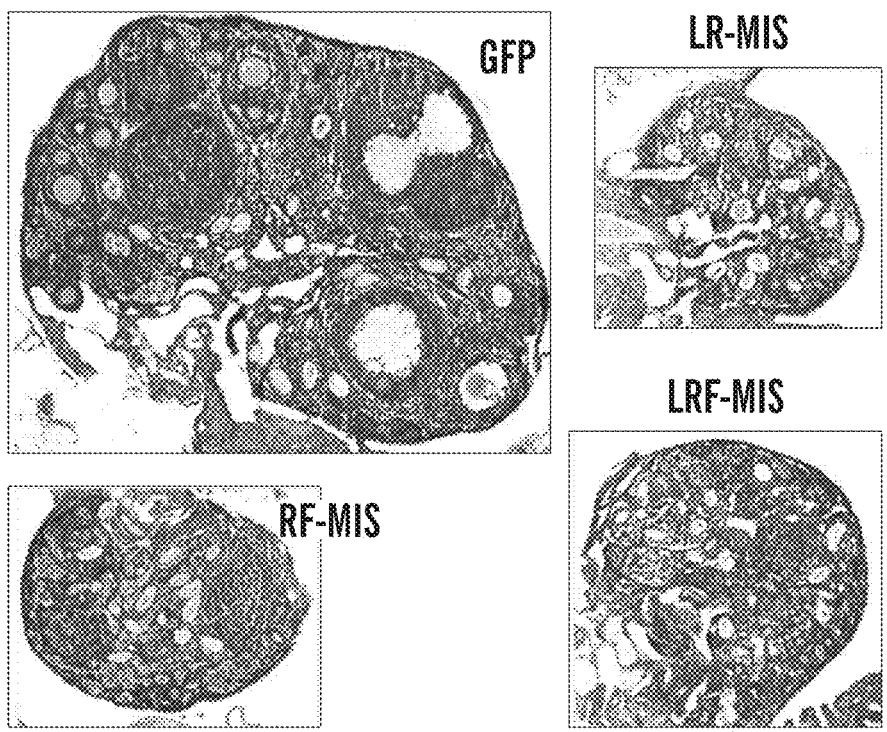
FIG. 3 is a set of images showing ovary dimensions following treatment with various AAV9-MIS constructs. Ovary sections were photographed at the largest diameter in mice treated with 3E11 virus for 60 days treated with AAV9-GFP control or three modified human MIS constructs: AAV9-LR-MIS, AAV9-LRF-MIS, and AAV9-RF-MIS. All pictures were taken at the same magnification. Mice treated with AAV9-LR-MIS, AAV9-LRF-MIS, or AAV9-RF-MIS had much smaller ovaries as compared to control AAV9-GFP treated mice, demonstrating lack of folliculogenesis in the MIS-treated mice.

The HSA leader sequence as used herein has been demonstrated to produce an unexpected increased yield (both higher concentration and higher production) of the recombinant human MIS protein (see FIGS. 2 and 3 of PCT/US14/024101). However, the presence of the HSA leader sequence also resulted in a surprising and unexpected increase in cleavage from the primary cleavage site (corresponding to cleavage at 450/451 of SEQ ID NO: 3. This increased yield and increased cleavage was surprising because with an increased yield (and therefore more protein produced by the cell), one would expect a decreased cleavage as the activity of the available cleavage enzymes becomes saturated and overextended. However, this was not the case—in fact the exact opposite occurred where with increased protein production there was increased cleavage from the primary cleavage site.

Other leader sequences are encompassed for use in a recombinant human MIS protein as disclosed herein, e.g., to replace amino acids 1-25 of SEQ ID NO: 3. Such leader sequences are well known in the art, and include the leader sequences comprising an immunoglobulin signal peptide fused to a tissue-type plasminogen activator propeptide (IgSP-tPA), as disclosed in US 2007/0141666, which is incorporated herein in its entirety by reference. Numerous other signal peptides are used for production of secreted proteins. One of them is a murine immunoglobulin signal peptide (IgSP, EMBL Accession No. M13331). IgSP was first identified in 1983 by Loh et al. (Cell. 33:85-93). IgSP is known to give a good expression in mammalian cells. For example. EP patent No. 0382762 discloses a method of producing horseradish peroxidase by constructing a fusion polypeptide between IgSP and horseradish peroxidase.

Other leader sequences include, for example, but not limited to, the MPIF-1 signal sequence (e.g., amino acids 1-21 of GenBank Accession number AAB51134) MKVSVAALSCLMLVTALGSQA (SEQ ID NO: 11); the stanniocalcin signal sequence (MLQNSAVLLLLVISASA, SEQ ID NO:12); the invertase signal sequence (e.g., MLLQAFLFLLAGFAAKISA, SEQ ID NO:13); the yeast mating factor alpha signal sequence (e.g., *K. lactis* killer toxin leader sequence); a hybrid signal sequence (e.g., MKWVSFISLLFLFSSAYSRSLEKR, SEQ ID NO:14); an HSA/MFa-1 hybrid signal sequence (also known as HSA/kex2) (e.g., MKWVSFISLLFLFSSAYSRSLDKR, SEQ ID NO:15); a *K. lactis* killer/MFα-1 fusion leader sequence (e.g., MNIFYIFLFLLSFVQGSLDKR, SEQ ID NO:16); the Immunoglobulin Ig signal sequence (e.g., MGWSCIILFL-VATATGVHS, SEQ ID NO:17); the Fibulin B precursor signal sequence (e.g., MERAAPSRRVPLPLLLLGGLAL-LAAGVDA, SEQ ID NO:18); the clusterin precursor signal sequence (e.g., MMKTLLLFVGLLLTWESGQVLG, SEQ ID NO: 19); and the insulin-like growth factor-binding protein 4 signal sequence (e.g., MLPLCLVAALL-LAAGPGPSLG, SEQ ID NO:20).

Where it is desirable to produce recombinant MIS in a bacterial system, leader sequences can include bacterial leader sequences as disclosed in US Application 2011/0020868. A number of other secretion signals have been described for use in expressing recombinant polypeptides or proteins. See, for example, U.S. Pat. Nos. 5,914,254; 4,963,495; European Patent No. 0 177 343; U.S. Pat. No. 5,082,783; PCT Publication No. WO 89/10971; U.S. Pat. Nos. 6,156,552; 6,495,357; 6,509,181; 6,524,827; 6,528,298; 6,558,939; 6,608,018; 6,617,143; 5,595,898; 5,698,435; and 6,204,023; 6,258,560; PCT Publication Nos. WO 01/21662, WO 02/068660 and U.S. Application Publication 2003/0044906; U.S. Pat. No. 5,641,671; and European Patent No. EP 0 121 352, which are incorporated herein in their entirety by reference.

In further embodiments, a MIS protein or a nucleic acid sequence encoding the same for use in the method, compositions and kits as disclosed herein also comprises a tag to aid purification. Tags are well know in the art and disclosed in PCT application PCT/US14/024010, which is incorporated herein in its entirety by reference. Protein tags are useful to aid the purification of the C-terminal domain without the need for complicated methods using wheat-germ lectin affinity or size chromatography columns. The inventors also previously added a tag (e.g., a Flag tag) at the N-terminus of the C-terminal domain, to produce a "LRF-MIS" variant corresponding to SEQ ID NO: 5. Any protein tag is encompassed for use herein, and are disclosed in PCT/US14/024010, which is incorporated herein in its entirety by reference.

In some embodiments, a recombinant MIS protein comprises at least one internal label or "tag". In some embodiments the tag can be, for example, a c-myc, poly histidine, or FLAG tag. In some embodiments, the tag is a FLAG tag, for example, a FLAG tag of SEQ ID NO:21. A FLAG tag can be encoded by the nucleic acid of SEQ ID NO: 22.

In some embodiments, the tag on the recombinant human MIS protein is internal at the carboxy terminus immediately downstream from the cleavage site. As it is the most flexible part of the C-terminus and not involved in binding to receptor and rendering specificity, as are the "fingertips" of the C-terminus (Papakostas et al, 2010, Lorenzo et al, 2002). In some embodiments, the labeling at this site is most likely to preserve biologic activity. In some embodiments, a tag, e.g., a FLAG tag is located after the primary cleavage site, e.g., after amino acid residue 450 of SEQ ID NO: 3 (corresponding to amino acid residue 425 of conventional protein nomenclature). In some embodiments, a tag is located between amino acid residues 452 and 453 of SEQ ID NO: 3 (which corresponds with amino acid residues 427 and 428 under normal amino acid nomenclature of MIS protein).

In alternative embodiments, the tag or label is located at any position between sequence 450 and 560 of SEQ ID NO: 3. In some embodiments, the tag is inserted 2 amino acid residues after the modified amino acid at position 450 of SEQ ID NO: 3. However, a position of the tag at the N-terminus of the C-terminal domain of MIS is preferred, as it location at the C-terminus of the C-terminal domain renders the C-terminal domain totally inactive, significantly reducing the bioactivity of the MIS protein.

In some embodiments, a recombinant MIS protein comprises more than one tag, e.g., for example, at least 2 or at least 3, or at least 4 or more than 4 tags. In some embodiments, the tags are sequential (e.g., one after another) and in some embodiments, they are dispersed (e.g., intermittent) in the recombinant human MIS protein. Preferably, the tags do not interfere or substantially affect the bioactivity of the recombinant MIS protein function at binding and activating MISRII. In some embodiments, where the recombinant MIS protein comprises more than one tag, the tags are the same tag. In alternative embodiments, where the recombinant MIS protein comprises more than one tag, the tags are different tags, for example, a recombinant MIS protein can comprise a FLAG tag and a histidine tag. The small size of the Flag tag allows it to be contained in the flexible, non binding N-terminal domain of the C-terminus. Accordingly, in some embodiments, any tag known to a person of ordinary skill in the art can be used in place of the Flag Tag, for example a tag of between about 5-10 amino acids, or between about 10-15 amino acids, or a tag between about 15-20 amino acids, or a tag between 20-30 amino acids, or a tag between about 30-50 amino acids. In some embodiments, a tag greater than 50 amino acids in length is not recommended, as the tag may sterically hinder the flexible N-terminus of the C-terminal domain, and thus inhibit the bioactivity of the recombinant MIS protein.

In some embodiments, a tag-labeled, e.g., FLAG tagged recombinant human MIS protein, such as the LRF recombinant human MIS protein as disclosed herein can be eluted by a single step to produce highly purified efficiently cleaved preparation with full bioactivity. When scaled-up, this purification of recombinant human MIS protein will be suitable for clinical applications; furthermore it will be useful for various binding assays in both clinical and experimental settings. Internal labeling of MIS during translation has proved to be more effective than labeling after purification of the protein as iodination or biotinylation greatly reduced MIS bioactivity. Surprisingly, the inventors have discovered that the LRF recombinant human MIS protein construct is more bioactive than the wild-type MIS. Inserting the FLAG tag sequence has several other distinct advantages. First, its unique amino acid domain is not present in any other gene (except for mouse brain phosphatase), thus making the anti-FLAG antibody very specific. Second, the elution of the protein with the 3× FLAG peptide is specific for the FLAG MIS and not other proteins that bind non-specifically to the agarose beads.

In some embodiments, a labeled recombinant human MIS protein, e.g., a MIS with an internal FLAG is useful in an efficient method for producing a highly pure and biologically active internally labeled form of MIS, which can be used for scale-up for preclinical and clinical use, for the study of MIS binding proteins and for tracking in pharmacokinetic studies.

As discussed above, MIS proteins useful in the methods as disclosed herein can be wild-type MIS, or MIS variants, such as LR-MIS, LRF-MIS and the like. Such LR-MIS and LRF-MIS protein variants are non-naturally occurring proteins and produced by recombinant means, e.g., by expression from a nucleic acid in vitro expression system as disclosed herein.

Variants and Homologues of a Human Recombinant MIS Protein.

In some embodiments, a recombinant human MIS protein useful in the methods, compositions and kits as disclosed can have a modification in the core MIS protein sequence, e.g., amino acids residues 26-560 of SEQ ID NO: 3 (including a modification of amino acid residue 450 from Q to R of SEQ ID NO: 3) and/or the insertion of a tag at the beginning of the C-terminal domain). Such variants are considered to be homologous to wild-type MIS protein.

As used herein, the term "polypeptide" refers to a polymer of amino acids and its equivalent and does not refer to a specific length of the product; thus, peptides, oligopeptides and proteins are included within the definition of a polypeptide. A derivative is a polypeptide having conservative amino acid substitutions, as compared with another sequence. Derivatives further include other modifications of proteins, including, for example, modifications such as glycosylations, acetylations, phosphorylations, and the like.

In some embodiments, a recombinant human MIS protein is at least 75%, at least 80%, at least 85%, at least 90% or at least 95% similar to the homologous recombinant human MIS protein. As used herein, "similarity" or "percent similarity" in the context of two or polypeptide sequences, refer to two or more sequences or subsequences that are the same or have a specified percentage of amino acid residues or conservative substitutions thereof, that are the same, when compared and aligned for maximum correspondence, as measured using one of the following sequence comparison algorithms, or by visual inspection. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art, as discussed below.

Homologues and functional derivatives and functional fragments of MIS of SEQ ID NO: 1 are also encompassed for use in the present invention, and can also be identified, for example, by expression of MIS from an expression library. (See, e.g., Sambrook et al. (2001). Molecular cloning: a laboratory manual, 3rd ed. (Cold Spring Harbor, N.Y., Cold Spring Harbor Laboratory Press); Ausubel et al., supra.) A mutated endogenous gene sequence can be referred to as a heterologous transgene; for example, a transgene encoding a mutation in MIS which is not known in naturally-occurring genomes is a heterologous transgene with respect to murine and non-murine, e.g., human species. A MIS protein, such as, for example, those disclosed in U.S. Pat. Nos. 5,427,780, 5,359,033 and 5,661,126 (the disclosures of which are incorporated by reference herein).

The variation in primary structure of core human MIS protein sequence (e.g., amino acids residues 26-560 of SEQ ID NO: 3 (including a modification of amino acid residue 450 from Q to R of SEQ ID NO: 3) and/or the insertion of a tag at the beginning of the N-terminal domain of the C-terminal domain), or functional fragment, or a homologue are encompassed for use in the present invention, for instance, may include deletions, additions and substitutions. The substitutions may be conservative or non-conservative. The differences between a recombinant human MIS protein and a variant generally conserve desired properties, mitigate or eliminate undesired properties and add desired or new properties. For example, variants of a recombinant human MIS protein can have superior activity as compared to wild-type MIS protein.

It will be appreciated by those of skill that the core human MIS protein sequence (e.g., amino acids residues 26-560 of SEQ ID NO: 3) of a recombinant human MIS protein as disclosed herein can be readily manipulated to alter the amino acid sequence of a protein. A gene encoding the MIS protein or a functional fragment, homologue or variant thereof, can be manipulated by a variety of well known techniques for in vitro mutagenesis, among others, to produce variants of the naturally occurring human protein or fragment thereof, herein referred to as variants or muteins, may be used in accordance with the invention.

Other Modifications to a Recombinant Human MIS Protein

The recombinant human MIS protein useful in the present invention can also be modified at their amino termini, for example, so as to increase their hydrophilicity. Increased hydrophobicity enhances exposure of the peptides on the surfaces of lipid-based carriers into which the parent peptide-lipid conjugates have been incorporated. Polar groups suitable for attachment to peptides so as to increase their hydrophilicity are well known, and include, for example and without limitation: acetyl ("Ac"), 3-cyclohexylalanyl ("Cha"), acetyl-serine ("Ac Ser"), acetyl-seryl-serine ("Ac-Ser-Ser-"), succinyl ("Suc"), succinyl-serine ("Suc-Ser"), succinyl-seryl-serine ("Suc-Ser-Ser"), methoxy succinyl ("MeO-Suc"), methoxy succinyl-serine ("MeO-Suc-Ser"), methoxy succinyl-seryl-serine ("MeO-Suc-Ser-Ser") and seryl-serine ("Ser-Ser-") groups, polyethylene glycol ("PEG"), polyacrylamide, polyacrylomorpholine, polyvinylpyrrolidine, a polyhydroxyl group and carboxy sugars, e.g., lactobionic, N-acetyl neuraminic and sialic acids, groups. The carboxy groups of these sugars would be linked to the N-terminus of the peptide via an amide linkage. Presently, the preferred N-terminal modification is a methoxy-succinyl modification.

In some embodiments, a recombinant human MIS protein can be fused to one or more fusion partners. In certain embodiments, one of the fusion partners is the Fc protein (e.g., mouse Fc or human Fc). The fusion protein may further include a second fusion partner such as a purification or detection tag, for example, proteins that may be detected directly or indirectly such as green fluorescent protein, hemagglutinin, or alkaline phosphatase), DNA binding domains (for example, GAL4 or LexA), gene activation domains (for example, GAL4 or VP16), purification tags, or secretion signal peptides (e.g., preprotryypsin signal sequence).

In one embodiment, a recombinant human MIS protein fusion protein useful in the methods and compositions as disclosed herein can comprise a human Fc protein or a functional fragment thereof. Accordingly, in one embodiment, a recombinant human MIS protein fusion protein useful in the methods and compositions as disclosed herein can comprises a human Fc molecule as the first fusion partner, where the Fc fragment can be SEQ ID NO: 23 or functional variants or functional derivatives thereof, where SEQ ID NO: 23 is as follows:

```
LELVPRGSGDPIEGRGGGGGDPKSCDKPHTCPLCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSRDELTKNQVSLTCLVKGFYPSDIAVEWESNGQPENNYKATP

PVLDSDGSFFLYSKLTVDKSRWQQGNVFSCSVMHEALHNHYTQKSLSLSP

GK
```

Variations and modifications to a recombinant human MIS protein and vectors can be used to increase or decrease recombinant human MIS protein expression, and to provide means for targeting. For example, a recombinant human MIS protein can be linked with a molecular targeting molecule for targeting cancer cells or ovarian cells, to make the recombinant human MIS protein specific for cancers or tissue specific to the ovary, respectively.

In one embodiment, a recombinant human MIS protein is fused to a second fusion partner, such as a carrier molecule to enhance its bioavailability. Such carriers are known in the art and include poly (alkyl) glycol such as poly ethylene glycol (PEG). Fusion to serum albumin can also increase the serum half-life of therapeutic polypeptides.

In some embodiments, a recombinant human MIS protein can also be fused to a second fusion partner, for example, to a polypeptide that targets the product to a desired location, or, for example, a tag that facilitates its purification, if so desired. In some embodiments, tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use.

In some embodiments, a recombinant human MIS protein or functional fragment thereof is modified to achieve adequate circulating half-lives, which impact dosing, drug administration and efficacy. Many approaches have been undertaken with the aim to increase the half-life of biotherapeutics. Small proteins below 60 kD are cleared rapidly by the kidney and therefore do not reach their target. This means that high doses are needed to reach efficacy. The modifications to a recombinant human MIS protein and fragments encompassed in the methods of the present invention to increase the half-life of proteins in circulation include: PEGylation; conjugation or genetic fusion with proteins, e.g., transferrin (WO06096515A2), albumin, growth hormone (US2003104578AA); conjugation with cellulose (Levy and Shoseyov, 2002); conjugation or fusion with Fc fragments; glycosylation and mutagenesis approaches (Carter, 2006), which are incorporated herein by reference.

In the case of PEGylation, polyethylene glycol (PEG) is conjugated to a recombinant human MIS protein or fragment, which can be for example a plasma protein, antibody or antibody fragment. The first studies regarding the effect of PEGylation of antibodies were performed in the 1980s. The conjugation can be done either enzymatically or chemically and is well established in the art (Chapman, 2002; Veronese and Pasut, 2005). With PEGylation the total size can be increased, which reduces the chance of renal filtration. PEGylation further protects from proteolytic degradation and slows the clearance from the blood. Further, it has been reported that PEGylation can reduce immunogenicity and increase solubility. The improved pharmacokinetics by the addition of PEG is due to several different mechanisms: increase in size of the molecule, protection from proteolysis, reduced antigenicity, and the masking of specific sequences from cellular receptors. In the case of antibody fragments (Fab), a 20-fold increase in plasma half-life has been achieved by PEGylation (Chapman, 2002).

To date there are several approved PEGylated drugs, e.g., PEG-interferon alpha2b (PEG-INTRON) marketed in 2000 and alpha2a (Pegasys) marketed in 2002. A PEGylated antibody fragment against TNF alpha, called Cimzia or Certolizumab Pegol, was filed for FDA approval for the treatment of Crohn's disease in 2007 and has been approved on Apr. 22, 2008. A limitation of PEGylation is the difficulty in synthesizing long monodisperse species, especially when PEG chains over 1000 kD are needed. For many applications, polydisperse PEG with a chain length over 10000 kD is used, resulting in a population of conjugates having different length PEG chains, which need extensive analytics to ensure equivalent batches between productions. The different length of the PEG chains may result in different biological activities and therefore different pharmacokinetics. Another limitation of PEGylation is a decrease in affinity or activity as it has been observed with alpha-interferon Pegasys, which has only 7% of the antiviral activity of the native protein, but has improved pharmacokinetics due to the enhanced plasma half-life.

In some embodiments, a recombinant human MIS protein or fragment thereof is conjugated with a long lived protein, e.g. albumin, which is 67 kD and has plasma half-life of 19 days in human (Dennis et al., 2002). Albumin is the most abundant protein in plasma and is involved in plasma pH regulation, but also serves as a carrier of substances in plasma. In the case of CD4, increased plasma half-life has been achieved after fusing it to human serum albumin (Yeh et al., 1992). Other examples for fusion proteins are insulin, human growth hormone, transferrin and cytokines (Ali et al., 1999; Duttaroy et al., 2005; Melder et al., 2005; Osborn et al., 2002a; Osborn et al., 2002b; Sung et al., 2003) and see (US2003104578A1, WO06096515A2, and WO07047504A2, herein incorporated in entirety by reference).

The effect of glycosylation on plasma half-life and protein activity has also been extensively studied. In the case of tissue plasminogen activator (tPA) the addition of new glycosylation sites decreased the plasma clearance, and improved the potency (Keyt et al., 1994). Glycoengineering has been successfully applied for a number of recombinant proteins and immunoglobulins (Elliott et al., 2003; Raju and Scallon, 2007; Sinclair and Elliott, 2005; Umana et al., 1999). Further, glycosylation influences the stability of immunoglobulins (Mimura et al., 2000; Raju and Scallon, 2006).

In some embodiments, a recombinant human MIS protein or fragments thereof can be fused to the Fc fragment of an IgG (Ashkenazi and Chamow, 1997). The Fc fusion approach has been utilized, for example in the Trap Technology developed by Regeneron (e.g. IL1 trap and VEGF trap). The use of albumin to extend the half-life of peptides has been described in US2004001827A1. Positive effects of albumin have also been reported for Fab fragments and scFv-HSA fusion protein (Smith et al., 2001). It has been demonstrated that the prolonged serum half-life of albumin is due to a recycling process mediated by the FcRn (Anderson et al., 2006; Chaudhury et al., 2003; Smith et al., 2001).

In some embodiments, a recombinant human MIS protein is conjugated to a biotinylated Fc protein, as disclosed in US application 2010/0209424, which is incorporated herein in its entirety by reference.

As used herein, the term "conjugate" or "conjugation" refers to the attachment of two or more entities to form one entity. For example, the methods of the present invention provide conjugation of a recombinant human MIS protein (i.e. SEQ ID NO: 2 or 3 or fragments or derivatives or variants thereof) joined with another entity, for example a moiety such as a first fusion partner that makes the recombinant human MIS protein stable, such as Ig carrier particle, for example IgG1 Fc. The attachment can be by means of linkers, chemical modification, peptide linkers, chemical linkers, covalent or non-covalent bonds, or protein fusion or by any means known to one skilled in the art. The joining can be permanent or reversible. In some embodiments, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention.

According to the present invention, a recombinant human MIS protein (i.e. SEQ ID NO: 4 or 5 or fragments, derivatives or variants thereof), can be linked to the first fusion partner via any suitable means, as known in the art, see for example U.S. Pat. Nos. 4,625,014, 5,057,301 and 5,514,363, which are incorporated herein in their entirety by reference. For example, a recombinant human MIS protein can be covalently conjugated to the IgG1 Fc, either directly or through one or more linkers. In one embodiment, a recombinant human MIS protein as disclosed herein is conjugated directly to the first fusion partner (e.g. Fc), and in an alternative embodiment, a recombinant human MIS protein as disclosed herein can be conjugated to a first fusion partner (such as IgG1 Fc) via a linker, e.g. a transport enhancing linker.

A large variety of methods for conjugation of a recombinant human MIS protein as disclosed herein with a first fusion partner (e.g. Fc) are known in the art. Such methods are e.g. described by Hermanson (1996, Bioconjugate Techniques, Academic Press), in U.S. Pat. Nos. 6,180,084 and 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, N.Y.). It is recognized that, in some cases, a recombinant human MIS protein can lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the entities, such as a recombinant human MIS protein to be conjugated.

Suitable methods for conjugation of a recombinant human MIS protein as disclosed herein with a first fusion partner (e.g. Fc) include e.g. carbodimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate a recombinant human MIS protein as disclosed herein with a first fusion partner (e.g. Fc), for example but not limited to aminocaproic horse radish peroxidase (HRP) or a heterobiofunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homobiofunctional cross-linkers. Such multi-step protocols can offer a great control of conjugate size and the molar ratio of components.

The term "linker" refers to any means to join two or more entities, for example a recombinant human MIS protein as disclosed herein with a first fusion partner (e.g. Fc). A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the effector molecule and/or the probe can be modified by oxidation, hydroxylation, substitution, reduction etc. to provide a site for coupling. It will be appreciated that modification which do not significantly decrease the function of a recombinant human MIS protein as disclosed herein or the first fusion partner (e.g. Fc) are preferred.

Targeting. In some embodiments, a recombinant human MIS protein, or functional fragment, or a homologue for use in the methods and compositions as disclosed herein can be targeted to a cancer or ovarian cells via a targeting ligand. A targeting ligand is a molecule, e.g., small molecule, protein or fragment thereof that specifically binds with high affinity to a target, e.g., a cell-surface marker on a pre-selected cell, such as a surface protein such as a receptor that is present to a greater degree on the pre-selected cell target than on any other body tissue. Accordingly, in some embodiments, a recombinant human MIS protein for use in the compositions and methods as disclosed herein can be fused to a Fc and/or optionally also to a targeting molecule. In some embodiments, a nucleic acid encoding a targeting ligand can be fused to a nucleotide encoding a recombinant human MIS protein or fragment or homologue or variant thereof. Another example of a targeting ligand is a group of cadherin domains from a human cadherin. A targeting ligand component attached to a recombinant human MIS protein can include a naturally occurring or recombinant or engineered ligand, or a fragment thereof, capable of binding the pre-selected target cell.

Further examples of targeting ligands also include, but are not limited to, antibodies and portions thereof that specifically bind a pre-selected cell surface protein with high affinity. By "high affinity" is meant an equilibrium dissociation constant of at least molar, as determined by assay methods known in the art, for example, BiaCore analysis. In one embodiment, the targeting ligand may also comprise one or more immunoglobulin binding domains isolated from antibodies generated against a selected tissue-specific surface protein or target tissue-specific receptor. The term "immunoglobulin or antibody" as used herein refers to a mammalian, including human, polypeptide comprising a framework region from an immunoglobulin gene or fragments thereof that specifically binds and recognizes an antigen, which, in the case of the present invention, is a tissue-specific surface protein, a target tissue-specific receptor, or portion thereof. If the intended targeting fusion polypeptide will be used as a mammalian therapeutic, immunoglobulin binding regions should be derived from the corresponding mammalian immunoglobulins. If the targeting fusion polypeptide is intended for non-therapeutic use, such as for diagnostics and ELISAs, the immunoglobulin binding regions may be derived from either human or non-human mammals, such as mice. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, lgG, lgM, IgA, IgD, and IgE, respectively. Within each lgG class, there are different isotypes (e.g. lgG1, lgG2, etc.). Typically, the antigen-binding region of an antibody will be the most critical in determining specificity and affinity of binding.

An exemplary immunoglobulin (antibody) structural unit of human lgG, comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" (VL) and variable heavy chain (VH) refer to these light and heavy chains respectively. Antibodies exist as intact immunoglobulins, or as a number of well-characterized fragments produced by digestion with various peptidases. For example, pepsin digests an antibody below the disulfide linkages in the hinge region to produce F(ab)'2, a dimer of Fab which itself is a light chain joined to VH-CH by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms immunoglobulin or antibody, as used herein, also includes antibody fragments either produced by the modification of whole antibodies, or those synthesized de novo using recombinant DNA methodologies (e.g., single chain Fv)(scFv)) or those identified using phase display libraries (see, for example, McCafferty et al. (1990) Nature 348:552-554). In addition, the fusion polypeptides of the invention include the variable regions of the heavy (VH) or the light (VL) chains of immunoglobulins, as well as tissue-specific surface protein and target receptor-binding portions thereof. Methods for producing such variable regions are described in Reiter, et al. (1999) J. Mol. Biol. 290:685-698.

Methods for preparing antibodies are known to the art. See, for example, Kohler & Milstein (1975) Nature 256: 495-497; Harlow & Lane (1988) Antibodies: a Laboratory Manual, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the fusion polypeptides and methods of the instant invention. Also, transgenic mice, or other organisms such as other mammals, may be used to express human or humanized antibodies. Alternatively phage display technology can be used to identify antibodies, antibody fragments, such as variable domains, and heteromeric Fab fragments that specifically bind to selected antigens.

Screening and selection of preferred immunoglobulins (e.g., antibodies) can be conducted by a variety of methods known to the art: Initial screening for the presence of monoclonal antibodies specific to a tissue-specific or target receptor may be conducted through the use of ELISA-based methods or phage display, for example. A secondary screen is preferably conducted to identify and select a desired monoclonal antibody for use in construction of the tissue-specific fusion polypeptides of the invention. Secondary screening may be conducted with any suitable method known to the art. One method, termed "Biosensor Modification-Assisted Profiling" ("BiaMAP") (US patent publication 2004/101920), allows rapid identification of hybridoma clones producing monoclonal antibodies with desired characteristics. More specifically, monoclonal antibodies are sorted into distinct epitope-related groups based on evaluation of antibody: antigen interactions.

Production of Recombinant Human MIS Proteins

Recombinant human MIS proteins, such as LR-MIS etc., useful in the methods, composition and kits as disclosed herein can be obtained by any suitable method. For example, polypeptides can be produced using conventional recombinant nucleic acid technology such as DNA or RNA, preferably DNA. Guidance and information concerning methods and materials for production of polypeptides using recombinant DNA technology can be found in numerous treatises and reference manuals. See, e.g., Sambrook et al, 1989, Molecular Cloning—A Laboratory Manual, 2nd Ed., Cold Spring Harbor Press; Ausubel et al. (eds.), 1994, Current Protocols in Molecular Biology, John Wiley & Sons, Inc.; Innis et al. (eds.), 1990 PCR Protocols, Academic Press.

Alternatively, recombinant human MIS proteins, such as LR-MIS etc., or functional fragments thereof can be obtained directly by chemical synthesis, e.g., using a commercial peptide synthesizer according to vendor's instructions. Methods and materials for chemical synthesis of polypeptides are well known in the art. See, e.g., Merrifield, 1963, "Solid Phase Synthesis," J. Am. Chem. Soc. 83:2149-2154.

In some embodiments, a recombinant human MIS protein, or functional fragment or derivative or variant thereof can be expressed in the cell following introduction of a DNA encoding the protein, e.g., a nucleic acid encoding recombinant human MIS proteins or homologues or functional derivatives thereof, e.g., in a conventional expression vector as disclosed herein or by a catheter or by cells transformed with the nucleic acid ex vivo and transplanted into the subject.

Delivery of Human Recombinant MIS Proteins Via Gene Therapy:

Accordingly, in one aspect, the present invention relates to a method of contraception or preventing pregnancy in a female subject, the method comprising administering to the female subject a composition comprising a nucleic acid encoding a MIS protein or MIS variant protein. Another aspect relates to a method of preserving ovarian reserve in a female subject, the method comprising administering to the female subject a composition comprising a nucleic acid encoding a MIS protein or MIS variant protein.

In some embodiments, a composition comprising a nucleic acid encoding a MIS protein or MIS variant protein is administered in a method for permanent contraception, e.g., for the treatment of animals such as cats and dogs, and other animals where control of their population is desired.

Accordingly, in some embodiments, the MIS protein or MIS variant protein is expressed from a vector, wherein the vector comprises a polynucleotide which encodes a recombinant MIS protein of SEQ ID NO: 3, or SEQ ID NO: 4 or SEQ ID NO: 5. In some embodiments, the MIS protein expressed is encoded by a polynucleotide which of SEQ ID NO: 1 to produce a MIS protein which comprises substantially the same amino acid sequence as a wild type MIS protein produced in the subject. In some embodiments, the MIS protein is encoded by a polynucleotide that produces a protein which has an amino acid sequence that is at least 90%, at least 91%, at least 92%, at least 93%, at least 94%, at least 95%, at least 96%, at least 97%, at least 98%, at least 99% identical to the amino acid sequence of SEQ ID NO: 3, or SEQ ID NO: 4 or SEQ ID NO: 5 or a functional fragment thereof.

In some embodiments, the vector expressing a MIS protein comprises a polynucleotide sequence which corresponds to SEQ ID NO: 1 or a polynucleotide which has at least 95% sequence identity to the nucleic acid sequence of SEQ ID NO: 1.

In some embodiments, the vector expressing a MIS protein comprises a polynucleotide sequence which corresponds to SEQ ID NO: 2 or a polynucleotide which has at least 95% sequence identity to the nucleic acid sequence of SEQ ID NO: 2.

A variety of vectors that comprise a polynucleotide encoding a recombinant MIS protein can be encompassed for in the methods of the present invention. For example, a number of such vectors were disclosed in U.S. 61/777,135, filed on Mar. 12, 2013, U.S. 61/880,451, filed on Sep. 20, 2013, and U.S. 61/881,719, filed on Sep. 24, 2013, the content of each of which is incorporated by reference for its entirety.

In some embodiments, the vector is an expression vector. Expression vectors compatible with eukaryotic cells, preferably those compatible with vertebrate cells, can be used to produce recombinant constructs for the expression of a recombinant MIS protein or a functional derivative or functional variant or functional fragment thereof as disclosed herein. Eukaryotic cell expression vectors are well known in the art and are available from several commercial sources.

Alternatively, in some embodiments, a plasmid expression vector can be used. Plasmid expression vectors include, but are not limited to, pcDNA3.1, pET vectors (Novagen 0), pGEX vectors (GE Life Sciences), and pMAL vectors (New England labs. Inc.) for protein expression in *E. coli* host cell such as BL21, BL21(DE3) and AD494(DE3)pLysS, Rosetta (DE3), and Origami(DE3) (Novagen®); the strong CMV promoter-based pcDNA3.1 (Invitrogen™ Inc.) and pCIneo vectors (Promega) for expression in mammalian cell lines such as CHO, COS, HEK-293, Jurkat, and MCF-7; replication incompetent adenoviral vector vectors pAdeno X, pAd5F35, pLP-Adeno-X-CMV (Clontech®), pAd/CMV/V5-DEST, pAd-DEST vector (Invitrogen™ Inc.) for adenovirus-mediated gene transfer and expression in mammalian cells; pLNCX2, pLXSN, and pLAPSN retrovirus vectors for use with the Retro-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN™ Inc.) for lentivirus-mediated gene transfer and expression in mammalian cells; adenovirus-associated virus expression vectors such as pAAV-MCS, pAAV-IRES-hrGFP, and pAAV-RC vector (Stratagene®) for adeno-associated virus-mediated gene transfer and expression in mammalian cells; BACpak6 baculovirus (Clontech®) and pFastBac™ HT (Invitrogen™ Inc.) for the expression in *Spodopera frugiperda* 9 (Sf9) and Sf11 insect cell lines; pMT/BiP/V5-His (Invitrogen™ Inc.) for the expression in *Drosophila* Schneider S2 cells; Pichia expression vectors pPICZa, pPICZ, pFLDa and pFLD (Invitrogen™ Inc.) for expression in *Pichia pastoris* and vectors pMETa and pMET for expression in *P. methanolica*; pYES2/GS and pYD1 (Invitrogen™ Inc.) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confer resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination.

In some embodiments, the expression vector is pcDNA 3.1 or cDNA or genome vector for bacteria (e.g., *e coli*) or bacteriophage.

In some embodiments, a nucleic acid encoding a recombinant human MIS protein, or MIS variant protein (e.g., LR-MIS) or functional fragment thereof as disclosed herein, can be suitably administered as a vector, e.g., a viral vector. In some embodiments, the expression vector is a viral vector. In some embodiments, the viral vector can be an adenoviral vector, a poxvirus vector, or a lentiviral vector. Other viral vectors include, for example, adenovirus, adeno-associated virus, pox virus such as an orthopox (vaccinia and attenuated vaccinia), avipox, lentivirus, murine moloney leukemia virus, etc.

In some embodiments, the viral vector is an adeno-associated virus (AAV). In particular, the inventors have demonstrated herein that the expression level of MIS protein by an AAV9 vector comprising an AAV-MIS construct was high and sustained for the 60 day length of the experiment (FIG. 1A). Accordingly, in some embodiments, the method described herein can permit permanent contraception in the subject after a single injection, wherein the composition administered to the subject can sustain the expression of MIS equal to or above a threshold level. The threshold level is the minimal level of MIS that is needed to achieve a complete block in folliculogenesis in the subject. It should be noted that the threshold level can depend on the subject or the species of the subject. There are a variety of practical situations where permanent contraception is desired, for example, in veterinary applications.

Recently, AAVs, which normally infect mammals, including humans, but are non-pathogenic, have been developed and employed as gene therapy vectors in clinical trials in the United States and Europe (Daya and Berns, Clinical Microbiology Reviews 2008, 21, 583-593). In some embodiments, the AAV is AAV9.

In some embodiments, a nucleic acid encoding a recombinant human MIS protein, or MIS variant protein (e.g., LR-MIS) can be effectively used in treatment by gene therapy. See, generally, for example, U.S. Pat. No. 5,399,346, which is incorporated herein by reference. The general principle is to introduce the polynucleotide into a target cell in a patient, and where it is transcribed into the protein.

Entry into the cell can be facilitated by suitable techniques known in the art such as providing the polynucleotide in the form of a suitable vector, or encapsulation of the polynucleotide in a liposome.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in liver, neuronal, bone, muscle, skin, joint, or cartilage cells, or a heterologous promoter that can be induced by a suitable agent.

Viral vector systems which can be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. In a preferred embodiment, the vector is an adenovirus. Replication-defective viruses can also be advantageous.

The vector may or may not be incorporated into the cells genome. The constructs may include viral sequences for transfection, if desired. Alternatively, the construct may be incorporated into vectors capable of episomal replication, e.g., EPV and EBV vectors.

Constructs for the expression of a nucleic acid encoding a recombinant human MIS protein, or MIS variant protein (e.g., LR-MIS) as disclosed herein., e.g., DNA, MOD-RNA or RNAa, can generally be operatively linked to regulatory elements, e.g., promoters, enhancers, etc., to ensure the expression of the construct in target cells. Other specifics for vectors and constructs are described in further detail below.

In some embodiments, the inducible vector comprises pcDNA 3.1 or cDNA or genome vector for bacteria (e.g., *e coli*) or bacteriophage.

In some embodiments, the inducible vector comprises a viral vector.

In some embodiments of compositions being administered that comprises an inducible vector, the number of primordial follicles being recruited can be reverted to a normal level by inhibiting the expression of MIS. Use of inducible vectors to regulate gene expression or protein synthesis is known in the art, see for example, in WO1993022431, US20110301228, U.S. Pat. No. 6,500,647, WO2005053750, or U.S. Pat. No. 6,784,340.

In some embodiments, the MIS protein or MIS variant protein (e.g., LR-MIS protein) is expressed by an inducible vector, which can comprise one or more regulatory elements, e.g., promoters, enhancers, etc., which are operatively linked to the polynucleotide encoding a recombinant MIS protein, whereby the regulatory elements can control the expression level of MIS.

Typical regulatory elements include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Included in the term "regulatory elements" are nucleic acid sequences such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc. Regulatory sequences useful in the methods as disclosed herein are promoter elements which are sufficient to render promoter-dependent gene expression controllable for cell type-specific, tissue-specific or inducible by external signals or agents (e g enhancers or repressors); such elements may be located in the 5' or 3' regions of the native gene, or within an intron.

As used herein, the term "tissue-specific promoter" means a nucleic acid sequence that serves as a promoter, i.e., regulates expression of a selected nucleic acid sequence operably linked to the promoter, and which selectively affects expression of the selected nucleic acid sequence in specific cells of a tissue, such as cells of ovarian origin.

The term "constitutively active promoter" refers to a promoter of a gene which is expressed at all times within a given cell. Exemplary promoters for use in mammalian cells include cytomegalovirus (CMV), and for use in prokaryotic cells include the bacteriophage T7 and T3 promoters, and the like.

The term "inducible promoter" refers to a promoter of a gene which can be expressed in response to a given signal, for example addition or reduction of an agent. Non-limiting examples of an inducible promoter are "tet-on" and "tet-off" promoters, or promoters that are regulated in a specific tissue type.

In a specific embodiment, viral vectors that contain nucleic acid sequences e.g., DNA, MOD-RNA or RNAa encoding a recombinant human MIS protein or functional fragment thereof as disclosed herein can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding a recombinant human MIS protein are cloned into one or more vectors, which facilitate delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

The production of a recombinant retroviral vector carrying a gene of interest is typically achieved in two stages. First, sequence encoding a recombinant human MIS protein or a functional derivative or functional variant or functional fragment thereof, alone or fused to -Fc can be inserted into a retroviral vector which contains the sequences necessary for the efficient expression of the metabolic regulators (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (−PBS), a 3' regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant retroviral vector, the vector DNA is introduced into a packaging cell line. Packaging cell lines provide viral proteins required in trans for the packaging of viral genomic RNA into viral particles having the desired host range (e.g., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permits entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Another preferred viral vector is a pox virus such as a vaccinia virus, for example an attenuated vaccinia such as Modified Virus Ankara (MVA) or NYVAC, an avipox such as fowl pox or canary pox. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In another embodiment, lentiviral vectors are used, such as the HIV based vectors described in U.S. Pat. Nos. 6,143,520; 5,665,557; and 5,981,276, which are herein incorporated by reference. In some embodiments, a viral vector such as an Adeno-associated virus (AAV) vector is used. Exemplary AAV vectors are disclosed in Walsh et al., Proc. Soc. Exp. Biol. Med. 204:289-300 (1993); U.S. Pat. No. 5,436,146 which is incorporated herein by reference; Gao et al., Gene Therapy 2005, 5, 285-297; Vandenberghe et al., Gene Therapy 2009, 16, 311-319; Gao et al., PNAS 2002, 99, 11854-11859; Gao et al., PNAS 2003, 100, 6081-6086; Gao et al., J. of Virology 2004, 78, 6381-6388; Molecular Cloning: A Laboratory Manual ($4^{th}$ edition) ed. by M. Green and J. Sambrook.

In some embodiments, the AAV vector is an AAV1, AAV2, AAV4, AAV5, AAV6, AAV7, AAV8, AAV9, AAVrh.10, AAV2.5. It should be noted that the selection of a particular type of AAV vectors can depend on the target tissue. In some embodiments, a AAV vector for expressing a MIS protein, or MIS variant protein (e.g., LR-MIS) is AAV9 as disclosed herein in the Examples.

In some embodiments, when a recombinant human MIS protein, or MIS variant protein (e.g., LR-MIS) encoded by a viral vector is expressed endogenously in a subject, the expression level of the recombinant human MIS protein disclosed herein can be constant over a desired period of time, for example, at least 1 week, at least 2 weeks, at least 3 weeks, at least 1 month, at least 2 months, at least 3 months, at least 6 months, at least 1 year, or at least 5 years. In some embodiments, the expression of the recombination human MIS protein disclosed herein can be sustained at or above a therapeutically effective dosage level over a desired period of time.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

U.S. Pat. No. 5,676,954 (which is herein incorporated by reference) reports on the injection of genetic material, complexed with cationic liposome carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals. Such cationic lipid complexes or nanoparticles can also be used to deliver protein.

A gene or nucleic acid sequence can be introduced into a target cell by any suitable method. For example, a recombinant human MIS protein construct can be introduced into a cell by transfection (e.g., calcium phosphate or DEAE-dextran mediated transfection), lipofection, electroporation, microinjection (e.g., by direct injection of naked DNA), biolistics, infection with a viral vector containing a muscle related transgene, cell fusion, chromosome-mediated gene transfer, microcell-mediated gene transfer, nuclear transfer, and the like. A nucleic acid encoding a recombinant human MIS protein can be introduced into cells by electroporation (see, e.g., Wong and Neumann, Biochem. Biophys. Res. Commun. 107:584-87 (1982)) and biolistics (e.g., a gene gun; Johnston and Tang, Methods Cell Biol. 43 Pt A:353-65 (1994); Fynan et al., Proc. Natl. Acad. Sci. USA 90:11478-82 (1993)).

In certain embodiments, a gene or nucleic acid sequence encoding a recombinant human MIS protein can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., Med. Chem. 42:4292-99 (1999); Godbey et al., Gene Ther. 6:1380-88 (1999); Kichler et al., Gene Ther. 5:855-60 (1998); Birchaa et al., J. Pharm. 183:195-207 (1999)).

Methods known in the art for the therapeutic delivery of agents such as proteins and/or nucleic acids can be used for the delivery of a polypeptide or nucleic acid encoding a recombinant human MIS protein to a subject, e.g., cellular transfection, gene therapy, direct administration with a delivery vehicle or pharmaceutically acceptable carrier, indirect delivery by providing recombinant cells comprising a nucleic acid encoding a targeting fusion polypeptide of the invention.

Various delivery systems are known and can be used to directly administer therapeutic polypeptides such as a recombinant human MIS protein and/or a nucleic acid encoding a recombinant human MIS protein as disclosed herein, e.g., encapsulation in liposomes, microparticles, microcapsules, recombinant cells capable of expressing the compound, and receptor-mediated endocytosis (see, e.g., Wu and Wu, 1987, J. Biol. Chem. 262:4429-4432). Methods of introduction can be enteral or parenteral and include but are not limited to intradermal, intramuscular, intraperitoneal, intravenous, subcutaneous, pulmonary, intranasal, intraocular, epidural, and oral routes. The agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105).

Thus, a wide variety of gene transfer/gene therapy vectors and constructs are known in the art. These vectors are readily adapted for use in the methods of the present invention. By the appropriate manipulation using recombinant DNA/molecular biology techniques to insert an operatively linked recombinant human MIS protein encoding nucleic acid segment into the selected expression/delivery vector, many equivalent vectors for the practice of the methods described herein can be generated.

It will be appreciated by those of skill that cloned genes readily can be manipulated to alter the amino acid sequence of a protein. The cloned gene for recombinant human MIS protein can be manipulated by a variety of well-known techniques for in vitro mutagenesis, among others, to produce variants of the naturally occurring human protein, herein referred to as muteins or variants or mutants of a recombinant human MIS protein, which may be used in accordance with the methods and compositions described herein.

The variation in primary structure of muteins of a recombinant human MIS protein useful in the invention, for instance, may include deletions, additions and substitutions. The substitutions may be conservative or non-conservative. The differences between the natural protein and the mutein generally conserve desired properties, mitigate or eliminate undesired properties and add desired or new properties.

Remington's Pharmaceutical sciences Ed. Germany, Merk Publishing, Easton, Pa., 1 995 (the contents of which are hereby incorporated by reference), discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; malt; gelatin; talc; excipients such as cocoa butter and: suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; water; isotonic saline; Ringer's solution, ethyl alcohol, and phosphate buffer solutions, as well as other non-toxic compatible lubricants such as sodium lauryl sulfate and magnesium sulfate, as well as coloring agents, releasing agents, coating agents, sweetening, flavoring and perfuming agents, preservatives and antioxidants can also be present in the composition, according to the judgment of the formulator.

In some embodiments, the composition described herein further comprises a pharmaceutically acceptable carrier. A variety of means for administering the composition described herein to subjects are known to those of skill in the art. In some aspects of all the embodiments of the invention, the compositions are administered through routes, including, but not limited to, ocular, oral, parenteral, intravenous, intramuscular, subcutaneous, transdermal, airway (aerosol), pulmonary, cutaneous, topical, and injection administration.

Administration can be local or systemic. In a preferred embodiment, the administration is injection. In some embodiments, 1, 2, 3, 4, 5, 6, 7, 8, 9, 10, or more administrations can be performed during the course of contraception.

Administration of a Pharmaceutical Composition

An effective amount or dosage of the composition comprising a MIS protein or MIS variant protein (e.g., LR-MIS protein), or nucleic acid encoding the same is administered to reduce the number of primordial follicles being recruited. For example, an effective amount is the amount of MIS protein or MIS variant protein (e.g., LR-MIS protein), or nucleic acid encoding the same to reduce the number of primordial follicles being recruited by at least 10%, at least 20%, at least 30%, at least 40%, at least 50%, at least 60%, at least 70%, at least 80%, at least 90%, or at least 99% compared to when the composition is not administered. An amount of the composition comprising a MIS protein or MIS variant protein (e.g., LR-MIS protein), or nucleic acid encoding the same administered to a female subject is considered effective when the amount is sufficient to reduce the number of primordial follicles being recruited to a desirable number, or decrease the probability of a primordial being recruited to a desirable value. In some embodiments, the amount of composition administered is sufficient to achieve contraception.

In some embodiments, a composition comprising a MIS protein or MIS variant protein (e.g., LR-MIS protein), or nucleic acid encoding the same is can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. The dosage should not be so large as to cause adverse side effects.

In some embodiments, the MIS is a natural (i.e., wild type) human MIS that corresponds to SEQ ID NO: 3.

In some embodiments, the MIS is a recombinant protein or a functional fragment or derivative or variant thereof. In some embodiments, the MIS is a recombinant human MIS protein or a functional fragment or derivative or variant thereof (e.g., SEQ ID NO: 4, or SEQ ID NO: 5).

In the embodiments of administering a composition comprising MIS, to revert the number of primordial follicles being recruited to a normal level, the administration of the composition comprising MIS is terminated. The term "normal level" is used herein to refer to the number of primordial follicles being recruited in the absence of any MIS administration or unnatural MIS.

A recombinant human MIS protein, MIS variant protein or derivative or functional fragment thereof can be administered by any route known in the art or described herein, for example, oral, parenteral (e.g., intravenously or intramuscularly), intraperitoneal, rectal, cutaneous, nasal, vaginal, inhalant, skin (patch), or ocular. The recombinant human MIS protein or derivative or functional fragment protein may be administered in any dose or dosing regimen.

With respect to the therapeutic methods of the invention, it is not intended that the administration of a recombinant human MIS protein or polynucleotide encoding such a recombinant human MIS protein or functional fragment thereof be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat an autoimmune disease or immune-related disorder as disclosed herein. An effective amount, e.g., a therapeutically effective dose of a recombinant human MIS protein may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising a recombinant human MIS protein agent can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

Administration of the compositions comprising a recombinant human MIS protein or MIS protein variant, or nucleic acid encoding the same as disclosed herein may be by parenteral or nonparenteral means, but is preferably oral or intravenous. Treatment may be for short periods of time, e.g., pulsed or continuous throughout the lifetime of the patient. In all aspects of the embodiments as disclosed herein, the agents and compositions as disclosed herein are administered by pulse administration. In some embodiments, they are administered orally to the subject. In some embodiments, the subject is a mammal, e.g., a human. In some embodiments, the subject is undergoing, or will undergo chemotherapeutic treatment or cancer treatment.

In some embodiments, the amount of a MIS protein or MIS protein variant is administered to a subject (in pulses, as continuous treatment or as a one-time administration (e.g., via gene therapy expression of the MIS protein or MIS protein variants)) such that the blood levels of the MIS protein or MIS protein variant in the treated subject are above about 20%, or above about 30%, or above about 40%, or above about 50%, or between about 50-100% or above about 2-fold, or above about 3-fold, or above about 4-fold, or above about 5-fold or more than 5-fold the blood levels of the endogenous MIS protein in an age-matched female subject are generally considered to be sufficient to arrest follicularogeneis in the subject, and thus therefore are sufficient amounts of the MIS protein or MIS variant protein for use in methods for contraception or to preserve ovarian reserve (e.g., to prevent a decline in functional ovarian reserve (FOR)) as disclosed herein.

In some embodiments, administration of a MIS protein or MIS variant protein, or nucleic acid encoding the same, as disclosed herein can be a one-time administration, e.g., via a vector e.g., viral vector or gene therapy where it is desirable for permanent arrest of follicular genesis, e.g., for permanent contraception of animal such as dogs and cats.

In an alternative embodiment, administration of a MIS protein or MIS variant protein as disclosed herein is by pulsed administration, e.g., for temporary arrest of follicularogeneis, e.g., to temporary prevent decline in FOR or temporary contraception of subjects, e.g., human subjects where the subject has a desire to become pregnant at a later timepoint in their life.

In some embodiments, pulsed administration of a composition comprising a MIS protein or MIS protein variant as disclosed herein is more effective than continuous treatment because total pulsed doses are often lower than would be expected from continuous administration of the same composition. Each pulse dose can be reduced and the total amount of drug administered over the course of treatment is minimized. Each pulse dose can be reduced and the total amount of drug administered over the course of treatment to the patient can be minimized. With pulse therapy, in vivo levels of a MIS protein or MIS protein variant as disclosed herein can drop below that level required for effective continuous treatment. Pulsed administration can reduce the amount of a composition comprising a MIS protein or MIS protein variant as disclosed herein administered to the patient per dose, and/or per total treatment regimen with an increased effectiveness. Pulsed administration can provide a saving in time, effort and expense and a lower effective dose can lessen the number and severity of complications that can be experienced by a subject. As such, pulsing can be more effective than continuous administration of the same composition.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient high concentration of a MIS protein or MIS protein variant in the blood of the subject for a long period of time sufficient to arrest folliculogenesis for the desired time period. Pulsed administration can substantially reduce the amount of the composition comprising a MIS protein or MIS protein variant administered to the patient per dose or per total treatment regimen with an increased effectiveness. This represents a significant saving in time, effort and expense and, more importantly, a lower effective dose substantially lessens the number and severity of complications that may be experienced by the patients.

In certain embodiments, a pulsed administration comprises administering one or more MIS protein or MIS variant protein for about 4 weeks, followed by not administering a MIS protein or MIS variant protein for about 1 weeks. In some embodiments, the pulsed administration comprises administering at least one MIS protein or MIS variant protein for about 6 weeks, followed by not administering a MIS protein or MIS variant protein for about 2 weeks. In certain embodiments, the pulsed administration comprises administering at least one MIS protein or MIS variant protein for about 4 weeks, followed by not administering a MIS protein or MIS variant protein for about 2 weeks. In some embodiments, the pulsed administration comprises administering at least one MIS protein or MIS variant protein for about 2 weeks, followed by not administering a MIS protein or MIS variant protein for about 2 weeks. In some embodiments, pulsed administration comprises pulses of administering at least MIS protein or MIS variant protein for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months or longer than 12 months. In certain embodiments, pulsed administration comprises intervals of not administering a MIS protein or MIS variant protein for about 1 day, about 2 days, about 3 days, about 4 days, about 5 days, about 6 days, about 7 days, about 10 days, about 2 weeks, about 3 weeks, about 4 weeks, about 5 weeks, about 6 weeks, about 7 weeks, about 8 weeks, about 2 months, about 3 months, about 4 months, about 5 months, about 6 months, about 9 months, about 12 months or longer than 12 months. In some embodiments, administration is continuous. In certain embodiments, administration of a MIS protein or MIS variant protein is for the lifetime of the subject, where permanent contraception is warranted or desired.

Individual pulses of a composition comprising a MIS protein or MIS protein variant as disclosed herein can be delivered to the patient continuously over a period of several hours, such as about 2, 4, 6, 8, 10, 12, 14 or 16 hours, or several days, such as 2, 3, 4, 5, 6, or 7 days, or more than 7 days, e.g., about 7-14 days, or 14 days to 3 weeks, or 3-4 weeks, or 4-6 weeks or more than 6 weeks. For example, a composition comprising a MIS protein or MIS protein variant can been administered over a period of about 10 to 20 days or 10 to 30 days, followed by a period of 7 days of no treatment.

In one embodiment, a composition comprising a MIS protein or MIS protein variant as disclosed can be administered to a subject for about 2, or about 3, or about 4, or about five weeks, or more than five weeks, e.g., about 2, or about 3, or about 4, or about 5, or about 6 or about 7 or more months, and then a subsequently administered after an appropriate interval for an additional period of time, for example, for about 2, or about 3, or about 4, or about five days, or more than five days. Cycles of treatment may occur in immediate succession or with an interval of no treatment between cycles. Typically, where the subject is administering a composition comprising a MIS protein or MIS variant protein as disclosed herein for the preservation of ovarian reserve (e.g., in a method to prevent a decline in functional ovarian reserve (FOR)), a subject can be administered the composition for a period of between about 3-4 months, or a period of between about 4-6 months, or a period of between about 6-8 months, or a period of between about 8-12 months, or a period of between about 12-24 months, or a period of between about 24-36 months or more than about 36 months, followed by an interval of no delivery, as discussed herein. In some embodiments, where the subject is administering a composition comprising a MIS protein or MIS variant protein as disclosed herein in a method for contraception, a subject can be administered the composition for a period of between about 3-4 months, or a period of between about 4-6 months, or a period of between about 6-8 months, or a period of between about 8-12 months, or a period of between about 12-24 months, or a period of between about 24-36 months or more than about 36 months, or for as long as the subject desires not to become pregnant, followed by an interval of no delivery.

In some embodiments, where pulse therapy is used, the interval between pulses or the interval of no delivery is greater than 24 hours and preferably greater than 48 hours, and can be for even longer such as for 3, 4, 5, 6, 7, 8, 9 or 10 days, two, three or four weeks or even longer. In some embodiments, the interval between pulses can be determined by one of ordinary skill in the art, for example, as demonstrated herein in the Examples, by measuring the level of MIS protein in the blood in the subject after administration of the composition (e.g., the pulse dose), and administering a pulse when the MIS mRNA or MIS protein level reaches a certain pre-defined low threshold limit. Such pre-defined low threshold limits can be determined by one of ordinary skill in the art, and can be, for example, about baseline level, or about 100% or about 200%, or about 300%, or about 400%, or about 500% or mote than 500% above the baseline level of exogenous MIS protein levels in an age-matched female subject.

Alternatively, in some embodiments, the interval between pulses can be calculated by administering another dose of a composition comprising a MIS protein or MIS protein variant as disclosed herein, and when the active component of the composition is no longer detectable in the patient prior to delivery of the next pulse. Alternatively, intervals can also be calculated from the in vivo half-life of the composition. For example, intervals can also be calculated from the in vivo half-life of the composition, or the levels of MIS protein or MIS variant protein in the blood. Intervals may be calculated as greater than the in vivo half-life, or 2, 3, 4, 5 and even 10 times greater the composition half-life. For compositions with fairly rapid half lives, intervals may be 25, 50, 100, 150, 200, 250 300 and even 500 times the half life of the chemical composition. The number of pulses in a single therapeutic regimen may be as little as two, but is typically from about 5 to 10, 10 to 20, 15 to 30 or more. In some embodiments, patients receive a composition comprising a MIS protein or MIS protein variant as disclosed herein for life, or a desired timespan where the subject does not wish to become pregnant, according to the methods of this invention without the problems and inconveniences associated with current therapies.

In certain embodiments, a composition comprising a MIS protein or MIS protein variant as disclosed herein can be administered by most any means, but are preferable delivered to the patient as an injection (e.g. intravenous, subcutaneous, intraarterial), infusion or instillation, and more preferably by oral ingestion or intravaginal administration.

In some embodiments, administration of a composition comprising a MIS protein or MIS protein variant as disclosed herein can be intermittent; for example, administration can be once every two days, every three days, every five days, once a week, once or twice a month, and the like. The amount, forms, and/or amounts of the different forms of a composition comprising a MIS protein or MIS protein variant as disclosed herein can be varied at different times of administration.

In some embodiments, a composition comprising a MIS protein or MIS protein variant as disclosed herein can be administered to a subject before a chemotherapeutic treatment, or radiation treatment is administered to the subject. In alternative embodiments, a composition comprising a MIS protein or MIS protein variant as disclosed herein can be co-administered to a subject concurrently with another agent or treatment regimen, e.g., concurrently with a chemotherapeutic treatment, or radiation treatment. In some embodiments, a composition comprising a MIS protein or MIS protein variant as disclosed herein can be co-administered with a pharmaceutical composition comprising an comprising one or more addition agents. The pharmaceutical compositions can be provided by pulsed administration. For example, a composition comprising a MIS protein or MIS protein variant as disclosed herein can be administered to a subject, followed by a chemotherapeutic treatment, or radiation treatment after an interval of time has passed, and this order of administration the same or similar time interval can be repeated, for example, at least 1, 2, 3, 4, 5, 6, 7, 8, 9, or 10 or more times. Pulsed administration of one or more pharmaceutical compositions comprising a MIS protein or MIS protein variant as disclosed herein can be used for prophylactic treatment, for example, a subject who will, or has or is currently undergoing chemotherapy and chemoradiation therapy, to avoid chemotherapy or radiotherapy-induced premature ovarian failure.

In some embodiments, a subject can receive one or more compositions comprising a MIS protein or MIS protein variant as disclosed for life according to the methods of this invention, for example, where the subject has a desire to permanently prevent pregnancy, e.g., for animal subjects such as cats and dogs. Compositions can be administered by most any means, and can be delivered to the subject as an oral formulation, or injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590, which are incorporated herein in their entirety by reference.

While the attending physician ultimately will decide the appropriate amount and dosage regimen, an effective amounts of a recombinant human MIS protein or derivative or functional fragment thereof can provided at a dose of 0.0001, 0.01, 0.01 0.1, 1, 5, 10, 25, 50, 100, 500, or 1,000 mg/kg. Effective doses may be extrapolated from dose-response curves derived from in vitro or animal model test bioassays or systems. In some embodiments, doses of a recombinant human MIS protein are about 1 pg/kg to 10 mg/kg (body weight of patient) although lower and higher doses can also be administered.

In some embodiments, reference ranges for doses of recombinant human MIS are estimated from reference groups in the United States, and are disclosed in Antimullerian Hormone (AMH), Serum from Mayo Medical Laboratories. Retrieved April 2012. In some embodiments, female subjects can be administered the following doses of recombinant human MIS: females 13-45 years: 1 to 10 ng/mL; females older than 45 years: Less than 1 ng/mL. It is noted that MIS measurements may be less accurate if the person being measured is vitamin D deficient.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of a recombinant human MIS protein or functional derivatives or functional fragments thereof as disclosed herein, and the condition of the patient, the autoimmune disease to be treated, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising a recombinant human MIS protein or functional derivatives or functional fragments thereof are optionally tested in one or more appropriate in vitro and/or in vivo animal models of disease, such as an Mullerian duct regression bioassay as disclosed herein in the Examples, and known to persons of ordinary skill in the art, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of a recombinant human MIS protein or functional derivatives or functional fragments thereof at various concentrations, e.g., as applied to the mass and overall health of the patient. Administration can be accomplished via single or divided doses.

In determining the effective amount of a recombinant human MIS protein, MIS variant protein (e.g., LR-MIS protein) or functional derivatives or functional fragments thereof, or nucleic acids encoding the same, to be administered in the treatment or prophylaxis of a disease, the physician evaluates circulating plasma levels of MIS proteins, formulation toxicities, and progression of the disease. The selected dosage level will also depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, a recombinant human MIS protein or MIS variant protein (e.g., LR-MIS protein), or nucleic acid encoding the same, as disclosed herein can be administered at a dose in accordance with good medical practice, taking into account the clinical condition of the individual patient, the site and method of administration, scheduling of administration, patient age, sex, body weight and other factors known to medical practitioners.

Dosage regimens of a composition comprising a recombinant human MIS protein, MIS variant protein (e.g., LR-MIS protein) or functional fragment or variant thereof, or nucleic acid encoding the same, as disclosed herein can be adjusted to provide the optimum desired response (e.g. a therapeutic or prophylactic response). For example, a single bolus can be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Furthermore, actual dosage levels of a recombinant human MIS protein or MIS variant protein (e.g., LR-MIS protein) in a pharmaceutical composition can be varied so as to obtain an amount of the active ingredient which is effective to achieve the desired therapeutic response for a particular subject, composition, and mode of administration, without being toxic to the subject. A pharmaceutical composition comprising a recombinant human MIS protein or functional fragment or variant thereof as disclosed herein can be a "therapeutically effective amount" and/or a "prophylactically effective amount". In general, a suitable daily dose of a composition comprising a recombinant human MIS protein or functional fragment or variant thereof as disclosed herein will be that amount of the a recombinant human MIS protein which is the lowest dose effective to produce a therapeutic effect, such as a reduction of a symptom of a proliferative disorder or cancer as disclosed herein. Such an effective dose will generally depend upon the factors described above.

If desired, the effective daily dose of a composition comprising recombinant human MIS protein or functional fragment or variant thereof can be administered as two, three, four, five, six or more sub-doses administered separately at appropriate intervals throughout the day, optionally, in unit dosage forms.

The dosage level administered to a subject can be constant over a desired period of time, for example, at least 1 week, at least 2 weeks, at least 3 weeks, at least 1 month, at least 2 months, at least 3 months, at least 6 months, at least 1 year, or at least 5 years or more than 5 years. Alternatively, the dosage level administered to a subject can vary depending on the progression of the condition being treated, e.g., depending the FOR (functional ovarian reserve) of the subject, or severity of the POA or DOR (diminished ovarian reserve).

It is to be noted that dosage values may vary depending the females FOR (functional ovarian reserve), or severity of the POA or DOR (diminished ovarian reserve) to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. An appropriate experimental model which can be used includes determining a the dose can be use of the mullerian duct regression bioassay as disclosed herein in the examples, or a in vivo cancer model which is commonly known by ordinary skill in the art. In vivo cancer models are discussed in Frese et al., "Maximizing mouse cancer models" Nat Rev Cancer. 2007 September; 7(9):645-58 and Santos et al., Genetically modified mouse models in cancer studies. Clin Transl Oncol. 2008 December; 10(12):794-803, and "Cancer stem cells in mouse models of cancer", 6th Annual MDI Stem Cell Symposium, MDI Biological Lab, Salisbury Cove, Me., Aug. 10-11, 2007" which are incorporated herein in their entirety by reference.

For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect. For example, the therapeutically effective amount of a recombinant human MIS protein can be assessed in a mouse model of fertility.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. It is also noted that humans are treated generally longer than the mice or other experimental animals exemplified herein, which treatment has a length proportional to the length of the disease process and drug effectiveness. The doses may be single doses or multiple doses over a period of several days, but single doses are preferred.

In some embodiments, a recombinant human MIS protein (e.g., proteins or nucleic acids encoding a recombinant human MIS protein or fragments thereof) can be administered to humans and other animals for therapy by any suitable route of administration, including orally, nasally, as by, for example, a spray, rectally, intravaginally, parenterally, intracisternally and topically, as by powders, ointments or drops, including buccally and sublingually.

After formulation with an appropriate pharmaceutically acceptable carrier in a desired dosage, a pharmaceutical composition comprising a recombinant human MIS protein or functional fragment or variant thereof as disclosed herein can be administered to a subject. A pharmaceutical a composition comprising a recombinant human MIS protein, or MIS variant protein (e.g., LR-MIS protein), or functional fragment or variant thereof can be administered to a subject using any suitable means. In general, suitable means of administration include, but are not limited to, topical, oral, parenteral (e.g., intravenous, subcutaneous or intramuscular), rectal, intracisternal, intravaginal, intraperitoneal, ocular, or nasal routes.

In a specific embodiment, it may be desirable to administer the pharmaceutical composition comprising a recombinant human MIS protein locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes. In some embodiments, a recombinant human MIS protein as disclosed herein can be applied to the muscle using topical creams, patches, intramuscular injections and the like.

In some embodiments, a recombinant human MIS protein as disclosed herein can be administered vaginally, e.g., using including hydrogels, vaginal tablets, pessaries/suppositories, particulate systems, and intravaginal rings, as known to one of ordinary skill in the art and disclosed in Woolfson et al., "Drug delivery by the intravaginal route" Crit Rev. Ther. Drug Carrier Syst., 2000 (17(5); 509-599, which is incorporated herein in its entirety by reference. In some embodiments, a recombinant human MIS protein as disclosed herein can be administered vaginally using vaginal mucoadhesive drug delivery systems (DDS), as disclosed in Maurya S K et al., "Therapeutic potential of mucoadhesive drug delivery systems—an updated patent review" Recent Pat Drug Deliv Formul. 2010 November; 4(3):256-65; Balaglu et al., "Strategies to prolong the intravaginal residence time of drug delivery systems" J Pharm Pharm Sci. 2009; 12(3): 312-36 and de Araújo Pereira; "Vaginal mucoadhesive drug delivery systems" Drug Dev Ind Pharm. 2012 June; 38(6): 643-52, which are incorporated herein in their entirety by reference. In some embodiments, a recombinant human MIS protein as disclosed herein can be administered vaginally using mucoadhesive microspheres, as disclosed in Krutik et al., "Mucoadhesive microspheres: a promising tool in drug delivery" Patil et al., Curr Drug Deliv 2008 October; 5(4): 312-8.

In some embodiments, a recombinant human MIS protein can be administered to a subject orally (e.g., in capsules, suspensions or tablets) or by parenteral administration. Conventional methods for oral administration include administering a recombinant human MIS protein in any one of the following; tablets, suspensions, solutions, emulsions, capsules, powders, syrups and the like are usable. Known techniques that deliver a recombinant human MIS protein orally or intravenously and retain the biological activity are preferred. Parenteral administration can include, for example, intramuscular, intravenous, intraarticular, intraarterial, intrathecal, subcutaneous, or intraperitoneal administration. A recombinant human MIS protein can also be administered orally, transdermally, topically, by inhalation (e.g., intrabronchial, intranasal, oral inhalation or intranasal drops) or rectally. Administration can be local or systemic as indicated. Agents, e.g., nucleic acid agents which encode a recombinant human MIS protein or functional fragment thereof can also be delivered using a vector, e.g., a viral vector by methods which are well known to those skilled in the art.

When administering a composition comprising a recombinant human MIS protein or functional fragment or variant thereof as disclosed herein parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils.

The term "Dosage unit" form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the a recombinant human MIS protein or functional fragment or variant thereof as disclosed herein and the particular therapeutic or prophylactic effect to be achieved, and (b) the limitations inherent in the art of compounding a recombinant human MIS protein an active agent for the treatment of sensitivity in individuals.

The pharmaceutically acceptable compositions comprising a recombinant human MIS protein or functional fragment or variant thereof as disclosed herein can be suspended in aqueous vehicles and introduced through conventional hypodermic needles or using infusion pumps.

Pharmaceutical Compositions

In some embodiments, a composition comprising a recombinant human MIS protein, or MIS variant protein (e.g., LR-MIS) or functional fragment or variant thereof as disclosed herein can be formulated in any suitable means, e.g., as a sterile injectable solution, e.g., which can be prepared by incorporating the recombinant human MIS protein in the required amount of the appropriate solvent with various of the other ingredients, as desired.

A pharmacological formulation of a composition comprising a recombinant human MIS protein, or MIS variant protein (e.g., LR-MIS) or functional fragment or variant thereof as disclosed herein can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those presented in U.S. Pat. Nos. 5,225,182; 5,169,383; 5,167,616; 4,959,217; 4,925,678; 4,487,603; 4,486,194; 4,447,233; 4,447,224; 4,439,196 and 4,475,196. Other such implants, delivery systems, and modules are well known to those skilled in the art.

Proper fluidity can be maintained, for example, by the use of a coating such as lecithin, by the maintenance of the required particle size in the case of dispersion and by the use of surfactants. Non-aqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including anti-microbial preservatives, antioxidants, chelating agents, and buffers, can be added. Prevention of the action of microorganisms can be ensured by various antibacterial and antifungal agents, e.g., parabens, chlorobutanol, phenol and sorbic acid. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

In another embodiment, a composition comprising a recombinant human MIS protein, or MIS variant protein (e.g., LR-MIS) or functional fragment or variant thereof as disclosed herein can comprise lipid-based formulations. Any of the known lipid-based drug delivery systems can be used in the practice of the invention. For instance, multivesicular liposomes, multilamellar liposomes and unilamellar liposomes can all be used so long as a sustained release rate of the encapsulated active compound can be established. Methods of making controlled release multivesicular liposome drug delivery systems are described in PCT Application Publication Nos: WO 9703652, WO 9513796, and WO 9423697, the contents of which are incorporated herein by reference.

In some embodiments, the composition used in the methods described herein can be in a controlled release form. A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The composition of the synthetic membrane vesicle is usually a combination of phospholipids, usually in combination with steroids, especially cholesterol. Other phospholipids or other lipids may also be used. Examples of lipids useful in synthetic membrane vesicle production include phosphatidylglycerols, phosphatidylcholines, phosphatidylserines, phosphatidylethanolamines, sphingolipids, cerebrosides, and gangliosides, with preferable embodiments including egg phosphatidylcholine, dipalmitoylphosphatidylcholine, distearoylphosphatidyleholine, dioleoylphosphatidylcholine, dipalmitoylphosphatidylglycerol, and dioleoylphosphatidylglycerol.

In preparing lipid-based vesicles containing a recombinant human MIS protein or functional fragment or variant thereof, such variables as the efficiency of active compound encapsulation, labiality of the active compound, homogeneity and size of the resulting population of vesicles, active compound-to-lipid ratio, permeability, instability of the preparation, and pharmaceutical acceptability of the formulation should be considered.

In another embodiment, a recombinant human MIS protein, or MIS variant protein (e.g., LR-MIS) can be delivered in a vesicle, in particular a liposome (see Langer (1990) Science 249:1527-1533). In yet another embodiment, a recombinant human MIS protein can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a recombinant human MIS protein, or MIS variant protein (e.g., LR-MIS), the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Prior to introduction, a composition comprising a recombinant human MIS protein, or MIS variant protein (e.g., LR-MIS) or functional fragment or variant thereof as disclosed herein can be sterilized, by any of the numerous available techniques of the art, such as with gamma radiation or electron beam sterilization.

In another embodiment of the invention, a composition comprising a recombinant human MIS protein, or MIS variant protein (e.g., LR-MIS) or functional fragment or variant thereof as disclosed herein, can be administered and/or formulated in conjunction (e.g., in combination) with any other therapeutic agent. For purpose of administration, a recombinant human MIS protein or functional fragment or variant thereof as disclosed herein is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds of this invention in an appropriate manner, and in accordance with accepted practices, such as those disclosed in Remington's Pharmaceutical Sciences, Gennaro, Ed., Mack Publishing Co., Easton, Pa. 1990.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches, that comprise one or more resolvins and/or protectins or their analogues of the invention.

Formulations of a composition comprising a recombinant human MIS protein, or MIS variant protein (e.g., LR-MIS) or functional fragment or variant thereof as disclosed herein can be prepared by a number or means known to persons skilled in the art. In some embodiments the formulations can be prepared for administration as an aerosol formulation, e.g., by combining (i) a recombinant human MIS protein, or MIS variant protein (e.g., LR-MIS) or functional fragment or variant thereof as disclosed herein in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

In certain embodiments, a composition comprising a recombinant human MIS protein, or MIS variant protein (e.g., LR-MIS) as disclosed herein can be administered to a subject as a pharmaceutical composition with a pharmaceutically acceptable carrier. In certain embodiments, these pharmaceutical compositions optionally further comprise one or more additional therapeutic agents. Of course, such therapeutic agents are which are known to those of ordinary skill in the art can readily be identified by one of ordinary skill in the art.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Formulations of the invention suitable for oral administration of a MIS protein, or MIS variant protein (e.g., LR-MIS) may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), of a MIS protein or, or MIS variant protein (e.g., LR-MIS) is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some instances, a composition comprising a recombinant human MIS protein or functional fragment or variant thereof as disclosed herein can be in a formulation suitable for rectal or vaginal administration, for example as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore release the active compound. Suitable carriers and formulations for such administration are known in the art.

Dosage forms for the topical or transdermal administration of a recombinant human MIS protein of this invention, e.g., for muscular administration include powders, sprays, ointments, pastes, creams, lotions, gels, solutions, patches and inhalants. A recombinant human MIS protein or functional fragment or variant thereof as disclosed herein may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a recombinant human MIS protein of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, a recombinant human MIS protein, or MIS variant protein (e.g., LR-MIS) or functional fragment or variant thereof can be isolated and/or purified or substantially purified by one or more purification methods described herein or known by those skilled in the art. Generally, the purities are at least 90%, in particular 95% and often greater than 99%. In certain embodiments, the naturally occurring compound is excluded from the general description of the broader genus.

In some embodiments, the composition comprises at least one a recombinant human MIS protein, or MIS variant protein (e.g., LR-MIS) in combination with a pharmaceutically acceptable carrier. Some examples of materials which can serve as pharmaceutically acceptable carriers include, without limitation: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, a composition comprising a recombinant human MIS protein, or MIS variant protein (e.g., LR-MIS) or functional fragment or variant thereof as disclosed herein can contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention.

These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of patients without undue toxicity, irritation, allergic response, and the like, commensurate with a reasonable benefit/risk ratio, and effective for their intended use. These compounds include the zwitterionic forms, where possible, of r compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "prodrug" refers to compounds or agents that are rapidly transformed in vivo to yield the active recombinant human MIS protein, e.g., a biologically active or functional active MIS protein or nucleic acid (e.g., mRNA, DNA, MOD-RNA) which encodes a functionally active MIS protein. In some embodiments, a recombinant human MIS protein prodrug can be activated by hydrolysis in blood, e.g., via cleavage of a leader sequence, and or cleavage at the primary cleavage site to result in the N-terminal and C-terminal domains for production of a bioactive MIS protein, similar to how insulin is activated from its proprotein into an active insulin protein. A thorough discussion is provided in T. Higachi and V. Stella, "Pro-drugs as Novel Delivery Systems," Vol. 14 of the A.C.S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. The prodrug may be designed to alter the metabolic stability or the transport characteristics of a recombinant human MIS protein, to mask side effects or toxicity, or to alter other characteristics or properties of the recombinant human MIS protein.

By virtue of knowledge of pharmacodynamic processes and drug metabolism or post-translational protein processing of MIS in vivo, once a pharmaceutically active compound is identified, those of skill in the pharmaceutical art generally can design a recombinant human MIS protein prodrug which can be activated in vivo to increase levels of a bioactive MIS protein in the subject (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

As discussed herein, in some embodiments a composition comprising a recombinant human MIS protein, or MIS variant protein (e.g., LR-MIS) or functional fragment or variant thereof as disclosed herein can be conjugated or covalently attached to a targeting agent to increase their tissue specificity and targeting to a cell, for example a muscle cells. Targeting agents can include, for example without limitation, antibodies, cytokines and receptor ligands, as discussed in the section entitled "targeting." In some embodiments, the targeting agent is overexpressed on the cells to be targeted, for example the muscle cells as compared to non-muscle cells.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The term "Mullerian Inhibiting Substance" and "MIS" are used interchangeably herein and is also known as anti-Müllerian hormone or AMH, refer to compounds and materials which are structurally similar to MIS. By "MIS" or "Mullerian Inhibiting Substance" is meant a polypeptide having an amino acid sequence at least about 60%, or at least about 70%, or at least about 80%, or at least about 90%, or at least about 95%, or at least about 96%, or at least about 97%, or at least about 98%, or at least about 99% identical to amino acid residues 26-560 of SEQ ID NO: 3. The present invention is intended to include mutant forms of recombinant human MIS which have substantially the same, or greater biological activity as wild-type MIS. Examples of such mutant MIS molecules carrying a deletion, insertion, or alteration in the amino acid sequence of wild-type MIS (e.g., amino acid residues 26-560 of SEQ ID NO:3). Other forms of include substances are for example, salts, functional derivatives and aglycone forms of wild-type MIS and recombinant human MIS. Additionally, human recombinant MIS protein can be obtained using recombinant DNA technology, or from chemical synthesis of the MIS protein. For reference purposes only, the wild-type human MIS nucleic acid corresponds to RefSeq No: NM_000479, which are incorporated herein by reference.

The term "Mullerian Inhibiting Substance type II receptor" or "MISRII" are used interchangeably herein to refer to the type II receptor for MIS. The term MISRII is intended to encompass all MIS receptors substantially homologous to MISRII and functional derivatives of MISRII. MISRII is also known by the alias as AMHR2, and for reference purposes, the nucleic acid sequence of human MISRII corresponds to NM_020547 and GenBank No: AF172932 which are incorporated herein by reference The term "wild type" refers to the naturally-occurring polynucleotide sequence encoding a protein, or a portion thereof, or protein sequence, or portion thereof, respectively, as it normally exists in vivo. Accordingly, as disclosed herein, the wild type amino acid sequence for the pre-proprotein of human MIS corresponds to SEQ ID NO: 3, where amino acid residues 1-25 correspond to the leader sequence. The proprotein of MIS comprises amino acid residues 26-560 of SEQ ID NO: 3 (e.g., lacking the 1-25 leader sequence), which is then post-translationally processed by cleavage as discussed herein to form a bioactive MIS homodimer.

The term "soluble MIS polypeptide" as used herein refers to a MIS polypeptide that does not comprise at least part of, or all of, the amino acids which allow it to functionally bind to the membrane.

By a "polynucleotide encoding MIS" is meant a polynucleotide encoding a polypeptide having at least about 60%, or at least about 70%, or at least about 80%, or at least about 90%, or at least about 95%, or at least about 96%, or at least about 97%, or at least about 98%, or at least about 99% sequence identity to any of the amino acid sequences corresponding to amino acid residues 26-560 of SEQ ID NO: 3.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G." a thymine "T" or a cytosine "C") or RNA (e.g. an A, a G. an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. The term "nucleic acid" also refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein.

As used herein, the term "gene" refers to a nucleic acid comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid may encompass a double-stranded molecule or a double-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts." The term "gene" refers to the segment of DNA involved in producing a polypeptide chain, it includes regions preceding and following the coding region as well as intervening sequences (introns) between individual coding segments (exons). A "promoter" is a region of a nucleic acid sequence at which initiation and rate of transcription are controlled. It may contain elements at which regulatory proteins and molecules may bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and may be upstream or downstream of the promoter.

The terms "polypeptide" and "protein" are used interchangeably to refer to a polymer of amino acid residues, and are not limited to a minimum length. Peptides, oligopeptides, dimers, multimers, and the like, are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational and post-translational modifications of the polypeptide, such as, for example, disulfide-bond formation, glycosylation, acetylation, phosphorylation, proteolytic cleavage (e.g., cleavage by furins or metalloproteases and prohormone convertases (PCs)), and the like. Furthermore, for purposes of the present invention, a "polypeptide" encompasses a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 50 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 50 amino acids in length.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, a recombinant human MIS protein is comprised of D- or L-amino acid residues, as use of naturally occurring L-amino acid residues has the advantage that any break-down products should be relatively non-toxic to the cell or organism.

The term "fragment" of a peptide, polypeptide or molecule as used herein refers to any contiguous polypeptide subset of the molecule. The term "protein fragment" as used herein includes both synthetic and naturally-occurring amino acid sequences derivable from MIS proteins of SEQ ID NO:3 or 4 or 5. The protein fragment can be obtained by fragmenting the recombinant human MIS protein, or if it can be synthesized based upon a knowledge of the sequence of the naturally occurring amino acid sequence or of the genetic material (DNA or RNA) which encodes this sequence. Accordingly, a "fragment" of a molecule, is meant to refer to any polypeptide subset of the molecule. In some embodiments, a functional fragment of recombinant human MIS comprises at least the C-terminal domain and at least the N-terminal domain. In some embodiments, a functional fragment comprises a portion of the C-terminal and/or a portion (e.g., fragment) of the N-terminal domain of the recombinant human MIS protein. Fragments of a recombinant human MIS protein which have the activity at least or greater than the MIS protein of SEQ ID NO: 3, 4, or 5 as disclosed herein and which are soluble are also encompassed for use in the present invention.

Fragments of a recombinant human MIS protein, for example functional fragments of SEQ ID NO: 3, 4 or 5 useful in the methods as disclosed herein have at least 30% the activity as that of a polypeptide of SEQ ID NO: 3, 4 or 5 in vivo, e.g., to cause inhibition of follicle maturation as disclosed herein in the Examples. Stated another way, a functional fragment of a recombinant human MIS protein is a fragment of any of SEQ ID NO: 3, 4 or 5 which, alone or as a fusion protein can result in at least 30% of the same activity as compared to SEQ ID NO: 3, 4 or 5 to bind and activate MISRII, or inhibit follicle maturation as disclosed herein. Fragments as used herein can be soluble (i.e. not membrane bound). A "fragment" can be at least about 6, at least about 9, at least about 15, at least about 20, at least about 30, least about 40, at least about 50, at least about 100, at least about 250, at least about 300 nucleic or amino acids, and all integers in between. Exemplary fragments include C-terminal truncations, N-terminal truncations, or truncations of both C- and N-terminals (e.g., deletions of, for example, at least 1, at least 2, at least 3, at least 4, at least 5, at least 8, at least 10, at least 15, at least 20, at least 25, at least 40, at least 50, at least 75, at least 100 or more amino acids deleted from the N-termini, the C-termini, or both). One of ordinary skill in the art can create such fragments by simple deletion analysis. Such a fragment of SEQ ID NO: 3, 4 or 5 can be, for example, 1, 2, 3, 4, 5, 6, 7, 8, 9 or 10 amino acids or more than 10 amino acids, such as 15, 30, 50, 100 or more than 100 amino acids deleted from the N-terminal and/or C-terminal of SEQ ID NO: 3, 4 or 5, respectively. Persons of ordinary skill in the art can easily identify the minimal peptide fragment of SEQ ID NO: 3, 4 or 5 useful in the methods and compositions as disclosed herein, or fusion proteins as disclosed herein, by sequentially deleting N- and/or C-terminal amino acids from SEQ ID NO: 3, 4 or 5, or sequentially deleting N- and C-terminal amino acids from recombinant human MIS protein and assessing the function of the resulting peptide fragment, alone or when it is cleaved. One can create functional fragments with multiple smaller fragments. These can be attached by bridging peptide linkers. One can readily select linkers to maintain wild type conformation. In some embodiments, a fragment must be at least 6 amino acids, at least about 9, at least about 15, at least about 20, at least about 30, at least about 40, at least about 50, at least about 100, at least about 250, at least about 500 continuous nucleic acids or amino acids, or any integers in between.

The term "derivative" as used herein refers to peptides which have been chemically modified, for example but not limited to by techniques such as ubiquitination, labeling, pegylation (derivatization with polyethylene glycol) or addition of other molecules. A molecule also a "derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" or "fragment" refers to a polypeptide which possess a biological activity (either functional or structural) that is substantially similar to a biological activity of the polypeptide which it is a functional derivative, variant or functional fragment thereof. The term functional derivative is intended to include the fragments, analogues or chemical derivatives of a molecule. By "substantially similar" in this context is meant that the biological activity, e.g., activation of MISRII is at 25% or at least 35%, or at least 50% as active as a reference polypeptide, e.g., a corresponding wild-type MIS polypeptide or recombinant human MIS protein, and preferably at least 60% as active, 70% as active, 80% as active, 90% as active, 95% as active, 100% as active or even higher (i.e., the variant or derivative has greater activity than the wild-type), e.g., 110% as active, 120% as active, or more. Stated another way, a "substantially similar" functional fragment of a recombinant human MIS protein in this context is meant that at least 25%, at least 35%, at least 50% of the relevant or desired biological activity of a corresponding recombinant human MIS protein is retained. In the instance of a functional fragment or peptide of a recombinant human MIS protein as disclosed herein (e.g., SEQ ID NO: 3, 4 or 5), a functional fragment of SEQ ID NO: 3, 4 or 5 would be a protein or peptide comprising a portion of SEQ ID NO: 3, 4 or 5 which retained an activity to activate MISRII, or inhibit follicle maturation as disclosed herein; preferably the fragment of SEQ ID NO: 3, 4 or 5 that retains at least 25%, at least 35%, at least 50% at least 60%, at least 70%, at least 80%, at least 90%, at least 95%, at least 100% or even higher (i.e., the variant or derivative has greater activity than a MIS protein of SEQ ID NO: 3 or of a recombinant human MIS protein of SEQ ID NO 4 or 5), e.g., at least 110%, at least 120%, or more activity compared to MIS proteins corresponding to SEQ ID NO: 3, 4 or 5.

The term "functional derivative" and "mimetic" or "biologically active variant" or "biologically active fragment" are used interchangeably, and refers to a compound which possess a biological activity (either functional or structural) that is substantially similar to a biological activity of the entity or molecule its is a functional derivative of (e.g., the recombinant human MIS protein). The term functional derivative is intended to include the fragments, variants, analogues or chemical derivatives of a molecule.

The term "functional derivatives" is intended to include the "fragments," "variants," "analogs," or "chemical derivatives" of a molecule. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical. An "analog" of a recombinant human MIS protein is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

A "variant" of a recombinant human MIS protein is meant to refer to a molecule substantially similar in structure and function to either the entire molecule, or to a fragment thereof. Accordingly, the term "variant" as used herein refers to a peptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of a recombinant human MIS protein is meant to refer to a molecule substantially similar in structure and function, i.e. where the function is the ability to activate MISRII.

For example, a variant of a recombinant human MIS protein can contain a modification that differs from a reference amino acid in SEQ ID NO: 3, 4 or 5. In some embodiments, a variant of SEQ ID NO: 3, 4 or 5 is a fragment of SEQ ID NO: 3, 4 or 5 as disclosed herein. In some embodiments, a variant can be a different isoform of SEQ ID NO: 3, 4 or 5 or can comprise different isomer amino acids. Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins.

The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to reduce T-reg cells and/or decrease inflammatory cytokines as disclosed herein). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In some embodiments, individual substitutions, deletions or additions that alter, add or delete a single amino acid or a small percentage of amino acids can also be considered "conservative substitutions" is the change does not reduce the activity of the MIS protein (i.e. the ability of a recombinant human MIS protein or variant to cause Mullerian duct regression in vivo, which can be determined using the Mullerian Duct regression bioassay as disclosed herein). Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants. A variant of a recombinant human MIS protein, for example a variant of SEQ ID NO: 3, 4 or 5 is meant to refer to any molecule substantially similar in structure and function to either the entire molecule of SEQ ID NO: 3, 4 or 5, or to a fragment thereof.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. Determination of homologs of the genes or peptides of the present invention can be easily ascertained by the skilled artisan.

The term "substantially homologous" refers to sequences that are at least 90%, at least 95% identical, at least 96%, identical at least 97% identical, at least 98% identical or at least 99% identical. Homologous sequences can be the same functional gene in different species. Determination of homologs of the genes or peptides of the present invention can be easily ascertained by the skilled artisan.

A molecule is said to be "substantially similar" to another molecule if both molecules have substantially similar structures or if both molecules possess a similar biological activity, for example if both molecules are able to activate MISRII or inhibit ovarian follicle maturation. Thus, provided that two molecules possess a similar activity, (i.e. a variant of a recombinant human MIS protein which can activate MISRII similar to that of the MIS protein which corresponds to SEQ ID NO: 3, or recombinant human MIS protein which corresponds to SEQ ID NO: 4 or 5) are considered variants and are encompassed for use as disclosed herein, even if the structure of one of the molecules not found in the other, or if the sequence of amino acid residues is not identical. Thus, provided that two molecules possess a similar biological activity, they are considered variants as that term is used herein even if the structure of one of the molecules not found in the other, or if the sequence of amino acid residues is not identical. As such, nucleic acid and amino acid sequences having lesser degrees of similarity but comparable biological activity to recombinant human MIS protein are considered to be equivalents. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a specific nucleic acid sequence of SEQ ID NO:1 or 2 as disclosed herein if: (a) the nucleotide sequence is hybridizes to the coding regions of the natural MIS nucleic acid, or (b) the nucleotide sequence is capable of hybridization to nucleotide sequence of a recombinant human MIS protein encoded by SEQ ID NO: 1 or 2 under moderately stringent conditions and has biological activity similar to the recombinant human MIS protein; or (c) the nucleotide sequences which are degenerative as a result of the genetic code to the nucleotide sequences defined in (a) or (b). Substantially similar proteins will typically be greater than about 80% similar to the corresponding sequence of the native protein.

The term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions.

In one embodiment, the term "human homolog" to a gene transcript refers to a DNA sequence that has at least about 55% homology to the full length nucleotide sequence of the sequence of a recombinant human MIS protein gene as encoded by the genome of humans or an animal, for example mouse or transgenic animal. In one embodiment, the term "human homolog" to a protein identified as associated with a recombinant human MIS protein refers to an amino acid sequence that has 40% homology to the full length amino acid sequence of the protein identified as associated with a recombinant human MIS protein as encoded by the genome of the transgenic animal of the present invention, more preferably at least about 50%, still more preferably, at least about 60% homology, still more preferably, at least about 70% homology, even more preferably, at least about 75% homology, yet more preferably, at least about 80% homology, even more preferably at least about 85% homology, still more preferably, at least about 90% homology, and more preferably, at least about 95% homology. As discussed above, the homology is at least about 50% to 100% and all intervals in between (i.e., 55%, 60%, 70%, 75%, 80%, 85%, 90%, 95%, 98%, etc.). Determination of the human homologs of the genes of the present invention may be easily ascertained by the skilled artisan.

The term "conservative substitution," when describing a polypeptide, refers to a change in the amino acid composition of the polypeptide that does not substantially alter the polypeptide's activity. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions."

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

An "analog" of a molecule such as a recombinant human MIS protein, for example SEQ ID NO: 4 or 5 refers to a molecule similar in function to either the entire molecule or to a fragment thereof. The term "analog" is also intended to include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; acedisubstituted amino acids, N-alkyl amino acids, lactic acid, 4-hydroxyproline, β-carboxyglutamate, ε-N,N,N-trimethyllysine, ε-N-acetyllysine, 0-phosphoserine, N-acetylserine, N-formylmethionine, 3-methylhistidine, 5-hydroxylysine, ε-N-methylarginine. Fragments and analogs can be screened for prophylactic or therapeutic efficacy in transgenic animal models as described below.

By "covalently bonded" is meant joined either directly or indirectly (e.g., through a linker) by a covalent chemical bond.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding the recombinant human MIS-fusion protein is derived from the nucleotide sequence of encoding a recombinant human MIS protein or a functional derivative fragment or variant thereof, fused in frame to an end, either the 5' or the 3' end, of a gene encoding a first fusion partner, such as a IgG1 Fc fragment. In this manner, on expression of the gene, the recombinant human MIS protein or functional derivative fragment or variant thereof is functionally expressed and fused to the N-terminal or C-terminal end of the IgG1 Fc. In certain embodiments, modification of the polypeptide probe is such that the functionality of the recombinant human MIS protein or a functional derivative fragment or variant thereof remains substantially unaffected in terms of its biological activity by fusion to the first fusion partner, such as IgG1 Fc.

By "specifically binds" or "specific binding" is meant a compound or antibody that recognizes and binds a desired polypeptide but that does not substantially recognize and bind other molecules in a sample, for example, a biological sample, which naturally includes a polypeptide of the invention.

By "substantially pure" or is meant a nucleic acid, polypeptide, or other molecule that has been separated from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally occurring organic molecules with which it is naturally associated. For example, a substantially pure polypeptide may be obtained by extraction from a natural source, by expression of a recombinant nucleic acid in a cell that does not normally express that protein, or by chemical synthesis.

By "enhanced proteolytic stability" is meant a reduction of in the rate or extent of proteolysis of a peptide sequence by at least about 2%, at least about 5%, at least about 10%, at least about 20%, at least about 30%, at least about 40%, at least about 50%, at least about 60%, at least about 70%, at least about 80%, at least about 85%, at least about 90%, at least about 95%, at least about 98%, or at least about 99% as compared to a control sequence under the same conditions (e.g., in vivo or in an in vitro system such as in a cell or cell lysate). A peptide with enhanced proteolytic stability may contain any modification, for example, insertions, deletions, or point mutations which reduce or eliminate a site subject to proteolytic cleavage at a particular site. Sites of proteolytic cleavage may be identified based on known target sequences or using computer software (e.g., software described by Gasteiger et al., Protein Identification and Analysis Tools on the ExPASy Server. In John M. Walker, ed. The Proteomics Protocols Handbook, Humana Press (2005)). Alternatively, proteolytic sites can be determined experimentally, for example, by Western blot for the protein following expression or incubation in a cellular system or cellular lysate, followed by sequencing of the identified fragments to determine cleavage sites.

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide with which it is associated in nature. The term recombinant as used with respect to a protein or polypeptide, means a polypeptide produced by expression of a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The terms "subject" and "individual" are used interchangeably herein, and refer to an animal, for example a human, to whom treatment, including prophylactic treatment, with the pharmaceutical composition according to the present invention, is provided. As used herein, a "subject" means a human or animal. Usually the animal is a vertebrate such as, but not limited to a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female. Additionally, a subject can be an infant or a child.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. In some embodiments, the subject can be a patient or other subject in a clinical setting. In some embodiments, the subject can already be undergoing treatment.

As used herein, the terms "administering," and "introducing" are used interchangeably herein and refer to the placement of the recombinant MIS protein, or an agent or vector expressing the recombinant MIS protein as disclosed herein into a subject by a method or route which results in at least partial localization of a recombinant MIS protein at a desired site. The compounds of the present invention can be administered by any appropriate route which results in blocking folliculogenesis in the subject.

The term "effective amount" as used herein refers to the amount of a recombinant human MIS protein as disclosed herein, to alleviate at least one or more symptom of the disease or disorder, and relates to a sufficient amount of pharmacological composition to provide the desired effect. The phrase "therapeutically effective amount" as used herein, e.g., a pharmaceutical composition comprising at least one recombinant human MIS protein as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylacticly significant reduction in a symptom or clinical marker associated with a cancer or a cancer-mediated condition. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of fertility, and any treatment or administration of the compositions or formulations that leads to preventing pregnancy, or preventing a decrease in follicle ovarian reserve (FOR) indicates effective treatment.

A therapeutically or prophylatically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

The term "prophylactically effective amount" refers to an amount of a recombinant human MIS protein or functional fragment or variant thereof which is effective, at dosages and for periods of time necessary, to achieve the desired prophylactic result, e.g., to prevent pregnancy or prevent decrease in follicle ovarian reserve (FOR) in the female subject. In some embodiments, a prophylactically effective amount is less than the therapeutically effective amount (e.g., for the treatment of a subject who has or is at risk of POA or DOR. A dose of MIS or MIS protein variant for contraceptive measures (e.g., prophylactic effective amount) may be higher than the prophylactic amount for preventing a decrease in ovarian reserve (e.g., for preventing a decrease in follicle ovarian reserve (FOR). A prophylatically effective amount of a recombinant human MIS protein or functional fragment or variant thereof is also one in which any toxic or detrimental effects of the compound are outweighed by the beneficial effects.

As used herein, the terms "prevent," "preventing" and "prevention" refer to the avoidance or delay in manifestation of one or more symptoms or measurable markers of a disease or disorder, e.g., of POA or DOR (diminished ovarian reserve). A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the avoidance or prevention of a symptom or marker of the disease, but also a reduced severity or degree of any one of the symptoms or markers of the disease, relative to those symptoms or markers in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

A "composition" or "pharmaceutical composition" are used interchangeably herein refers to a composition that usually contains an excipient, such as a pharmaceutically acceptable carrier that is conventional in the art and that is suitable for administration to cells. The cells may be part of a subject, for example for therapeutic, diagnostic, or prophylactic purposes. The cells may also be cultured, for example cells as part of an assay for screening potential pharmaceutical compositions, and the cells may be part of a transgenic animal for research purposes. The composition can also be a cell culture, in which a polypeptide or polynucleotide encoding a metabolic regulator of the present invention is present in the cells and/or in the culture medium. In addition, compositions for topical (e.g., oral mucosa, respiratory mucosa) and/or oral administration can form solutions, suspensions, tablets, pills, capsules, sustained-release formulations, oral rinses, or powders, as known in the art and described herein. The compositions also can include stabilizers and preservatives. For examples of carriers, stabilizers and adjuvants, University of the Sciences in Philadelphia (2005) Remington: *The Science and Practice of Pharmacy with Facts and Comparisons,* 21st Ed.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The term "vector" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self-replicating extrachromosomal vectors or vectors which integrates into a host genome. Preferred vectors are those capable of autonomous replication and/or expression of nucleic acids to which they are linked. Vectors capable of directing the expression of genes to which they are operatively linked are referred to herein as "expression vectors". Expression vectors can result in stable or transient expression of the DNA. An exemplary expression vector for use in the present invention is pcDNA3.1.

The term "viral vectors" refers to the use as viruses, or virus-associated vectors as carriers of the nucleic acid construct into the cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g., EPV and EBV vectors.

The term "inducible vector" refers to a vector whose gene expression can be controlled. For example, the level of gene expression can be increased, decreased, or reduced to zero. In some embodiments, the inducible vector can comprise a switch that controls gene expression.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined Enhancers need not be located in close proximity to the coding sequences whose transcription they enhance. Furthermore, a gene transcribed from a promoter regulated in trans by a factor transcribed by a second promoter may be said to be operatively linked to the second promoter. In such a case, transcription of the first gene is said to be operatively linked to the first promoter and is also said to be operatively linked to the second promoter.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or up to between about 90-95% or 90-99% decrease or any decrease of at least 10%-95% or 10-99% as compared to a reference level.

The term "statistically significant" or "significantly" refers to statistical significance and generally means a two standard deviation (2SD) or greater difference.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

In some embodiments, the present invention may be defined in any of the following numbered paragraphs:

1. A method of contraception comprising administering to a female subject a composition comprising a Mullerian Inhibiting Substance (MIS) protein.
2. The method of paragraph 1, wherein the MIS protein comprises amino acid residues 26-560 of SEQ ID NO: 3 or a polypeptide which has at least 95% sequence identity to the amino acid sequence of amino acid residues 26-560 of SEQ ID NO: 3.
3. The method of paragraph 1, wherein the MIS protein comprises amino acid residues 25-559 of SEQ ID NO: 4 or a polypeptide which has at least 95% sequence identity to the amino acid sequence of amino acid residues 25-559 of SEQ ID NO: 4.
4. The method of paragraph 1, wherein the MIS protein comprises amino acid residues 25-567 of SEQ ID NO: 5 or a polypeptide which has at least 95% sequence identity to the amino acid sequence of amino acid residues 25-567 of SEQ ID NO: 5.
5. The method of any of paragraphs 1 to 4, wherein the MIS protein is produced by a vector, wherein the vector comprises a polynucleotide encoding the MIS protein operatively linked to a promoter.
6. The method of paragraph 5, wherein the vector is a viral vector.
7. The method of paragraph 6, wherein the viral vector is selected from the group consisting of; an adenoviral (Adv) vector, an AAV vector, a poxvirus vector and a lentiviral vector.
8. The method of any of paragraphs 5 to 7, wherein the polynucleotide corresponds to SEQ ID NO: 1 or a polynucleotide which has at least 95% sequence identity to the nucleic acid sequence of SEQ ID NO: 1.
9. The method of any of paragraphs 5 to 7, wherein the polynucleotide corresponds to SEQ ID NO: 2 or a polynucleotide which has at least 95% sequence identity to the nucleic acid sequence of SEQ ID NO: 2.
10. The method of any of paragraphs 1 to 9, wherein the composition further comprises a pharmaceutically acceptable carrier.
11. The method of any of paragraphs 1 to 10, wherein the female subject is an animal.
12. The method of paragraph 11, wherein the animal is a cat or a dog.
13. The method of any of paragraphs 1 to 10, wherein the female subject is a human.
14. The method of any of paragraphs 1 to 13, wherein the administering is a one-time injection.
15. The method of any of paragraphs 1 to 13, wherein the administering comprises pulse administration followed by a interval of no administration.
16. The method of any of paragraphs 1 to 13, wherein administration is subcutaneous administration, or administration via a transdermal patch, ring, biogel or injection.
17. The method of any of paragraphs 1 to 13, wherein the MIS protein is administered at sufficiently high concentrations for complete arrest in folliculogeneis in the subject.
18. The method of paragraph 17, wherein the MIS administered to the subject increases the concentration of the MIS protein in the blood of the subject by 10% to 50% higher as compared to the absence of administration of MIS.
19. The method of paragraph 17, wherein the MIS administered to the subject increases the concentration of the MIS protein in the blood of the subject by 50% to 100% higher as compared to the absence of administration of MIS.
20. The method of paragraph 17, wherein the MIS administered to the subject increases the concentration of the MIS protein in the blood of the subject by 2 to 5-fold higher or more than 5-fold as compared to the absence of administration of MIS.

21. The method of paragraph 17, wherein the MIS administered to the subject increases the concentration of the MIS protein in the blood of the subject to between 1 μg/ml-5 μg/ml.

22. A method of preventing a decline in the functional ovarian reserve (FOR) in a female subject, comprising administering to the female subject a composition comprising a Mullerian Inhibiting Substance (MIS) protein.

23. The method of paragraph 22, wherein the MIS protein comprises amino acid residues 26-560 of SEQ ID NO: 3 or a polypeptide which has at least 95% sequence identity to the amino acid sequence of amino acid residues 26-560 of SEQ ID NO: 3.

24. The method of paragraph 22, wherein the MIS protein comprises amino acid residues 25-559 of SEQ ID NO: 4 or a polypeptide which has at least 95% sequence identity to the amino acid sequence of amino acid residues 25-559 of SEQ ID NO: 4.

25. The method of paragraph 22, wherein the MIS protein comprises amino acid residues 25-567 of SEQ ID NO: 5 or a polypeptide which has at least 95% sequence identity to the amino acid sequence of amino acid residues 25-567 of SEQ ID NO: 5.

26. The method of any of paragraphs 22 to 25, wherein the MIS protein is produced by a vector, wherein the vector comprises a polynucleotide encoding the MIS protein operatively linked to a promoter.

27. The method of paragraph 26, wherein the promoter is an inducible promoter.

28. The method of paragraph 26, wherein the vector is a viral vector.

29. The method of paragraph 28, wherein the viral vector is selected from the group consisting of; an adenoviral (Adv) vector, an AAV vector, a poxvirus vector and a lentiviral vector.

30. The method of any of paragraphs 26 to 29, wherein the polynucleotide corresponds to SEQ ID NO: 1 or a polynucleotide which has at least 95% sequence identity to the nucleic acid sequence of SEQ ID NO: 1.

31. The method of any of paragraphs 26 to 29, wherein the polynucleotide corresponds to SEQ ID NO: 2 or a polynucleotide which has at least 95% sequence identity to the nucleic acid sequence of SEQ ID NO: 2.

32. The method of any of paragraphs 22 to 31, wherein the composition further comprises a pharmaceutically acceptable carrier.

33. The method of any of paragraphs 22 to 32, wherein the female subject is a human.

34. The method of any of paragraphs 22 to 33, wherein the female subject is an animal.

35. The method of any of paragraphs 22 to 34, wherein the administering is a one-time injection.

36. The method of any of paragraphs 22 to 35, wherein the administering comprises pulse administration followed by a interval of no administration.

37. The method of any of paragraphs 22 to 36, wherein administration is selected from the group consisting of: subcutaneous administration, oral administration, transdermal patch administration, intravaginal administration, administration via a ring, biogel or injection.

38. The method of any of paragraphs 22 to 37, wherein the MIS protein is administered at sufficiently high concentrations for complete arrest in folliculogeneis.

39. The method of paragraph 38, wherein the MIS administered to the subject increases the concentration of the MIS protein in the blood of the subject by 10% to 50% higher as compared to the absence of administration of MIS.

40. The method of paragraph 38, wherein the MIS administered to the subject increases the concentration of the MIS protein in the blood of the subject by 50% to 100% higher as compared to the absence of administration of MIS.

41. The method of paragraph 38, wherein the MIS administered to the subject increases the concentration of the concentration of the MIS protein in the blood of the subject by 2 to 5-fold higher or more than 5-fold as compared to the absence of administration of MIS.

42. The method of paragraph 38, wherein the MIS administered to the subject increases the concentration of the MIS protein in the blood of the subject to between 1 μg/ml-5 μg/ml.

43. The method of paragraph 36, wherein the pulsed administration comprises an interval between pulsed administration of the composition of at least 3 days.

44. The method of paragraph 36, wherein the pulsed administration comprises an interval between pulsed administration of the composition of at least 7 days.

45. The method of paragraph 36, wherein the pulsed administration comprises an interval between pulsed administration of the composition of between 7 days and 3 weeks.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

EXAMPLES

The following examples are provided for illustrative purposes only and are not intended to limit the scope of the invention.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

Example 1

AAV9-MIS Treatment in Mice

Figure 4:
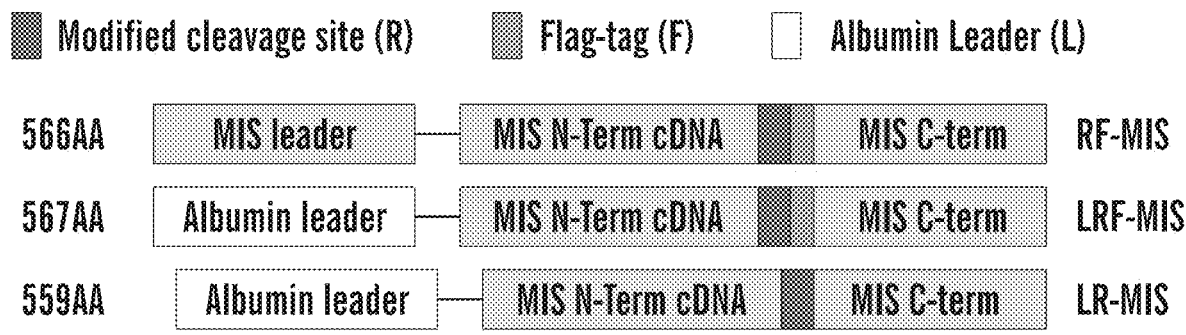
FIG. 4 is a schematic drawing showing different recombinant MIS proteins variants. The design of the RF, LRF, and LR constructs including the placement of the flag tag (F), the modified cleavage site (R), and the albumin leader sequence (L).
Figure 5:
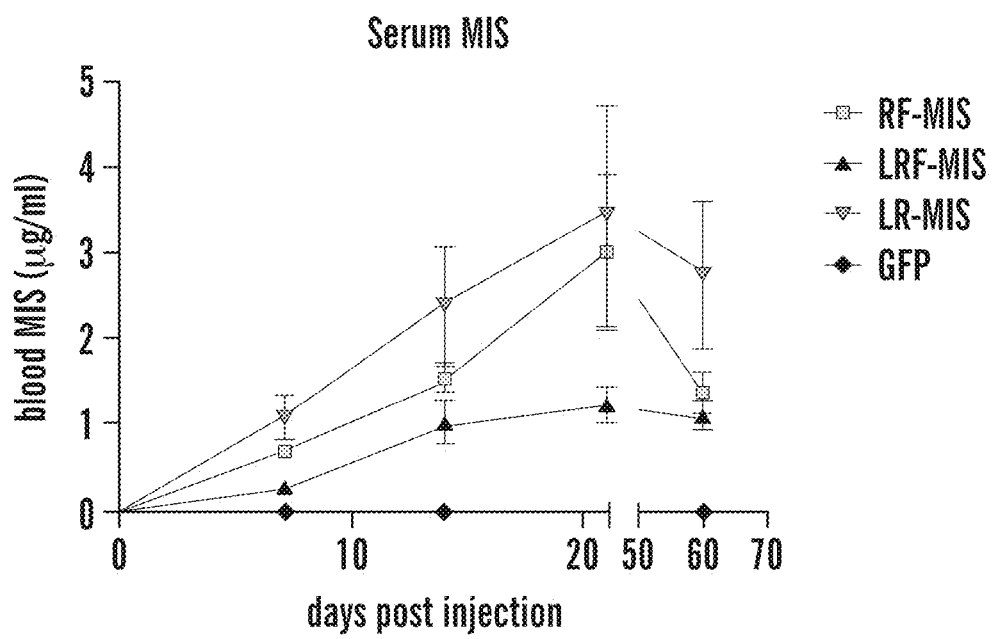
FIG. 5 shows blood levels of MIS by ELISA following a single injection of AAV9-MIS. An injection of $3 \times 10^{11}$ viral particles of AAV9-RF-MIS, AAV9-LRF-MIS, an AAV9-LR-MIS was given at day 0 and blood was monitored weekly for 60 days using an MIS ELISA. Error bars represent ±SEM.

Recently, adeno-associated viruses (AAV), which normally infect mammals, including humans, but are non-pathogenic, have been developed and employed as gene therapy vectors in clinical trials in Europe with great success. In a study, the inventors demonstrate that AAV9 expressing MIS proteins and MIS protein variants (e.g. LR-MIS, RF-MIS, LRF-MIS) (see FIG. 4) were successful, when delivered as a single dose, in causing high levels of MIS to be secreted in the blood (FIG. 5). The concentration of MIS was in the ug/ml range when $3 \times 10^{11}$ viral particles were administered intraperitoneally, and the levels were extremely stable, persisting without any reduction for the 60 day length of the experiment (FIG. 1A), and expression persists at least 6 months in mice or longer in physiologic experiments.

When injected intraperitoneally, the virus has significant tropism to the muscles of the body wall, and the pancreas as evidenced by AAV-GFP control infections. Doses from $1 \times 10^{11}$ to $1 \times 10^{12}$, can induce production of MIS in the 0.3-1.5 ug/ml range (FIG. 1A) which is sufficient for a complete block in folliculogenesis, as evidenced by the observation of a normal amount of primordial follicles, and an absence of all other stages of development (primary, secondary, antral) (FIG. 1B). The resulting AAV-MIS treated ovaries are much smaller than control treated AAV-GFP ovaries because of the lack of growing follicles (FIG. 1C), but show no evidence of toxicity and retain primordial follicles (FIG. 1C, see arrow). Similar results were observed after single injections of virus delivering Flag-tagged MIS constructs (data not shown).

Example 2

Mice treated with AAV9-LR-MIS, AAV9-LRF-MIS, or AAV9-RF-MIS had more follicles per slide (FIG. 2) and smaller ovaries (FIG. 3) than control AAV9-GFP treated mice, demonstrating the preservation of primordial ovarian follicles and inhibition of follicle maturation in the MIS-treated mice.

Further, the inventors demonstrate in vivo that mice treated with AAV9-LR-MIS were unable to get pregnant and reproduce, as shown in Table 1. In particular, C57/BL6 female mice were treated at sexual maturity (6-8 weeks) with a dose $3 \times 10^{11}$ AAV9-LR-MIS or AAV9-GFP control and observed for one month to record cycling, and to monitor MIS and steroid levels in the blood. One month after treatment, female mice were paired with a male seasoned breeder of 3-4 months of age. Cumulative time spent in mating pairs as well as cumulative litter sizes were recorded. 23 pups were produced from 3 pairs of mice treated with AAV-GFP, whereas no pups were produced from 3 pairs of mice treated with AAV9-LR-MIS (See Table 1), demonstrating that MIS protein inhibits reproduction.

Table 1 shows cumulative reproductive output of AAV9-LRMIS or AAV9-GFP control treated female mice placed in mating pairs with WT male mice.

|  | GFP control | MIS females |
|---|---|---|
| pairs | 3 | 2 |
| days | 184 | 184 |
| pups | 23 | 0 |
| pups/days/pair | 0.042 | 0.000 |

```
SEQUENCE LISTING:
SEQ ID NO: 1 LR - nucleic acid sequence
ATGAAGTGGGTGAGCTTCATCAGCCTGCTGTTCCTGTTCAGCAGCGCTTACTCCCGCGGTGTGTTCCGCCGCAGA

GCAGAGGAGCCAGCTGTGGGCACCAGTGGCCTCATCTTCCGAGAAGACTTGGACTGGCCTCCAGGCAGCCCACAA

GAGCCTCTGTGCCTGGTGGCACTGGGCGGGGACAGCAATGGCAGCAGCTCCCCCCTGCGGGTGGTGGGGGCTCTA

AGCGCCTATGAGCAGGCCTTCCTGGGGGCCGTGCAGAGGGCCCGCTGGGGCCCCCGAGACCTGGCCACCTTCGGG

GTCTGCAACACCGGTGACAGGCAGGCTGCCTTGCCCTCTCTACGGCGGCTGGGGGCCTGGCTGCGGGACCCTGGG

GGGCAGCGCCTGGTGGTCCTACACCTGGAGGAAGTGACCTGGGAGCCAACACCCTCGCTGAGGTTCCAGGAGCCC

CCGCCTGGAGGAGCTGGCCCCCCAGAGCTGGCGCTGCTGGTGCTGTACCCTGGGCCTGGCCCTGAGGTCACTGTG

ACGAGGGCTGGGCTGCCGGGTGCCCAGAGCCTCTGCCCCTCCCGAGACACCCGCTACCTGGTGTTAGCGGTGGAC

CGCCCTGCGGGGCCTGGCGCGGCTCCGGGCTGGCCTTGACCCTGCAGCCCCGCGGAGAGGACTCCCGGCTGAGT

ACCGCCCGGCTGCAGGCACTGCTGTTCGGCGACGACCACCGCTGCTTCACACGGATGACCCCGGCCCTGCTCCTG

CTGCCGCGGTCCGAGCCCGCGCCGCTGCCTGCGCACGGCCAGCTGGACACCGTGCCCTTCCCGCCGCCCAGGCCA

TCCGCGGAACTCGAGGAGTCGCCACCCAGCGCAGACCCCTTCCTGGAGACGCTCACGCGCCTGGTGCGGGCGCTG

CGGGTCCCCCCGGCCCGGGCCTCCGCGCCGCGCCTGGCCCTGGATCCGGACGCGCTGGCCGGCTTCCCGCAGGGC

CTAGTCAACCTGTCGGACCCCGCGGCGCTGGAGCGCCTACTCGACGGCGAGGAGCCGCTGCTGCTGCTGCTGAGG

CCCACTGCGGCCACCACCGGGGATCCTGCGCCCCTGCACGACCCCACGTCGGCGCCGTGGGCCACGGCCCTGGCG

CGCCGCGTGGCTGCTGAACTGCAAGCGGCGGCTGCCGAGCTGCGAAGCCTCCCGGGTCTGCCTCCGGCCACAGCC
```

-continued

CCGCTGCTGGCGCGCCTGCTCGCGCTCTGCCCAGGTGGCCCCGGCGGCCTCGGCGATCCCCTGCGAGCGCTGCTG

CTCCTGAAGGCGCTGCAGGGCCTGCGCGTGGAGTGGCGCGGGCGGGATCCGCGCGGGCCGGGTCGGGCACGGCGC

AGCGCGGGGGCCACCGCCGCCGACGGGCCGTGCGCGCTGCGCGAGCTCAGCGTAGACCTCCGCGCCGAGCGCTCC

GTACTCATCCCCGAGACCTACCAGGCCAACAATTGCCAGGGCGTGTGCGGCTGGCCTCAGTCCGACCGCAACCCG

CGCTACGGCAACCACGTGGTGCTGCTGCTGAAGATGCAGGCCCGTGGGGCCGCCCTGGCGCGCCCACCCTGCTGC

GTGCCCACCGCCTACGCGGGCAAGCTGCTCATCAGCCTGTCGGAGGAGCGCATCAGCGCGCACCACGTGCCCAAC

ATGGTGGCCACCGAGTGTGGCTGCCGGTGA

SEQ ID NO: 2 LRF - nucleic acid sequence
*ATGAAGTGGGTGAGCTTCATCAGCCTGCTGTTCCTGTTCAGCAGCGCTTACTCCCGCGGTGTGTTCCGCCGCAGA*

*GCA*GAGGAGCCAGCTGTGGGCACCAGTGGCCTCATCTTCCGAGAAGACTTGGACTGGCCTCCAGGCAGCCCACAA

GAGCCTCTGTGCCTGGTGGCACTGGGCGGGACAGCAATGGCAGCAGCTCCCCCCTGCGGGTGGTGGGGGCTCTA

AGCGCCTATGAGCAGGCCTTCCTGGGGGCCGTGCAGAGGGCCCGCTGGGGCCCCCGAGACCTGGCCACCTTCGGG

GTCTGCAACACCGGTGACAGGCAGGCTGCCTTGCCCTCTCTACGGCGGCTGGGGCCTGGCTGCGGGACCCTGGG

GGGCAGCGCCTGGTGGTCCTACACCTGGAGGAAGTGACCTGGGAGCCAACACCCTCGCTGAGGTTCCAGGAGCCC

CCGCCTGGAGGAGCTGGCCCCCCAGAGCTGGCGCTGCTGGTGCTGTACCCTGGGCCTGGCCCTGAGGTCACTGTG

ACGAGGGCTGGGCTGCCGGGTGCCCAGAGCCTCTGCCCCTCCCGAGACACCCGCTACCTGGTGTTAGCGGTGGAC

CGCCCTGCGGGGCCTGGCGCGGCTCCGGGCTGGCCTTGACCCTGCAGCCCCGCGGAGAGGACTCCCGGCTGAGT

ACCGCCCGGCTGCAGGCACTGCTGTTCGGCGACGACCACCGCTGCTTCACACGGATGACCCCGGCCCTGCTCCTG

CTGCCGCGGTCCGAGCCCGCGCCGCTGCCTGCGCACGGCCAGCTGGACACCGTGCCCTTCCCGCCGCCCAGGCCA

TCCGCGGAACTCGAGGAGTCGCCACCCAGCGCAGACCCCTTCCTGGAGACGCTCACGCGCCTGGTGCGGGCGCTG

CGGGTCCCCCCGGCCCGGGCCTCCGCGCCGCGCCTGGCCCTGGATCCGGACGCGCTGGCCGGCTTCCCGCAGGGC

CTAGTCAACCTGTCGGACCCCGCGGCGCTGGAGCGCCTACTCGACGGCGAGGAGCCGCTGCTGCTGCTGCTGAGG

CCCACTGCGGCCACCACCGGGGATCCTGCGCCCCTGCACGACCCCACGTCGGCGCCGTGGGCCACGGCCCTGGCG

CGCCGCGTGGCTGCTGAACTGCAAGCGGCGGCTGCCGAGCTGCGAAGCCTCCCGGGTCTGCCTCCGGCCACAGCC

CCGCTGCTGGCGCGCCTGCTCGCGCTCTGCCCAGGTGGCCCCGGCGGCCTCGGCGATCCCCTGCGAGCGCTGCTG

CTCCTGAAGGCGCTGCAGGGCCTGCGCGTGGAGTGGCGCGGGCGGGATCCGCGCGGGCCGGGTCGGGCACGGCGC

AGCgactacaaggatgacgacgacaagGCGGGGGCCACCGCCGCCGACGGGCCGTGCGCGCTGCGCGAGCTCAGC

GTAGACCTCCGCGCCGAGCGCTCCGTACTCATCCCCGAGACCTACCAGGCCAACAATTGCCAGGGCGTGTGCGGC

TGGCCTCAGTCCGACCGCAACCCGCGCTACGGCAACCACGTGGTGCTGCTGCTGAAGATGCAGGCCCGTGGGGCC

GCCCTGGCGCGCCCACCCTGCTGCGTGCCCACCGCCTACGCGGGCAAGCTGCTCATCAGCCTGTCGGAGGAGCGC

ATCAGCGCGCACCACGTGCCCAACATGGTGGCCACCGAGTGTGGCTGCCGGTGA

SEQ ID NO: 3 MIS (560AA) - amino acid sequence (underlined
identifies native MIS leader sequence)
<u>mrdlpltsla lvlsalgall gtealraeep</u> avgtsglifr edldwppgsp geplclvalg gdsngssspl rvvgalsaye qaflgavgra rwgprdlatf gvcntgdrqa alpslrrlga wirdpggqrl vvlhleevtw eptpslrfqe pppggagppe lallvlypgp gpevtvtrag lpgagslcps rdtrylvlav drpagawrgs glaltlqprg edsrlstarl qallfgddhr cftrmtpall llprsepapl pahgqldtvp fppprpsael eesppsadpf letltrlvra lrvpparasa prlaldpdal agfpgglvnl sdpaalerll dgeeplllll rptaattgdp aplhdptsap watalarrva aelqaaaael rslpglppat apllarllal cpggpgglgd -continued plrallllka lqglrvewrg rdprgpgraq rsagataadg pcalrelsvd lraersvlip etyqanncqg vcgwpqsdrn prygnhvvll lkmqvrgaal arppccvpta yagkllisls eerisahhvp nmvatecgcr SEQ ID NO: 4 LR (559AA) BOLD red indicates-albumin leader
sequence; green-identifies the Modified cleavage site
mkwvtfisll flfssaysrg vfrr raeep avgtsglifr edldwppgsp qeplclvalg gdsngssspl rvvgalsaye qaflgavgra rwgprdlatf gvcntgdrqa alpslrrlga wlrdpggqrl vvlhleevtw eptpslrfqe pppggagppe lallvlypgp gpevtvtrag lpgagslcps rdtrylvlav drpagawrgs glaltlqprg edsrlstarl qallfgddhr cftrmtpall llprsepapl pahgqldtvp fppprpsael eesppsadpf letltrlvra lrvpparasa prlaldpdal agfpgglvnl sdpaalerll dgeeplllll rptaattgdp aplhdptsap watalarrva aelqaaaael rslpglppat apllarllal cpggpgglgd plrallllka lqglrvewrg rdprgpgra<u>R</u> rsagataadg pcalrelsvd lraersvlip etyqanncqg vcgwpqsdrn prygnhvvll lkmqvrgaal arppccvpta yagkllisls eerisahhvp nmvatecgcr SEQ ID NO: 5 LRF (567AA) highlighted-Flag tag (DYKDDDDK)
mkwvtfisll flfssaysrg vfrr raeep avgtsglifr edldwppgsp qeplclvalg gdsngssspl rvvgalsaye qaflgavgra rwgprdlatf gvcntgdrqa alpslrrlga wlrdpggqrl vvlhleevtw eptpslrfqe pppggagppe lallvlypgp gpevtvtrag lpgagslcps rdtrylvlav drpagawrgs glaltlqprg edsrlstarl qallfgddhr cftrmtpall llprsepapl pahgqldtvp fppprpsael eesppsadpf letltrlvra lrvpparasa prlaldpdal agfpgglvnl sdpaalerll dgeeplllll rptaattgdp aplhdptsap watalarrva aelqaaaael rslpglppat apllarllal cpggpgglgd plrallllka lqglrvewrg rdprgpgra<u>R</u> rs*DYKDDDDK* agataadg pcalrelsvd lraersvlip etyqanncqg vcgwpqsdrn prygnhvvll lkmqvrgaal arppccvpta yagkllisls eerisahhvp nmvatecgcr SEQ ID NO: 6: amino acid sequence of HSA leader sequence
mkwvtfisll flfssaysrg vfrr SEQ ID NO: 7: nucleic acid of HSA leader sequence
*ATGAAGTGGGTGAGCTTCATCAGCCTGCTGTTCCTGTTCAGCAGCGCTTACTCCCGCGGTGTGTTCCGCCGCAGA*

*GCA*

SEQ ID NO: 21 - amino acid sequence of Flag Tag
*DYKDDDDK*

SEQ ID NO: 22 - nucleic acid sequence of Flag Tag
gactacaaggatgacgacgacaag

---

The invention claimed is:

1. A method of permanent contraception in a female cat comprising administering to the female cat an effective amount of a composition comprising a viral vector comprising one or more regulatory elements operatively linked to a nucleic acid encoding a wild-type Mullerian Inhibiting Substance (MIS) protein for permanent contraception in the female cat, wherein the effective amount of the composition administered to the female cat increases the concentration of MIS protein in the blood of the female cat to a MIS serum concentration of about 0.3 µg/ml to about 5 µg/ml.

2. The method of claim 1, wherein the MIS protein is a wild-type feline MIS protein.

3. The method of claim 2, wherein the viral vector is an AAV vector.

4. The method of claim 1, wherein the viral vector is an adenoviral vector, an adeno-associated virus (AAV) vector, a poxvirus vector, or a lentiviral vector.

5. The method of claim 1, wherein the viral vector is an AAV vector.

6. The method of claim 1, wherein the one or more regulatory elements comprise a promoter element.

7. The method of claim 1, wherein the one or more regulatory elements comprise a promoter element and an enhancer element.

8. The method of claim 1, wherein the one or more regulatory elements comprise a constitutively active promoter.

9. The method of claim 1, wherein the composition further comprises a pharmaceutically acceptable carrier.

10. The method of claim 1, wherein the administering is a one-time injection.

11. The method of claim 1, wherein the administering is via injection.

12. The method of claim 1, wherein the administering is intravenous, subcutaneous, or intramuscular administration.

13. The method of claim 1, wherein the administering is intramuscular administration.

14. A method of arresting folliculogenesis in a female cat comprising administering to the female cat an effective amount of a composition comprising a viral vector comprising one or more regulatory elements operatively linked to a nucleic acid encoding a wild-type Mullerian Inhibiting Substance (MIS) protein, wherein folliculogenesis is arrested in the female cat, wherein the effective amount of the composition administered to the female cat increases the concentration of MIS protein in the blood of the female cat to a MIS serum concentration of about 0.3 µg/ml to about 5 µg/ml.

15. The method of claim 14, wherein the MIS protein is a wild-type feline MIS protein.

16. The method of claim 14, wherein the viral vector is an adenoviral vector, an adeno-associated virus (AAV) vector, a poxvirus vector, or a lentiviral vector.

17. The method of claim 15, wherein the viral vector is an AAV vector.

18. The method of claim 14, wherein the administering is a one-time injection.

19. The method of claim 14, wherein the administering is intravenous, subcutaneous, or intramuscular administration.

20. A method of permanent contraception in a female cat comprising administering to the female cat an effective amount of a composition comprising a viral vector comprising one or more regulatory elements operatively linked to a nucleic acid encoding a wild-type Mullerian Inhibiting Substance (MIS) protein for permanent contraception in the female cat, wherein the effective amount of the composition administered to the female cat increases the concentration of MIS protein in the blood of the female cat to a MIS serum concentration of about 0.3 µg/ml to about 1.5 µg/ml.

21. The method of claim 20, wherein the MIS protein is a wild-type feline MIS protein.

22. The method of claim 20, wherein the viral vector is an adenoviral vector, an adeno-associated virus (AAV) vector, a poxvirus vector, or a lentiviral vector.

23. The method of claim 20, wherein the viral vector is an AAV vector.

24. The method of claim 20, wherein the one or more regulatory elements comprise a promoter element.

25. The method of claim 20, wherein the one or more regulatory elements comprise a promoter element and an enhancer element.

26. The method of claim 20, wherein the one or more regulatory elements comprise a constitutively active promoter.

27. The method of claim 20, wherein the composition further comprises a pharmaceutically acceptable carrier.

28. The method of claim 20, wherein the administering is a one-time injection.

29. The method of claim 20, wherein the administering is via injection.

30. The method of claim 20, wherein the administering is intravenous, subcutaneous, or intramuscular administration.

31. The method of claim 20, wherein the administering is intramuscular administration.

* * * * *

SEQUENCE LISTING

<160> NUMBER OF SEQ IDS: 23

<210> SEQ ID NO 1
<211> LENGTH: 1680
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | |
|---|---|
| atgaagtggg tgagcttcat cagcctgctg ttcctgttca gcagcgctta ctcccgcggt | 60 |
| gtgttccgcc gcagagcaga ggagccagct gtgggcacca gtggcctcat cttccgagaa | 120 |
| gacttggact ggcctccagg cagcccacaa gagcctctgt gcctggtggc actgggcggg | 180 |
| gacagcaatg gcagcagctc ccccctgcgg gtggtggggg ctctaagcgc ctatgagcag | 240 |
| gccttcctgg gggccgtgca gagggcccgc tggggccccc gagacctggc caccttcggg | 300 |
| gtctgcaaca ccggtgacag gcaggctgcc ttgccctctc tacggcggct gggggcctgg | 360 |
| ctgcgggacc ctgggggca gcgcctggtg gtcctacacc tggaggaagt gacctgggag | 420 |
| ccaacaccct cgctgaggtt ccaggagccc ccgcctggag gagctggccc ccagagctg | 480 |
| gcgctgctgg tgctgtaccc tgggcctggc cctgaggtca ctgtgacgag ggctgggctg | 540 |
| ccgggtgccc agagcctctg cccctcccga cacccgct acctggtgtt agcggtggac | 600 |
| cgccctgcgg gggcctggcg cggctcgggg ctggccttga ccctgcagcc ccgcggagag | 660 |
| gactcccggc tgagtaccgc ccggctgcag gcactgctgt tcggcgacga ccaccgctgc | 720 |
| ttcacacgga tgaccccggc cctgctcctg ctgccgcggt ccgagcccgc gccgctgcct | 780 |
| gcgcacggcc agctggacac cgtgcccttc ccgccgccca ggccatccgc ggaactcgag | 840 |
| gagtcgccac ccagcgcaga ccccttcctg agacgctca cgcgcctggt gcgggcgctg | 900 |
| cgggtccccc cggccgggc ctccgcgccg cgcctggccc tggatccgga cgcgctggcc | 960 |
| ggcttcccgc agggcctagt caacctgtcg gaccccgcgg cgctggagcg cctactcgac | 1020 |
| ggcgaggagc cgctgctgct gctgctgagg cccactgcgg ccaccaccgg ggatcctgcg | 1080 |
| cccctgcacg accccacgtc ggcgccgtgg gccacgcgcc tggcgcgccg cgtggctgct | 1140 |
| gaactgcaag cggcggctgc cgagctgcga agcctcccgg gtctgcctcc ggccacagcc | 1200 |
| ccgctgctgg cgcgcctgct cgcgctctgc ccaggtggcc ccggcggcct cggcgatccc | 1260 |
| ctgcgagcgc tgctgctcct gaaggcgctg cagggcctgc gcgtggagtg gcgcgggcgg | 1320 |
| gatccgcgcg gccggggtcg ggcacggcgc agcgcggggg ccaccgccgc cgacgggccg | 1380 |
| tgcgcgctgc gcgagctcag cgtagacctc cgcgccgagc gctccgtact catccccgag | 1440 |
| acctaccagg ccaacaattg ccagggcgtg tgcggctggc ctcagtccga ccgcaacccg | 1500 |
| cgctacggca accacgtggt gctgctgctg aagatgcagg cccgtggggc cgccctggcg | 1560 |
| cgcccacccct gctgcgtgcc caccgcctac gcgggcaagc tgctcatcag cctgtcggag | 1620 |
| gagcgcatca gcgcgcacca cgtgcccaac atggtggcca ccgagtgtgg ctgccggtga | 1680 |

```
<210> SEQ ID NO 2
<211> LENGTH: 1704
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
```

| | |
|---|---|
| atgaagtggg tgagcttcat cagcctgctg ttcctgttca gcagcgctta ctcccgcggt | 60 |
| gtgttccgcc gcagagcaga ggagccagct gtgggcacca gtggcctcat cttccgagaa | 120 |
| gacttggact ggcctccagg cagcccacaa gagcctctgt gcctggtggc actgggcggg | 180 |
| gacagcaatg gcagcagctc ccccctgcgg gtggtggggg ctctaagcgc ctatgagcag | 240 |
| gccttcctgg gggccgtgca gagggcccgc tggggccccc gagacctggc caccttcggg | 300 |
| gtctgcaaca ccggtgacag gcaggctgcc ttgccctctc tacggcggct gggggcctgg | 360 |

```
ctgcgggacc ctgggggggca gcgcctggtg gtcctacacc tggaggaagt gacctgggag    420
ccaacaccct cgctgaggtt ccaggagccc ccgcctggag gagctggccc cccagagctg    480
gcgctgctgg tgctgtaccc tgggcctggc cctgaggtca ctgtgacgag ggctgggctg    540
ccgggtgccc agagcctctg cccctcccga cacccgct acctggtgtt agcggtggac      600
cgccctgcgg gggcctggcg cggctccggg ctggccttga ccctgcagcc ccgcggagag    660
gactcccggc tgagtaccgc ccggctgcag gcactgctgt tcggcgacga ccaccgctgc    720
ttcacacgga tgaccccggc cctgctcctg ctgccgcggt ccgagcccgc gccgctgcct    780
gcgcacggcc agctggacac cgtgcccttc ccgccgccca ggccatccgc ggaactcgag    840
gagtcgccac ccagcgcaga ccccttcctg gagacgctca cgcgcctggt gcgggcgctg    900
cgggtccccc cggcccggc ctccgcgccc cgcctggccc tggatccgga cgcgctggcc     960
ggcttcccgc agggcctagt caacctgtcg gaccccgcgg cgctggagcg cctactcgac   1020
ggcgaggagc cgctgctgct gctgctgagg cccactgcgg ccaccaccgg ggatcctgcg   1080
cccctgcacg accccacgtc ggcgccgtgg gccacggccc tggcgcgccg cgtggctgct   1140
gaactgcaag cggcggctgc cgagctgcga agcctcccgg gtctgcctcc ggccacagcc   1200
ccgctgctgg cgcgcctgct cgcgctctgc ccaggtggcc ccggcggcct cggcgatccc   1260
ctgcgagcgc tgctgctcct gaaggcgctg cagggcctgc gcgtggagtg cgcgggcgg    1320 gatccgcgcg ggccgggtcg ggcacggcgc agcgactaca aggatgacga cgacaaggcg   1380
ggggccaccg ccgccgacgg gccgtgcgcg ctgcgcgagc tcagcgtaga cctccgcgcc   1440
gagcgctccg tactcatccc cgagacctac caggccaaca attgccaggg cgtgtgcggc   1500
tggcctcagt ccgaccgcaa cccgcgctac ggcaaccacg tggtgctgct gctgaagatg   1560
caggcccgtg gggccgccct ggcgcgccca ccctgctgcg tgcccaccgc ctacgcgggc   1620
aagctgctca tcagcctgtc ggaggagcgc atcagcgcgc accacgtgcc caacatggtg   1680
gccaccgagt gtggctgccg gtga                                           1704
```

<210> SEQ ID NO 3
<211> LENGTH: 560
<212> TYPE: PRT
<213> ORGANISM: Homo sapiens

<400> SEQUENCE: 3

```
Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
```

-continued

```
            130              135              140
Ser Leu Arg Phe Gln Glu Pro Pro Gly Gly Ala Gly Pro Glu
145                  150                  155              160

Leu Ala Leu Leu Val Leu Tyr Pro Gly Pro Gly Pro Glu Val Thr Val
                165                  170                  175

Thr Arg Ala Gly Leu Pro Gly Ala Gln Ser Leu Cys Pro Ser Arg Asp
                180                  185                  190

Thr Arg Tyr Leu Val Leu Ala Val Asp Arg Pro Ala Gly Ala Trp Arg
                195                  200                  205

Gly Ser Gly Leu Ala Leu Thr Leu Gln Pro Arg Gly Glu Asp Ser Arg
210                  215                  220

Leu Ser Thr Ala Arg Leu Gln Ala Leu Leu Phe Gly Asp Asp His Arg
225                  230                  235                  240

Cys Phe Thr Arg Met Thr Pro Ala Leu Leu Leu Leu Pro Arg Ser Glu
                245                  250                  255

Pro Ala Pro Leu Pro Ala His Gly Gln Leu Asp Thr Val Pro Phe Pro
                260                  265                  270

Pro Pro Arg Pro Ser Ala Glu Leu Glu Glu Ser Pro Pro Ser Ala Asp
                275                  280                  285

Pro Phe Leu Glu Thr Leu Thr Arg Leu Val Arg Ala Leu Arg Val Pro
                290                  295                  300

Pro Ala Arg Ala Ser Ala Pro Arg Leu Ala Leu Asp Pro Asp Ala Leu
305                  310                  315                  320

Ala Gly Phe Pro Gln Gly Leu Val Asn Leu Ser Asp Pro Ala Ala Leu
                325                  330                  335

Glu Arg Leu Leu Asp Gly Glu Glu Pro Leu Leu Leu Leu Arg Pro
                340                  345                  350

Thr Ala Ala Thr Thr Gly Asp Pro Ala Pro Leu His Asp Pro Thr Ser
                355                  360                  365

Ala Pro Trp Ala Thr Ala Leu Ala Arg Arg Val Ala Ala Glu Leu Gln
                370                  375                  380

Ala Ala Ala Ala Glu Leu Arg Ser Leu Pro Gly Leu Pro Pro Ala Thr
385                  390                  395                  400

Ala Pro Leu Leu Ala Arg Leu Leu Ala Leu Cys Pro Gly Gly Pro Gly
                405                  410                  415

Gly Leu Gly Asp Pro Leu Arg Ala Leu Leu Leu Lys Ala Leu Gln
                420                  425                  430

Gly Leu Arg Val Glu Trp Arg Gly Arg Asp Pro Arg Gly Pro Gly Arg
                435                  440                  445

Ala Gln Arg Ser Ala Gly Ala Thr Ala Ala Asp Gly Pro Cys Ala Leu
450                  455                  460

Arg Glu Leu Ser Val Asp Leu Arg Ala Glu Ser Val Leu Ile Pro
465                  470                  475                  480

Glu Thr Tyr Gln Ala Asn Asn Cys Gln Gly Val Cys Gly Trp Pro Gln
                485                  490                  495

Ser Asp Arg Asn Pro Arg Tyr Gly Asn His Val Val Leu Leu Leu Lys
                500                  505                  510

Met Gln Val Arg Gly Ala Ala Leu Ala Arg Pro Cys Cys Val Pro
                515                  520                  525

Thr Ala Tyr Ala Gly Lys Leu Leu Ile Ser Leu Ser Glu Glu Arg Ile
                530                  535                  540

Ser Ala His His Val Pro Asn Met Val Ala Thr Glu Cys Gly Cys Arg
545                  550                  555                  560
```

<210> SEQ ID NO 4
<211> LENGTH: 559
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

Met Lys Trp Val Thr Phe Ile Ser Leu Leu Phe Leu Phe Ser Ser Ala
1               5                   10                  15

Tyr Ser Arg Gly Val Phe Arg Arg Ala Glu Glu Pro Ala Val Gly
            20                  25                  30

Thr Ser Gly Leu Ile Phe Arg Glu Asp Leu Asp Trp Pro Pro Gly Ser
        35                  40                  45

Pro Gln Glu Pro Leu Cys Leu Val Ala Leu Gly Asp Ser Asn Gly
    50                  55                  60

Ser Ser Ser Pro Leu Arg Val Val Gly Ala Leu Ser Ala Tyr Glu Gln
65                  70                  75                  80

Ala Phe Leu Gly Ala Val Gln Arg Ala Arg Trp Gly Pro Arg Asp Leu
                85                  90                  95

Ala Thr Phe Gly Val Cys Asn Thr Gly Asp Arg Gln Ala Ala Leu Pro
            100                 105                 110

Ser Leu Arg Arg Leu Gly Ala Trp Leu Arg Asp Pro Gly Gly Gln Arg
        115                 120                 125

Leu Val Val Leu His Leu Glu Glu Val Thr Trp Glu Pro Thr Pro Ser
130                 135                 140

Leu Arg Phe Gln Glu Pro Pro Gly Gly Ala Gly Pro Pro Glu Leu
145                 150                 155                 160

Ala Leu Leu Val Leu Tyr Pro Gly Pro Gly Pro Glu Val Thr Val Thr
                165                 170                 175

Arg Ala Gly Leu Pro Gly Ala Gln Ser Leu Cys Pro Ser Arg Asp Thr
            180                 185                 190

Arg Tyr Leu Val Leu Ala Val Asp Arg Pro Ala Gly Ala Trp Arg Gly
        195                 200                 205

Ser Gly Leu Ala Leu Thr Leu Gln Pro Arg Gly Glu Asp Ser Arg Leu
    210                 215                 220

Ser Thr Ala Arg Leu Gln Ala Leu Leu Phe Gly Asp Asp His Arg Cys
225                 230                 235                 240

Phe Thr Arg Met Thr Pro Ala Leu Leu Leu Pro Arg Ser Glu Pro
                245                 250                 255

Ala Pro Leu Pro Ala His Gly Gln Leu Asp Thr Val Pro Phe Pro Pro
            260                 265                 270

Pro Arg Pro Ser Ala Glu Leu Glu Glu Ser Pro Pro Ser Ala Asp Pro
        275                 280                 285

Phe Leu Glu Thr Leu Thr Arg Leu Val Arg Ala Leu Arg Val Pro Pro
    290                 295                 300

Ala Arg Ala Ser Ala Pro Arg Leu Ala Leu Asp Pro Asp Ala Leu Ala
305                 310                 315                 320

Gly Phe Pro Gln Gly Leu Val Asn Leu Ser Asp Pro Ala Ala Leu Glu
                325                 330                 335

Arg Leu Leu Asp Gly Glu Glu Pro Leu Leu Leu Leu Arg Pro Thr
            340                 345                 350

Ala Ala Thr Thr Gly Asp Pro Ala Pro Leu His Asp Pro Thr Ser Ala

```
                355                 360                 365
Pro Trp Ala Thr Ala Leu Ala Arg Arg Val Ala Ala Glu Leu Gln Ala
370                 375                 380

Ala Ala Ala Glu Leu Arg Ser Leu Pro Gly Leu Pro Pro Ala Thr Ala
385                 390                 395                 400

Pro Leu Leu Ala Arg Leu Leu Ala Leu Cys Pro Gly Gly Pro Gly Gly
                405                 410                 415

Leu Gly Asp Pro Leu Arg Ala Leu Leu Leu Lys Ala Leu Gln Gly
            420                 425                 430

Leu Arg Val Glu Trp Arg Gly Arg Asp Pro Arg Gly Pro Gly Arg Ala
            435                 440                 445

Arg Arg Ser Ala Gly Ala Thr Ala Ala Asp Gly Pro Cys Ala Leu Arg
450                 455                 460

Glu Leu Ser Val Asp Leu Arg Ala Glu Arg Ser Val Leu Ile Pro Glu
465                 470                 475                 480

Thr Tyr Gln Ala Asn Asn Cys Gln Gly Val Cys Gly Trp Pro Gln Ser
                485                 490                 495

Asp Arg Asn Pro Arg Tyr Gly Asn His Val Val Leu Leu Lys Met
            500                 505                 510

Gln Val Arg Gly Ala Ala Leu Ala Arg Pro Pro Cys Cys Val Pro Thr
            515                 520                 525

Ala Tyr Ala Gly Lys Leu Leu Ile Ser Leu Ser Glu Glu Arg Ile Ser
530                 535                 540

Ala His His Val Pro Asn Met Val Ala Thr Glu Cys Gly Cys Arg
545                 550                 555

<210> SEQ ID NO 5
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Trp Val Thr Phe Ile Ser Leu Leu Phe Leu Phe Ser Ser Ala
1               5                   10                  15

Tyr Ser Arg Gly Val Phe Arg Arg Ala Glu Glu Pro Ala Val Gly
            20                  25                  30

Thr Ser Gly Leu Ile Phe Arg Glu Asp Leu Asp Trp Pro Pro Gly Ser
            35                  40                  45

Pro Gln Glu Pro Leu Cys Leu Val Ala Leu Gly Gly Asp Ser Asn Gly
50                  55                  60

Ser Ser Ser Pro Leu Arg Val Val Gly Ala Leu Ser Ala Tyr Glu Gln
65                  70                  75                  80

Ala Phe Leu Gly Ala Val Gln Arg Ala Arg Trp Gly Pro Arg Asp Leu
                85                  90                  95

Ala Thr Phe Gly Val Cys Asn Thr Gly Asp Arg Gln Ala Ala Leu Pro
            100                 105                 110

Ser Leu Arg Arg Leu Gly Ala Trp Leu Arg Asp Pro Gly Gly Gln Arg
            115                 120                 125

Leu Val Val Leu His Leu Glu Glu Val Thr Trp Glu Pro Thr Pro Ser
130                 135                 140

Leu Arg Phe Gln Glu Pro Pro Pro Gly Gly Ala Gly Pro Pro Glu Leu
145                 150                 155                 160
```

```
Ala Leu Leu Val Leu Tyr Pro Gly Pro Gly Pro Glu Val Thr Val Thr
                165                 170                 175

Arg Ala Gly Leu Pro Gly Ala Gln Ser Leu Cys Pro Ser Arg Asp Thr
            180                 185                 190

Arg Tyr Leu Val Leu Ala Val Asp Arg Pro Ala Gly Ala Trp Arg Gly
        195                 200                 205

Ser Gly Leu Ala Leu Thr Leu Gln Pro Arg Gly Glu Asp Ser Arg Leu
    210                 215                 220

Ser Thr Ala Arg Leu Gln Ala Leu Leu Phe Gly Asp Asp His Arg Cys
225                 230                 235                 240

Phe Thr Arg Met Thr Pro Ala Leu Leu Leu Pro Arg Ser Glu Pro
                245                 250                 255

Ala Pro Leu Pro Ala His Gly Gln Leu Asp Thr Val Pro Phe Pro Pro
            260                 265                 270

Pro Arg Pro Ser Ala Glu Leu Glu Glu Ser Pro Pro Ser Ala Asp Pro
        275                 280                 285

Phe Leu Glu Thr Leu Thr Arg Leu Val Arg Ala Leu Arg Val Pro Pro
    290                 295                 300

Ala Arg Ala Ser Ala Pro Arg Leu Ala Leu Asp Pro Asp Ala Leu Ala
305                 310                 315                 320

Gly Phe Pro Gln Gly Leu Val Asn Leu Ser Asp Pro Ala Ala Leu Glu
                325                 330                 335

Arg Leu Leu Asp Gly Glu Glu Pro Leu Leu Leu Leu Arg Pro Thr
            340                 345                 350

Ala Ala Thr Thr Gly Asp Pro Ala Pro Leu His Asp Pro Thr Ser Ala
        355                 360                 365

Pro Trp Ala Thr Ala Leu Ala Arg Arg Val Ala Ala Glu Leu Gln Ala
    370                 375                 380

Ala Ala Ala Glu Leu Arg Ser Leu Pro Gly Leu Pro Pro Ala Thr Ala
385                 390                 395                 400

Pro Leu Leu Ala Arg Leu Leu Ala Leu Cys Pro Gly Gly Pro Gly Gly
                405                 410                 415

Leu Gly Asp Pro Leu Arg Ala Leu Leu Leu Lys Ala Leu Gln Gly
            420                 425                 430

Leu Arg Val Glu Trp Arg Gly Arg Asp Pro Arg Gly Pro Gly Arg Ala
    435                 440                 445

Arg Arg Ser Asp Tyr Lys Asp Asp Asp Lys Ala Gly Ala Thr Ala
450                 455                 460

Ala Asp Gly Pro Cys Ala Leu Arg Glu Leu Ser Val Asp Leu Arg Ala
465                 470                 475                 480

Glu Arg Ser Val Leu Ile Pro Glu Thr Tyr Gln Ala Asn Asn Cys Gln
                485                 490                 495

Gly Val Cys Gly Trp Pro Gln Ser Asp Arg Asn Pro Arg Tyr Gly Asn
            500                 505                 510

His Val Val Leu Leu Leu Lys Met Gln Val Arg Gly Ala Ala Leu Ala
        515                 520                 525

Arg Pro Pro Cys Cys Val Pro Thr Ala Tyr Ala Gly Lys Leu Leu Ile
    530                 535                 540

Ser Leu Ser Glu Glu Arg Ile Ser Ala His His Val Pro Asn Met Val
545                 550                 555                 560

Ala Thr Glu Cys Gly Cys Arg
                565
```

```
<210> SEQ ID NO 6
<211> LENGTH: 24
<212> TYPE: PRT
<213> ORGANISM: Homo sapiens

<400> SEQUENCE: 6

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 7
<211> LENGTH: 78
<212> TYPE: DNA
<213> ORGANISM: Homo sapiens

<400> SEQUENCE: 7
atgaagtggg tgagcttcat cagcctgctg ttcctgttca gcagcgctta ctcccgcggt    60
gtgttccgcc gcagagca                                                  78

<210> SEQ ID NO 8
<211> LENGTH: 18
<212> TYPE: PRT
<213> ORGANISM: Homo sapiens

<400> SEQUENCE: 8

Met Lys Trp Val Thr Phe Ile Ser Leu Leu Phe Leu Phe Ser Ser Ala
1               5                   10                  15

Tyr Ser

<210> SEQ ID NO 9
<211> LENGTH: 18
<212> TYPE: PRT
<213> ORGANISM: Homo sapiens

<400> SEQUENCE: 9

Met Lys Trp Val Thr Phe Ile Ser Leu Leu Phe Leu Phe Ser Ser Ala
1               5                   10                  15

Tyr Ser

<210> SEQ ID NO 10
<211> LENGTH: 18
<212> TYPE: PRT
<213> ORGANISM: Homo sapiens

<400> SEQUENCE: 10

Met Lys Trp Val Ser Phe Ile Ser Leu Leu Phe Leu Phe Ser Ser Ala
1               5                   10                  15

Tyr Ser

<210> SEQ ID NO 11
<211> LENGTH: 21
<212> TYPE: PRT
<213> ORGANISM: Homo sapiens

<400> SEQUENCE: 11

Met Lys Val Ser Val Ala Ala Leu Ser Cys Leu Met Leu Val Thr Ala
1               5                   10                  15

Leu Gly Ser Gln Ala
            20
```

-continued

```
<210> SEQ ID NO 12
<211> LENGTH: 17
<212> TYPE: PRT
<213> ORGANISM: Unknown
<220> FEATURE:
<223> OTHER INFORMATION: Description of Unknown: Stanniocalcin signal
      sequence

<400> SEQUENCE: 12

Met Leu Gln Asn Ser Ala Val Leu Leu Leu Val Ile Ser Ala Ser
1               5                   10                  15

Ala

<210> SEQ ID NO 13
<211> LENGTH: 19
<212> TYPE: PRT
<213> ORGANISM: Unknown
<220> FEATURE:
<223> OTHER INFORMATION: Description of Unknown: Invertase signal
      sequence

<400> SEQUENCE: 13

Met Leu Leu Gln Ala Phe Leu Phe Leu Leu Ala Gly Phe Ala Ala Lys
1               5                   10                  15

Ile Ser Ala

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Lys Trp Val Ser Phe Ile Ser Leu Leu Phe Leu Phe Ser Ser Ala
1               5                   10                  15

Tyr Ser Arg Ser Leu Glu Lys Arg
            20

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Lys Trp Val Ser Phe Ile Ser Leu Leu Phe Leu Phe Ser Ser Ala
1               5                   10                  15

Tyr Ser Arg Ser Leu Asp Lys Arg
            20

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Asn Ile Phe Tyr Ile Phe Leu Phe Leu Leu Ser Phe Val Gln Gly
1               5                   10                  15
```

```
Ser Leu Asp Lys Arg
            20

<210> SEQ ID NO 17
<211> LENGTH: 19
<212> TYPE: PRT
<213> ORGANISM: Unknown
<220> FEATURE:
<223> OTHER INFORMATION: Description of Unknown: Immunoglobulin Ig
      signal sequence

<400> SEQUENCE: 17

Met Gly Trp Ser Cys Ile Ile Leu Phe Leu Val Ala Thr Ala Thr Gly
1               5                   10                  15

Val His Ser

<210> SEQ ID NO 18
<211> LENGTH: 29
<212> TYPE: PRT
<213> ORGANISM: Unknown
<220> FEATURE:
<223> OTHER INFORMATION: Description of Unknown: Fibulin B precursor
      signal sequence

<400> SEQUENCE: 18

Met Glu Arg Ala Ala Pro Ser Arg Arg Val Pro Leu Pro Leu Leu Leu
1               5                   10                  15

Leu Gly Gly Leu Ala Leu Leu Ala Ala Gly Val Asp Ala
            20                  25

<210> SEQ ID NO 19
<211> LENGTH: 22
<212> TYPE: PRT
<213> ORGANISM: Unknown
<220> FEATURE:
<223> OTHER INFORMATION: Description of Unknown: Clusterin precursor
      signal sequence

<400> SEQUENCE: 19

Met Met Lys Thr Leu Leu Leu Phe Val Gly Leu Leu Leu Thr Trp Glu
1               5                   10                  15

Ser Gly Gln Val Leu Gly
            20

<210> SEQ ID NO 20
<211> LENGTH: 21
<212> TYPE: PRT
<213> ORGANISM: Unknown
<220> FEATURE:
<223> OTHER INFORMATION: Description of Unknown: Insulin-like growth
      factor-binding protein 4 signal sequence

<400> SEQUENCE: 20

Met Leu Pro Leu Cys Leu Val Ala Ala Leu Leu Leu Ala Ala Gly Pro
1               5                   10                  15

Gly Pro Ser Leu Gly
            20

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 21

Asp Tyr Lys Asp Asp Asp Lys
1               5

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gactacaagg atgacgacga caag                                         24

<210> SEQ ID NO 23
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Leu Glu Leu Val Pro Arg Gly Ser Gly Asp Pro Ile Glu Gly Arg Gly
1               5                   10                  15

Gly Gly Gly Gly Asp Pro Lys Ser Cys Asp Lys Pro His Thr Cys Pro
                20                  25                  30

Leu Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Ala Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250